(12) United States Patent
Arena et al.

(10) Patent No.: US 10,448,989 B2
(45) Date of Patent: *Oct. 22, 2019

(54) HIGH-FREQUENCY ELECTROPORATION FOR CANCER THERAPY

(75) Inventors: Christopher B. Arena, Blacksburg, VA (US); Rafael V. Davalos, Blacksburg, VA (US); Michael B. Sano, Blacksburg, VA (US)

(73) Assignee: Virginia Tech Intellectual Properties, Inc., Blacksburg, VA (US)

(*) Notice: Subject to any disclaimer, the term of this patent is extended or adjusted under 35 U.S.C. 154(b) by 876 days.

This patent is subject to a terminal disclaimer.

(21) Appl. No.: 13/332,133

(22) Filed: Dec. 20, 2011

(65) Prior Publication Data

US 2012/0109122 A1 May 3, 2012

Related U.S. Application Data

(63) Continuation-in-part of application No. 12/757,901, filed on Apr. 9, 2010.

(Continued)

(51) Int. Cl.
*A61B 18/12* (2006.01)
*A61B 18/14* (2006.01)
(Continued)

(52) U.S. Cl.
CPC .............. *A61B 18/14* (2013.01); *A61N 1/327* (2013.01); *A61B 2018/0016* (2013.01);
(Continued)

(58) Field of Classification Search
CPC ................ A61B 18/14; A61B 18/1206; A61B 2018/0016; A61B 2018/00613
(Continued)

(56) References Cited

U.S. PATENT DOCUMENTS

| 1,653,819 A | 12/1927 | Northcott et al. |
| 3,730,238 A | 5/1973 | Butler |

(Continued)

FOREIGN PATENT DOCUMENTS

| AU | 2002315095 A1 | 12/2002 |
| AU | 2003227960 A1 | 12/2003 |

(Continued)

OTHER PUBLICATIONS

Co-Pending U.S. Appl. No. 12/757,901, Response to Final Rejection with RCE, dated Feb. 3, 2014, 11 pages.

(Continued)

*Primary Examiner* — Daniel W Fowler
(74) *Attorney, Agent, or Firm* — New River Valley IP Law, PC; Michele L. Mayberry

(57) ABSTRACT

The present invention relates to the field of biomedical engineering and medical treatment of diseases and disorders. Methods, devices, and systems for in vivo treatment of cell proliferative disorders are provided. In embodiments, the methods comprise the delivery of high-frequency bursts of bipolar pulses to achieve the desired modality of cell death. More specifically, embodiments of the invention relate to a device and method for destroying aberrant cells, including tumor tissues, using high-frequency, bipolar electrical pulses having a burst width on the order of microseconds and duration of single polarity on the microsecond to nanosecond scale. In embodiments, the methods rely on conventional electroporation with adjuvant drugs or irreversible electroporation to cause cell death in treated tumors. The invention can be used to treat solid tumors, such as brain tumors.

43 Claims, 25 Drawing Sheets

Related U.S. Application Data

(60) Provisional application No. 61/167,997, filed on Apr. 9, 2009, provisional application No. 61/285,618, filed on Dec. 11, 2009, provisional application No. 61/424,872, filed on Dec. 20, 2010.

(51) Int. Cl.
*A61N 1/32* (2006.01)
*A61B 18/00* (2006.01)

(52) U.S. Cl.
CPC .............. *A61B 2018/00577* (2013.01); *A61B 2018/00613* (2013.01); *A61B 2018/00761* (2013.01); *A61B 2018/00767* (2013.01)

(58) Field of Classification Search
USPC .............................................. 606/27, 34, 41
See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A * | 11/1983 | Newton et al. ............ 606/35 |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu'Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann |
| 5,718,246 A | 2/1998 | Vona |

(56) References Cited

U.S. PATENT DOCUMENTS

| | | |
|---|---|---|
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Nanda et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A * | 11/2000 | Nanda ............... C12M 35/02 204/547 |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,558,378 B2 | 5/2003 | Sherman et al. |
| 6,562,604 B2 | 5/2003 | Rubinsky |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Rubinsky |
| 6,616,657 B2 | 9/2003 | Simpson et al. |

(56) References Cited

U.S. PATENT DOCUMENTS

| | | |
|---|---|---|
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | McGovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,712,811 B2 | 3/2004 | Underwood et al. |
| D489,973 S | 5/2004 | Root et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 * | 12/2005 | Zhang ............ A61N 1/327 604/20 |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 * | 9/2006 | Sun et al. ............ 604/21 |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sander |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |

(56) References Cited

U.S. PATENT DOCUMENTS

| | | |
|---|---|---|
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 | 8/2016 | Callas et al. |
| 9,598,691 B2 | 3/2017 | Davalos |
| 9,867,652 B2 | 1/2018 | Sane et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith, III |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1* | 3/2003 | Dzekunov ............... C12N 15/87 435/461 |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1* | 11/2003 | Heil, Jr. ............... A61N 1/3625 607/3 |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Mackoviak |
| 2004/0267189 A1 | 12/2004 | Mavor et al. |
| 2004/0267340 A1 | 12/2004 | Cioanta et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | McHale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |

(56) References Cited

U.S. PATENT DOCUMENTS

| | | |
|---|---|---|
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem |
| 2007/0025919 A1* | 2/2007 | Deem et al. ............ 424/45 |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129760 A1* | 6/2007 | Demarais ........ A61B 18/1492 607/2 |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1* | 8/2008 | Long ............... 606/37 |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326436 A1 | 12/2009 | Rubinsky et al. |
| 2009/0326570 A1 | 12/2009 | Brown |
| 2010/0004623 A1 | 1/2010 | Hamilton et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0106221 A1 | 5/2011 | Neal et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071872 A1 | 3/2012 | Rubinsky et al. |

(56) References Cited

U.S. PATENT DOCUMENTS

| | | |
|---|---|---|
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Neal et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sane et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320488 A1 | 11/2015 | Moshe et al. |
| 2015/0327944 A1 | 11/2015 | Davalos et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338761 A1 | 11/2016 | Chornenky et al. |
| 2016/0354142 A1 | 12/2016 | Pearson et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0360326 A1 | 12/2017 | Davalos |
| 2018/0125565 A1 | 5/2018 | Sano et al. |
| 2018/0161086 A1 | 6/2018 | Davalos et al. |
| 2019/0029749 A1 | 1/2019 | Garcia |
| 2019/0046255 A1 | 2/2019 | Davalos et al. |
| 2019/0069945 A1 | 3/2019 | Davalos et al. |
| 2019/0133671 A1 | 5/2019 | Davalos et al. |
| 2019/0175248 A1 | 6/2019 | Neal, II |
| 2019/0175260 A1 | 6/2019 | Davalos |

FOREIGN PATENT DOCUMENTS

| | | |
|---|---|---|
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| CA | 2297846 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| DE | 863111 | 1/1953 |
| DE | 4000893 | 7/1991 |
| DE | 60038026 | 2/2009 |
| EP | 0218275 A1 | 4/1987 |
| EP | 0339501 A2 | 11/1989 |
| EP | 0378132 | 7/1990 |
| EP | 0533511 A1 | 3/1993 |
| EP | 0935482 A | 8/1999 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2381829 A1 | 11/2011 |
| EP | 2413833 A1 | 2/2012 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| KR | 101034682 A | 5/2011 |
| WO | 9104014 | 4/1991 |
| WO | 9634571 | 11/1996 |
| WO | 9639531 | 12/1996 |
| WO | 9810745 | 3/1998 |
| WO | 9814238 | 4/1998 |
| WO | 9814238 A | 4/1998 |

(56) References Cited

FOREIGN PATENT DOCUMENTS

| | | |
|---|---|---|
| WO | 9901076 | 1/1999 |
| WO | 9904710 | 2/1999 |
| WO | 0020554 | 4/2000 |
| WO | 0107584 | 2/2001 |
| WO | 0107585 | 2/2001 |
| WO | 0110319 A | 2/2001 |
| WO | WO 01/07583 | 2/2001 |
| WO | WO 01/10319 | 2/2001 |
| WO | 048153 | 7/2001 |
| WO | 2001048153 A1 | 7/2001 |
| WO | 0170114 A1 | 9/2001 |
| WO | 0181533 | 11/2001 |
| WO | WO 02/78527 | 10/2002 |
| WO | 02089686 A | 11/2002 |
| WO | WO 02/089686 | 11/2002 |
| WO | 02100459 A | 12/2002 |
| WO | WO 02/100459 | 12/2002 |
| WO | 2003020144 A1 | 3/2003 |
| WO | 2003047684 A2 | 6/2003 |
| WO | 03099382 A | 12/2003 |
| WO | WO 03/099382 | 12/2003 |
| WO | 04037341 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A1 | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |

OTHER PUBLICATIONS

Non-Final Office Action of Co-pending U.S. Appl. No. 12/757,901, dated Mar. 11, 2013.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Co-pending U.S. Appl. No. 10/571,162, filed Oct. 18, 2006 (published as 2007/0043345 on Feb. 22, 2007).
Extended European Search Report. dated May 11, 2012. PCT/US2009042100.
Gilbert, T. W., et al., "Decellularization of tissues and organs", Biomaterials, Elsevier Science Publishers, Barking, GB, vol. 27, No. 19, Jul. 1, 2006, pp. 3675-3683.
Maor et al., The Effect of Irreversible Electroporation on Blood Vessels, Tech. in Cancer Res. and Treatment, vol. 6, No. 4, Aug. 2007, pp. 307-312.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
PCT International Preliminary Report on Patentability for PCT/US09/62806, dated Jan. 4, 2012, 6pgs.
PCT International Search Report (dated Aug. 2, 2011), Written Opinion (dated Aug. 2, 2011), and International Preliminary Report on Patentability (dated Apr. 17, 2012) of PCT/US10/53077.
PCT International Search Report (dated Jul. 15, 2010), Written Opinion (dated Jul. 15, 2010), and International Preliminary Report on Patentability (dated Oct. 11, 2011) from PCT/US2010/030629.
PCT International Search Report (dated Jul. 9, 2009), Written Opinion (dated Jul. 9, 2009), and International Preliminary Report on Patentability (dated Nov. 2, 2010) of PCT/US2009/042100.
Rubinsky, B., "Irreversible Electroporation in Medicine", Technology in Cancer Research and Treatment, vol. 6, No. 4, Aug. 1, 2007, pp. 255-259.
Sano, M. B., et al., "Towards the creation of decellularized organ constructs using irreversible electroporation and active mechanical perfusion", Biomedical Engineering Online, Biomed Central Ltd, London, GB, vol. 9, No. 1, Dec. 10, 2010, p. 83.
Co-Pending International Application No. PCT/US2011/066239, International Preliminary Report on Patentability dated Jun. 25, 2013, 7 pages.
Co-Pending U.S. Appl. No. 12/757,901, Final Rejection dated Oct. 2, 2013, 11 pages.
Co-Pending U.S. Appl. No. 12/757,901, Non-Final Rejection dated Mar. 11, 2013, 12 pages.
Co-Pending U.S. Appl. No. 12/757,901, Response to Non-Final Rejection dated Aug. 12, 2013, 11 pages.
Co-Pending U.S. Appl. No. 12/906,923, filed Oct. 18, 2010.
Co-Pending Application No. PCT/US10/53077, filed Oct. 18, 2010.
Co-Pending Application No. PCT/US11/62067, filed Nov. 23, 2011.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 23, 2013.
Co-Pending U.S. Appl. No. 14/012,832, filed Aug. 28, 2013.
Co-Pending U.S. Appl. No. 14/017,210, filed Sep. 3, 2013.
Co-pending European Application No. 10 824 248.8, Invitation Pursuant to rule 62a(1) EPC (Sep. 25, 2013).
Agerholm-Larsen, B., et al., "Preclinical Validation of Electrochemotherapy as an Effective Treatment for Brain Tumors", Cancer Research 71: 3753-3762 (2011).
Appelbaum, L., et al., "US Findings after Irreversible Electroporation Ablation: Radiologic-Pathologic Correlation" Radiology 262(1), 117-125 (2012).
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Bancroft, et al., Design of a Flow Perfusion Bioreactor System for Bone Tissue-Engineering Applications, Tissue Engineering, vol. 9, No. 3, 2003, p. 549-554.
Ben-David, E.,et al., "Characterization of Irreversible Electroporation Ablation in In Vivo Procine Liver" Am. J. Roentgenol. 198(1), W62-W68 (2012).
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).

(56) References Cited

OTHER PUBLICATIONS

Corovic, S., et al., "Analytical and numerical quantification and comparison of the local electric field in the tissue for different electrode configurations," Biomed Eng Online, 6, 2007.
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, R.V., et al., "Electrical impedance tomography for imaging tissue electroporation," IEEE Transactions on Biomedical Engineering, 51, 761-767, 2004.
Demirbas, M. F., "Thermal Energy Storage and Phase Change Materials: An Overview" Energy Sources Part B 1(1), 85-95 (2006).
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Faroja, M., et al., "Irreversible Electroporation Ablation: Is the entire Damage Nonthermal?", Radiology, 266(2), 462-470 (2013).
Foster RS, "High-intensity focused ultrasound in the treatment of prostatic disease", European Urology, 1993, vol. 23 Suppl 1, pp. 29-33.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS ONE, Aug. 2012, 7:8, e42817.
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e18831.
Mahmood, F., et al., "Diffusion-Weighted MRI for Verification of Electroporation-Based Treatments", Journal of Membrane Biology 240: 131-138 (2011).
Mahnic-Kalamiza, S., et al., "Educational application for visualization and analysis of electric field strength in multiple electrode electroporation," BMC Med Educ, vol. 12, p. 102, 2012.
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-1085. Epub Jan. 6, 2012, 2012.
Neal II, R. E., et al., "Successful Treatment of a Large Soft Tissue Sarcoma with Irreversible Electroporation", Journal of Clinical Oncology, 29:13, e372-e377 (2011).
Rubinsky, B., et al., "Irreversible Electroporation: A New Ablation Modality—Clinical Implications" Technol. Cancer Res. Treatment 6(1), 37-48 (2007).
Salford, L.G., et al., "A new brain tumour therapy combining bleomycin with in vivo electropermeabilization", Biochem. Biophys. Res. Commun., 194(2): 938-943 (1993).
Sharma, A. , et al., "Review on Thermal Energy Storage with Phase Change Materials and Applications", Renewable Sustainable Energy Rev. 13(2), 318-345 (2009).
Thomson, K. R., et al., "Investigation of the Safety of Irreversible Electroporation in Humans" J. Vascular Int. Radiol. 22(5), 611-621 (2011).
Co-Pending U.S. Appl. No. 13/550,307, filed Jul. 16, 2012.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-2274.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
PCT International Search Report (dated Aug. 22, 2012), and Written Opinion (dated Aug. 22, 2012) of PCT/US11/66239.
PCT International Search Report and Written Opinion (dated Jul. 25, 2012) of PCT/US2011/062067.
Rajagopal, V. and S.G. Rockson, Coronary restenosis: a review of mechanisms and management, The American Journal of Medicine, 2003, 115(7): p. 547-553.
Al-Sakere, B. et al., 2007, "Tumor ablation with irreversible electroporation." PLoS ONE 2.
Davalos, R.V. et al., 2005, "Tissue ablation with irreversible electroporation." Annals of Biomedical Engineering, 3(2):223-231.
Edd, J.F, et al., 2007, "Mathematical modeling of irreversible electroporation for treatment planning.", Technology in Cancer Research and Treatment., 6:275-286.
Garcia et al., "Irreversible electroporation (IRE) to treat brain cancer." ASME Summer Bioengineering Conference, Macro Island, FL, Jun. 25-29, 2008.
PCT International Search Report (dated Jul. 15, 2010), Written Opinion (dated Jul. 15, 2010), and International Preliminary Report on Patentability (dated Oct. 11, 2011) of PCT/US2010/030629.
Co-pending U.S. Appl. No. 12/432,295 (published as 2009/0269317).
Co-pending U.S. Appl. No. 12/491,151 (published as 2010/0030211).
Co-pending U.S. Appl. No. 12/609,779, filed Oct. 30, 2009.
Co-pending U.S. Appl. No. 10/571,162 (published as 2007/0043345).
Co-pending U.S. Appl. No. 12/757,901, filed Apr. 9, 2010.
Telke, Ephrem R. Dean Astumian, and P. Boon Chock,Electroporation by using bipolar oscillating electric field: An improved method for DNA transfection of NIH 3T3 cells, Proc. Natil. Acad. Sci., vol. 88, pp. 4230-4234, May 1991, Biochemistry.
PCT International Search Report (dated Jan. 19, 2010) of PCT/US2009/062806.
Baker, et al., Calcium-Dependent Exocytosis in Bovine Adrenal Medullary Cells with Leaky Plasma Membranes, *Nature*, vol. 276, pp. 620-622, 1978.
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Bown, S.G., Phototherapy of tumors. *World J. Surgery*, 1983. 7: p. 700-9.
BPH Management Strategies: Improving Patient Satisfaction, *Urology Times*, May 2001, vol. 29, Supplement 1.

(56) References Cited

OTHER PUBLICATIONS

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W., et al., "The Electrical Discharge of the Electric Eel, Electrophorous Electricus," Zoologica, 1937, 22(1), pp. 1-32.
Cowley, Good News for Boomers, *Newsweek*, Dec. 30, 1996/Jan. 6, 1997.
Cox, et al., Surgical Treatment of Atrial Fibrillation: A Review, *Europace* (2004) 5, S20-S-29.
Davalos, et al., Theoretical Analysis of the Thermal Effects During in Vivo Tissue Electroporation, Bioelectrochemistry, vol. 61, pp. 99-107, 2003.
Davalos, Real-Time Imaging for Molecular Medicine through Electrical Impedance Tomography of Electroporation, Dissertation for Ph.D. in Engineering—Mechanical Engineering, Graduate Division of University of California, Berkeley, 2002.
Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.
Edd, J., et al., In-Vivo Results of a New Focal Tissue Ablation Technique: Irreversible Electroporaton, *IEEE Trans. Biomed. Eng.* 53 (2006) p. 1409-1415.
Foster, R.S., et al., High-intensity focused ultrasound in the treatment of prostatic disease. *Eur. Urol.*, 1993. 23: 44-7).
Gauger, et al., A Study of Dielectric Membrane Breakdown in the Fucus Egg, *J. Membrane Biol.*, vol. 48, No. 3, pp. 249-264, 1979.
Gilbert, et al., The Use of Ultrasound Imaging for Monitoring Cryosurgery, Proceedings 6$^{th}$ Annual Conference, IEEE Engineering in Medicine and Biology, 107-111, 1984.
Huang, et al., Micro-Electroporation: Improving the Efficiency and Understanding of Electrical Permeabilization of Cells, *Biomedical Microdevices*, vol. 2, pp. 145-150, 1999.
Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.
Miller, L., et al., Cancer cells ablation with irreversible electroporation, *Technology in Cancer Research and Treatment* 4 (2005) 699-706.
Mir, Therapeutic Perspectives of in Vivo Cell Electropermeabilization, *Bioelectrochemistry*, vol. 53, pp. 1-10, 2000.
Mir, L.M., et al., Electric Pulse-Mediated Gene Delivery to Various Animal Tissues, in Advances in Genetics, Academic Press, 2005, p. 83-114.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Naslund, Michael J., Transurethral Needle Ablation of the Prostate, *Urology*, vol. 50, No. 2, Aug. 1997.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Neumann, et al., Gene Transfer into Mouse Lyoma Cells by Electroporation in High Electric Fields, *J. Embo.*, vol. 1, No. 7, pp. 841-845, 1982.
Onik, et al., Sonographic Monitoring of Hepatic Cryosurgery in an Experimental Animal Model, *AJR American J. of Roentgenology*, vol. 144, pp. 1043-1047, May 1985.
Onik, et al., Ultrasonic Characteristics of Frozen Liver, *Cryobiology*, vol. 21, pp. 321-328, 1984.
Organ, L.W., Electrophysiological principles of radiofrequency lesion making, *Apply. Neurophysiol.*, 1976. 39: p. 69-76.
Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Precision Office TUNA System, When Patient Satisfaction is Your Goal, VidaMed 2001.
Rols, M.P., et al., Highly Efficient Transfection of Mammalian Cells by Electric Field Pulses: Application to Large Volumes of Cell Culture by Using a Flow System, *Eur. J. Biochem*. 1992, 206, pp. 115-121.
Rubinsky, B., ed, Cryosurgery. *Annu Rev. Biomed*. Eng. vol. 2 2000. 157-187.
Shiina, S., et al, Percutaneous ethanol injection therapy for hepatocellular carcinoma: results in 146 patients. *AJR*, 1993, 160: p. 1023-8.
Thompson, et al., To determine whether the temperature of 2% lignocaine gel affects the initial discomfort which may be associated with its instillation into the male urethra, *BJU International* (1999), 84, 1035-1037.
TUNA—Suggested Local Anesthesia Guidelines.
Vidamed, Inc., Transurethral Needle Ablation (TUNA): Highlights from Worldwide Clinical Studies, Vidamed's Office TUNA System, 2001.
Weaver, et al., Theory of Electroporation: A Review, *Bioelectrochemistry and Bioenergetics*, vol. 41, pp. 136-160, 1996.
Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Amasha et al., Clin Phys. Physiol Meas, 9:49-53 (1988).
Andreason (1993) J. Tiss. Cult. Meth. 15:56-62.
Barber (1993) Advances in Biomedical Engineering, pp. 165-173. Beneken and Thevenia (eds) IOS Press pp. 165-173 (1993).
Blad et al., Physiol Meas., 17:A105-A115 (1996).
Brown et al., Clin Phys Physiol Meas, 13:175-179 (1992).
Cook et al. (Aug. 1994) IEEE Transactions on Biomedical Engineering, 41(6):713-722.
Crowly, Biophysical Journal, 13:711-724 (1973).
Davalos et al., IEEE Transactions on Biomedical Engineering, 49(4):400-403 (Apr. 2002).
Davalos et al., Annals of Biomedical Engineering 33(2):223-231 (Feb. 2005).
Dean et al., Am. J. Physiol. Cell Physiol., 289:233-235 (2005).
Dev et al., IEEE Transactions of Plasma Science, 28(1):206-223 (Feb. 2000).
Duraiswami et al., (1998) Engineering and Analysis with Boundary Elements, 22:13-31.
Duraiswami et al. (1997) Chemical Engineering Science, 32(13:2185-2196.
Duraiswami et al. (1997) Boundary Element Technology XII, pp. 226-237.
Erez et al., J. Biomech. Eng., 102(1):42-9 (1980).
Fox et al. (May 1997), Sampling Conductivity Images Via MCMC, Mathematics Department, Auckland University, New Zealand.
Gehl et al., Biochimica et Biophysica Acta, 1428:233-240 (1999).
Gencer et al. (Feb. 1996) Transactions on Biomedical Engineering, 43(2):139-149.
Gilbert et al. (1997), Biochimica et Biophysica Act, 1334:9-14.
Gothelf et al., Cancer Treatment Reviews, 29:371-387 (2003).
Griffiths et al. (Oct. 1989) Phys. Med. Biol., 34(10):1465-1476.
Griffiths et al. (1995), IEEE Transactions on Biomedical Engineering, 42:948-954.
Griffiths et al. (1987) Phys. Med. Biol., 32(11):1435-1444 (1987).
Glidewell et al., (1993) Biomed Sci Instrum, 29:251-257.
Gumerov et al. (Jun. 1999) 13$^{th}$ International Conference on Boundary Element Technology, BETECH, Las Vegas Nevada.
Hapala (1997) Critical Reviews in Biotechnology, 17:105-122.
Heller et al. (1999) Advanced Drug Delivery Reviews, 35:119-129.
Ho et al. (1996) Critical Reviews in Biotechnology 16:349-362.
Holder et al. (1997) Proceedings of the X. International Conference on Electrical Bioimpedance, pp. 512-519.
Hughes et al. (1994) Physiol Meas, 15:A199-A209.
Ivanusa et al., Radiol Oncol., 35(2):139-147 (2001).

(56) References Cited

OTHER PUBLICATIONS

Jaroszeski et al. (1999) Advanced Drug Delivery Reviews 35:131-137.
Kinosita et al., PNAS, 74(5):1923-1927 (May 1977).
Liu et al. (1992) Clin Phys Physiol Meas 13(Supp. A):197-200.
Lurquin (1997) Molecular Biotechnology, 7:5-35.
Lundqvist et al. (1998) Proc Natl Acad Sci USA, 95:10356-10360.
Lynn et al., J. Gen. Physiol, 26:179-93 (1942).
Miklavcic et al., Biophysical Journal, 74:2152-2158 (May 1998).
Miklavcic et al., Biochimica et Biophysica Acta, 1523:73-83(2000).
Mir et al (1991) C.R. Acad Sci Paris, 313(III):613-618.
Mir et al., European Journal of Cancer, 27:68-72 (1991).
Mir et al., British Journal of Cancer, 77(12):2336-2342 (1998).
Narayan et al. (1992) J. Urol., 148:1600-1604.
Neumann et al., J. Membrane Biol., 10:279-290 (1972).
Okino et al., Japanese Journal of Cancer Resesarch, 78(12):1319-21 (1987).
Schmuckler (1994) Engineering in Medicine and Biology Society, Engineering Advances: New Opportunities for Biomedical Engineers, Proceedings of the 16$^{th}$ Annual Internal Conference of the IEEE, vol. 1, p. A74.
Sersa et al., Br. J. Cancer, 87(9):1047-54 (2002).
Sersa et al., Oncol., 37(1):43-8 (2003).
Sharma et al (1996) Biophysical Journal, vol. 71:3229-3241.
Weaver (1993) Journal of Cellular Biochemistry, 51:426-435.
Zimmerman et al., Biophysical Journal, 14(11):881-889 (1974).
PCT International Search Report (dated Aug. 26, 2005), Written Opinion (dated Aug. 26, 2005), and Int'l Preliminary Report on Patentabilty (dated Jun. 26, 2006) of PCT/US2004/043477.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US11/32067, filed Nov. 23, 2011.
Co-Pending Application No. PCT/US11/66239, filed Dec. 20, 2011.
Mir et al., "Mechanisms of Electrochemotherapy" Advanced Drug Delivery Reviews 35:107-118 (1999).
PCT Written Opinion for PCT/US09/62806, dated Jan. 10, 2010, 5pgs.
Boone, K., Barber, D. & Brown, B. Review—Imaging with electricity: report of the European Concerted Action on Impedance Tomography. J. Med. Eng. Technol. 21, 201-232 (1997).
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Garcia, P. et al. Intracranial nonthermal irreversible electroporation: in vivo analysis. J Membr Biol 236, 127-136 (2010).
International Preliminary Report on Patentability of Corresponding International Application No. PCT/2011/066239, dated Jun. 25, 2013.
Jossinet et al., Electrical Impedance Endo-Tomography: Imaging Tissue From Inside, IEEE Transactions on Medical Imaging, vol. 21, No. 6, Jun. 2002, pp. 560-565.
Lee, E. W. et al. Advanced Hepatic Ablation Technique for Creating Complete Cell Death : Irreversible Electroporation. Radiology 255, 426-433, doi:10.1148/radiol.10090337 (2010).
Pavselj, N. et al. The course of tissue permeabilization studied on a mathematical model of a subcutaneous tumor in small animals. IEEE Trans Biomed Eng 52, 1373-1381 (2005).
Phillips, M., Maor, E. & Rubinsky, B. Non-Thermal Irreversible Electroporation for Tissue Decellularization. J. Biomech. Eng, doi:10.1115/1.4001882 (2010).
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).

Weaver, J. C., Electroporation of biological membranes from multicellular to nano scales, IEEE Trns. Dielectr. Electr. Insul. 10, 754-768 (2003).
International Preliminary Report on Patentability of Corresponding International Application No. PCT/2011/062067, dated May 28, 2013.
Co-pending U.S. Appl. No. 12/757,901, Official Notice of Allowance dated Nov. 4, 2014, 10 pages.
Zhang, Y., et al., MR imaging to assess immediate response to irreversible electroporation for targeted ablation of liver tissues: preclinical feasibility studies in a rodent model. Radiology, 2010. 256(2): p. 424-32.
Alberts et al., "Molecular Biology of the Cell," 3rd edition, Garland Science, New York, 1994, 1 page.
Asami et al., "Dielectric properties of mouse lymphocytes and erythrocytes." Biochimica et Biophysica Acta (BBA)—Molecular Cell Research, 1010 (1989) pp. 49-55.
Bower et al., "Irreversible electroporation of the pancreas: definitive local therapy without systemic effects." Journal of surgical oncology, 2011. 104(1): p. 22-28.
Eppich et al., "Pulsed electric fields for selection of hematopoietic cells and depletion of tumor cell contaminants." Nature Biotechnology 18, pp. 882-887 (2000).
Ermolina et al., "Study of normal and malignant white blood cells by time domain dielectric spectroscopy." IEEE Transactions on Dielectrics and Electrical Insulation, 8 (2001) pp. 253-261.
Fischbach et al., "Engineering tumors with 3D scaffolds." Nat Meth 4, pp. 855-860 (2007).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)—Biomembranes, 471 (1977) pp. 227-242.
Lebar et al., "Inter-pulse interval between rectangular voltage pulses affects electroporation threshold of artificial lipid bilayers." IEEE Transactions on NanoBioscience, vol. 1 (2002) pp. 116-120.
Ron et al., "Cell-based screening for membranal and cytoplasmatic markers using dielectric spectroscopy." Biophysical chemistry, 135 (2008) pp. 59-68.
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." The Journal of Urology, 180 (2008) pp. 2668-2674.
Sano et al., "Contactless Dielectrophoretic Spectroscopy: Examination of the Dielectric Properties of Cells Found in Blood." Electrophoresis, 32, pp. 3164-3171, 2011.
Schoenbach et al., "Intracellular effect of ultrashort electrical pulses." Bioelectromagnetics, 22 (2001) pp. 440-448.
Yao et al., "Study of transmembrane potentials of inner and outer membranes induced by pulsed-electric-field model and simulation." IEEE Trans Plasma Sci, 2007. 35(5): p. 1541-1549.
Co-pending U.S. Appl. No. 12/751,826, filed Mar. 31, 2010 (published as 2010/0250209 on Sep. 30, 2010).
Co-pending U.S. Appl. No. 12/751,854, filed Mar. 31, 2010 (published as 2010/0249771 on Sep. 30, 2010).
Co-Pending Application No. PCT/US15/30429, filed May 12, 2015.
Co-pending Application No. PCT/US2010/029243, filed Mar. 30, 2010, published as WO 2010/117806 on Oct. 14, 2010.
PCT International Search Report, 4 pgs, (dated Jul. 30, 2010), Written Opinion, 7 pgs, (dated Jul. 30, 2010), and International Preliminary Report on Patentability, 8 pgs, (dated Oct. 4, 2011) from PCT/US2010/029243.
A.I. Daud et al., "Phase I Trial of Interleukin-12 Plasmid Electroporation in Patients With Metastatic Melanoma," Journal of Clinical Oncology, 26, pp. 5896-5903, 2008.
Co-Pending U.S. Appl. No. 14/558,631, filed Dec. 2, 2014.
Co-Pending U.S. Appl. No. 14/627,046, filed Feb. 20, 2015.

(56) References Cited

OTHER PUBLICATIONS

Co-Pending U.S. Appl. No. 14/686,380, filed Apr. 14, 2015.
Golberg, A. and Rubinsky, B., "A statistical model for multidimensional irreversible electroporation cell death in tissue." Biomed Eng Online, 9, 13 pages, 2010.
Neal II et al., "A Case Report on the Successful Treatment of a Large Soft-Tissue Sarcoma with Irreversible Electroporation," Journal of Clinical Oncology, 29, pp. 1-6, 2011.
Weisstein: Cassini Ovals. From MathWorld—A. Wolfram Web Resource; Apr. 30, 2010; http://mathworld.wolfram.com/ (updated May 18, 2011).
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Ball, C., K.R. Thomson, and H. Kavnoudias, "Irreversible electroporation: a new challenge in "out of-operating theater" Anesthesia." Anesth Analg, 2010. 110(5): p. 1305-9.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Clark et al., "The electrical properties of resting and secreting pancreas." The Journal of Physiology, vol. 189, pp. 247-260 (1967).
Co-Pending U.S. Appl. No. 12/757,901, Issued as U.S. Pat. No. 8,926,606 on Jan. 6, 2015, 42 pages.
Co-Pending U.S. Appl. No. 14/808,679, filed Jul. 24, 2015.
Dahl et al., "Nuclear shape, mechanics, and mechanotransduction." Circulation Research vol. 102, pp. 1307-1318 (2008).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Gascoyne et al., "Membrane changes accompanying the induced differentiation of Friend murine erythroleukemia cells studied by dielectrophoresis." Biochimica et Biophysica Acta (BBA)—Biomembranes, vol. 1149, pp. 119-126 (1993).
Gimsa et al., "Dielectric spectroscopy of single human erythrocytes at physiological ionic strength: dispersion of the cytoplasm." Biophysical Journal, vol. 71, pp. 495-506 (1996).
Helczynska et al., "Hypoxia promotes a dedifferentiated phenotype in ductal breast carcinoma in situ." Cancer Research, vol. 63, pp. 1441-1444 (2003).
Ibey et al., "Selective cytotoxicity of intense nanosecond-duration electric pulses in mammalian cells." Biochimica Et Biophysica Acta—General Subjects, vol. 1800, pp. 1210-1219 (2010).
Jarm et al., "Antivascular effects of electrochemotherapy: implications in treatment of bleeding metastases." Expert Rev Anticancer Ther. vol. 10, pp. 729-746 (2010).
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Kinosita et al., "Electroporation of cell membrane visualized under a pulsed-laser fluorescence microscope." Biophysical Journal, vol. 53, pp. 1015-1019 (1988).
Kirson et al., "Alternating electric fields arrest cell proliferation in animal tumor models and human brain tumors." Proceedings of the National Academy of Sciences vol. 104, pp. 10152-10157 (2007).
Kotnik and Miklavcic, "Theoretical evaluation of voltage inducement on internal membranes of biological cells exposed to electric fields." Biophysical Journal, vol. 90(2), pp. 480-491 (2006).
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).
Maček Lebar and Miklavčič, "Cell electropermeabilization to small molecules in vitro: control by pulse parameters." Radiology and Oncology, vol. 35(3), pp. 193-202 (2001).
Malpica et al., "Grading ovarian serous carcinoma using a two-tier system." The American Journal of Surgical Pathology, vol. 28, pp. 496-504 (2004).
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Mulhall et al., "Cancer, pre-cancer and normal oral cells distinguished by dielectrophoresis." Analytical and Bioanalytical Chemistry, vol. 401, pp. 2455-2463 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Paszek et al., "Tensional homeostasis and the malignant phenotype." Cancer Cell, vol. 8, pp. 241-254 (2005).
Polak et al., "On the Electroporation Thresholds of Lipid Bilayers: Molecular Dynamics Simulation Investigations." The Journal of Membrane Biology, vol. 246, pp. 843-850 (2013).
Pucihar et al., "Numerical determination of transmembrane voltage induced on irregularly shaped cells." Annals of Biomedical Engineering, vol. 34, pp. 642-652 (2006).
Rossmeisl et al., "Pathology of non-thermal irreversible electroporation (N-TIRE)-induced ablation of the canine brain." Journal of Veterinary Science vol. 14, pp. 433-440 (2013).
Sabuncu et al., "Dielectrophoretic separation of mouse melanoma clones." Biomicrofluidics, vol. 4, 7 pages (2010).
Salmanzadeh et al., "Investigating dielectric properties of different stages of syngeneic murine ovarian cancer cells" Biomicrofiuidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).

(56) References Cited

OTHER PUBLICATIONS

Saur et al., "CXCR4 expression increases liver and lung metastasis in a mouse model of pancreatic cancer." Gastroenterology, vol. 129, pp. 1237-1250 (2005).
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Szot et al., "3D in vitro bioengineered tumors based on collagen I hydrogels." Biomaterials vol. 32, pp. 7905-7912 (2011).
Verbridge et al., "Oxygen-Controlled Three-Dimensional Cultures to Analyze Tumor Angiogenesis." Tissue Engineering, Part A vol. 16, pp. 2133-2141 (2010).
Weaver et al., "A brief overview of electroporation pulse strength-duration space: A region where additional intracellular effects are expected." Bioelectrochemistry vol. 87, pp. 236-243 (2012).
Yang et al., "Dielectric properties of human leukocyte subpopulations determined by electrorotation as a cell separation criterion." Biophysical Journal, vol. 76, pp. 3307-3314 (1999).
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. iii114.
Reberšek, M. and D. Miklavčič, "Advantages and Disadvantages of Different Concepts of Electroporation Pulse Generation," Automatika 52(2011) 1, 12-19.
Baptista et al., "The Use of Whole Organ Decellularization for the Generation of a Vascularized Liver Organoid," Heptatology, vol. 53, No. 2, pp. 604-617 (2011).
Co-Pending U.S. Appl. No. 14/686,380, filed Apr. 14, 2015 and Published as US 2015/0289923 on Oct. 15, 2015.
Co-pending U.S. Appl. No. 15/011,752, filed Feb. 1, 2016.
Co-Pending Application No. PCT/US15/30429, International Search Report and Written Opinion dated Oct. 16, 2015, 19 pages.
Co-Pending Application No. PCT/US2015/030429, Published on Nov. 19, 2015 as WO 2015/175570.
Co-pending U.S. Appl. No. 15/186,653, filed Jun. 20, 2016.
Co-Pending U.S. Appl. No. 14/940,863, filed Nov. 13, 2015 and Published as US 2016/0066977 on Mar. 10, 2016.
Co-Pending U.S. Appl. No. 15/011,752, filed Feb. 1, 2015.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Laufer et al., "Electrical impedance characterization of normal and cancerous human hepatic tissue." Physiological Measurement, vol. 31, pp. 995-1009 (2010).
Beebe, S.J., et al., "Diverse effects of nanosecond pulsed electric fields on cells and tissues", DNA and Cell Biology, 22(12): 785-796 (2003).
Chang, D.C., "Cell Poration and Cell-Fusion Using an Oscillating Electric-Field". Biophysical Journal, 56(4): p. 641-652 (1989).
Chen, M.T., et al., "Two-dimensional nanosecond electric field mapping based on cell electropermeabilization", PMC Biophys, 2(1):9 (2009).
De Vuyst, E., et al., "In situ bipolar Electroporation for localized cell loading with reporter dyes and investigating gap functional coupling", Biophysical Journal, 94(2): p. 469-479 (2008).

Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields". Technology in Cancer Research & Treatment, 8(4): p. 289-306 (2009).
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Gowrishankar T.R., et al., "Microdosimetry for conventional and supra-electroporation in cells with organelles". Biochem Biophys Res Commun, 341(4): p. 1266-76 (2006).
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta-Biomembranes, 1614(2): p. 193-200 (2003).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Long, G., et al., "Targeted Tissue Ablation With Nanosecond Pulses". Ieee Transactions on Biomedical Engineering, 58(8) (2011).
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
PCT IPRP for PCT/US15/30429 (WO2015175570), dated Nov. 15, 2016.
Talele, S., et al., "Modelling single cell electroporation with bipolar pulse parameters and dynamic pore radii". Journal of Electrostatics, 68(3): p. 261-274 (2010).
Vernier, P.T., et al., "Nanoelectropulse-driven membrane perturbation and small molecule permeabilization", Bmc Cell Biology, 7 (2006).
Weaver, J.C., "Electroporation of cells and tissues", IEEE Transactions on Plasma Science, 28(1): p. 24-33 (2000).
Co-pending U.S. Appl. No. 15/423,986, filed Feb. 3, 2017.
Co-pending U.S. Appl. No. 15/424,335, filed Feb. 3, 2017.
Co-Pending U.S. Appl. No. 14/017,210, Petition Decision dated Aug. 2, 2016, 5 pages.
Co-Pending U.S. Appl. No. 14/017,210, Priority Petition Dec. 11, 2015, 5 pages.
Co-Pending U.S. Appl. No. 14/017,210, RCE dated Aug. 1, 2017, 13 pages.
Co-Pending U.S. Appl. No. 14/017,210, RCE dated Nov. 30, 2016, 13 pages.
Co-Pending U.S. Appl. No. 14/017,210, Response to Aug. 30, 2016 Final Office Action, dated Nov. 30, 2016, 10 pages.
Co-Pending U.S. Appl. No. 14/017,210, Response to Dec. 15, 2016 Non-Final Office Action dated Mar. 20, 2017, 9 pages.
Co-Pending U.S. Appl. No. 14/017,210, Response to May 1, 2017 Final Office Action dated Aug. 1, 2017, 10 pages.
Co-Pending U.S. Appl. No. 14/017,210, Response to Non-Final Office Action dated Mar. 8, 2016, 16 pages.
Co-Pending U.S. Appl. No. 14/017,210, Response to Oct. 25, 2017 Non-Final Office Action dated Jan. 25, 2018, 11 pages.
Co-Pending U.S. Appl. No. 14/017,210, Response to Sep. 8, 2015 Non-Final Office Action, dated Mar. 8, 2016, 57 pages.
Co-Pending U.S. Appl. No. 14/017,210, Non-Final Office Action dated Sep. 8, 2015, 8 pages.
Co-Pending U.S. Appl. No. 14/627,046, Amendment dated Jun. 29, 2017, 8 pages.
Co-Pending U.S. Appl. No. 14/627,046, Final Office Action dated Sep. 14, 2017, 11 pages.

(56) References Cited

OTHER PUBLICATIONS

Co-Pending U.S. Appl. No. 14/627,046, Interview Summary dated dated Apr. 27, 2018, 3 pages.
Co-Pending U.S. Appl. No. 14/627,046, Non-Final Office Action dated Feb. 15, 2018, 12 pages.
Co-Pending U.S. Appl. No. 14/627,046, Non-Final Office Action dated Mar. 29, 2017, 9 pages.
Co-Pending U.S. Appl. No. 14/627,046, Notice of Allowance dated Feb. 6, 2019, 5 pages.
Co-Pending U.S. Appl. No. 14/627,046, Notice of Allowance dated Sep. 19, 2018, 7 pages.
Co-Pending U.S. Appl. No. 14/627,046, Response to Mar. 29, 2017 Non-Final Office Action, dated Jun. 29, 2017, 8 pages.
Co-Pending U.S. Appl. No. 14/627,046, Response to Sep. 14, 2017 Final Office Action dated Dec. 14, 2017, 7 pages.
Co-Pending U.S. Appl. No. 14/627,046, Rule 132 Affidavit and Response to Feb. 15, 2018 Non-Final Office Action, dated Jun. 15, 2018, 13 pages.
Co-pending U.S. Appl. No. 16/152,743, filed Oct. 5, 2018.
Co-pending U.S. Appl. No. 16/232,962, filed Dec. 26, 2018.
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Kotnik et al., "Sensitivity of transmembrane voltage induced by applied electric fields—A theoretical analysis", Bioelectrochemistry and Bioenergetics,vol. 43, Issue 2, 1997, pp. 285-291.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Tibbitt et al., "Hydrogels as Extracellular Matrix Mimics for 3D Cell Culture", Jul. 2009, Biotechnol Bioeng, 103(4),655-663.
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.
Co-Pending U.S. Appl. No. 12/757,901, Certificate of Correction, Aug. 2016, 3 pages.
Co-Pending U.S. Appl. No. 12/906,923, Office Actions and Responses dated Jul. 2017, 55 pages.
Co-Pending U.S. Appl. No. 14/808,679, Restriction Requirement dated Mar. 19, 2018, 7 pages.
Co-Pending U.S. Appl. No. 14/808,679, Final Office Action dated Jan. 11, 2019, 12 pages.
Co-Pending U.S. Appl. No. 14/808,679, Non-Final Office Action dated Sep. 10, 2018, 12 pages.
Co-Pending U.S. Appl. No. 14/808,679, Preliminary Amendment, filed Jul. 27, 2015, 9 pages.
Co-Pending U.S. Appl. No. 14/808,679, Response to Mar. 19, 2018 Restriction Requirement dated May 21, 2018, 2 pages.
Co-Pending U.S. Appl. No. 14/808,679, Response to Sep. 10, 2018 Non-Final Office Action dated Dec. 10, 2018, 9 pages.
Co-Pending U.S. Appl. No. 14/940,863, Notice of Allowance dated Jan. 25, 2019, 5 pages.
Co-Pending U.S. Appl. No. 14/940,863, Notice of Allowance dated May 25, 2018, 9 pages.
Co-Pending U.S. Appl. No. 14/940,863, Notice of Allowance dated Sep. 19, 2018, 5 pages.
Co-pending U.S. Appl. No. 15/186,653, Notice of Allowance dated Aug. 1, 2018, 7 pages.
Co-pending U.S. Appl. No. 15/186,653, Notice of Allowance dated Mar. 20, 2019, 9 pages.
Co-pending U.S. Appl. No. 15/186,653, Preliminary Amendment filed Jun. 21, 2016, 5 pages.
Co-Pending U.S. Appl. No. 15/310,114, filed Nov. 10, 2016.
Co-Pending U.S. Appl. No. 15/310,114, NFOA dated Mar. 6, 2019, 13 pages.
Co-Pending U.S. Appl. No. 15/310,114, Preliminary Amendment filed Nov. 10, 2016, 9 pages.
Co-pending U.S. Appl. No. 15/843,888, filed Dec. 15, 2017.
Co-pending U.S. Appl. No. 15/881,414 Amendment and Petition for Priority Claim dated Jul. 26, 2018, 26 pages.
Co-pending U.S. Appl. No. 15/881,414, filed Apr. 26, 2018 Non-Final Office Action, 8 pages.
Co-pending U.S. Appl. No. 15/881,414 Corrected Notice of Allowability dated Nov. 13, 2018, 2 pages.
Co-pending U.S. Appl. No. 15/881,414 Notice of Allowance dated Oct. 24, 2018, 7 pages.
Co-pending U.S. Appl. No. 15/881,414 Petition Decision dated Oct. 9, 2018, 9 pages.
Co-pending U.S. Appl. No. 15/881,414, filed Jan. 26, 2018.
Co-pending U.S. Appl. No. 16/177,745, filed Nov. 1, 2018.
Co-pending U.S. Appl. No. 16/275,429, filed Feb. 14, 2019.
Co-pending U.S. Appl. No. 16/280,511, filed Feb. 20, 2019.
Co-Pending U.S. Appl. No. 13/958,152, Final Office Action dated Dec. 22, 2017, 19 pages.
Co-Pending U.S. Appl. No. 13/958,152, Interview and Supplemental Response to Office Action dated Mar. 2-3, 2017, 12 pages.
Co-Pending U.S. Appl. No. 13/958,152, Interview Summary dated Mar. 2, 2017, 4 pages.
Co-Pending U.S. Appl. No. 13/958,152, Non-Final Office Action dated Jun. 15, 2017, 18 pages.
Co-Pending U.S. Appl. No. 13/958,152, Non-Final Office Action dated Oct. 18, 2018, 20 pages.
Co-Pending U.S. Appl. No. 13/958,152, Response to Dec. 22, 2017 Final Office Action, filed Mar. 22, 2018, 10 pages.
Co-Pending U.S. Appl. No. 13/958,152, Response to Dec. 22, 2017 Final Office Action dated Mar. 22, 2018, 10 pages.
Co-Pending U.S. Appl. No. 13/958,152, Response to Jun. 15, 2017 Non-Final Office Action dated Sep. 15, 2017, 10 pages.
Co-Pending U.S. Appl. No. 13/958,152, Response to Oct. 18, 2018 Non-Final Office Action, filed Jan. 18, 2019, 11 pages.
Co-Pending U.S. Appl. No. 13/958,152, Response to Oct. 21, 2016 Non-Final Office Action, filed Jan. 23, 2017, 25 pages.
Co-Pending U.S. Appl. No. 14/017,210, Acceptance of 312 Amendment dated Sep. 12, 2018, 1 page.
Co-Pending U.S. Appl. No. 14/017,210, AFCP dated Aug. 13, 2018, 9 pages.
Co-Pending U.S. Appl. No. 14/017,210, Final Office Action dated Apr. 11, 2018, 10 pages.
Co-Pending U.S. Appl. No. 14/017,210, Final Office Action dated Aug. 30, 2016, 11 pages.
Co-Pending U.S. Appl. No. 14/017,210, Final Office Action dated May 1, 2017, 11 pages.
Co-Pending U.S. Appl. No. 14/017,210, Non-Final Office Action dated Dec. 15, 2016, 8 pages.
Co-Pending U.S. Appl. No. 14/017,210, Non-Final Office Action dated Oct. 25, 2017, 9 pages.
Co-Pending U.S. Appl. No. 14/017,210, Notice of Allowance (after Dec. 12, 2018 RCE) dated Jan. 9, 2019, 5 pages.
Co-Pending U.S. Appl. No. 14/017,210, Notice of Allowance dated Sep. 12, 2018, 7 pages.
Co-Pending U.S. Appl. No. 14/017,210, Petition dated Dec. 11, 2015, 5 pages.
Co-Pending U.S. Appl. No. 14/017,210, Petition Decision dated Aug. 12, 2016, 9 pages.
Co-Pending U.S. Appl. No. 14/808,679, Interview Summary dated Apr. 26, 2019, 3 pages.
Co-Pending U.S. Appl. No. 14/808,679, Petition for Priority and Supplemental Response, filed May 8, 2019, 25 pages.
Co-Pending U.S. Appl. No. 14/808,679, RCE filed Apr. 11, 2019, 8 pages.
Co-pending U.S. Appl. No. 16/404,392, filed May 6, 2019.
Co-pending U.S. Appl. No. 15/310,114, Response to Mar. 6, 2019 Non-Final Office Action filed Jun. 4, 2019, 8 pages.
Co-pending U.S. Appl. No. 16/275,429 Preliminary Amendment Filed Mar. 28, 2019, 6 pages.
Co-pending U.S. Appl. No. 16/372,520 Preliminary Amendment filed Apr. 9, 2019, 7 pages.

(56) References Cited

OTHER PUBLICATIONS

Co-Pending U.S. Appl. No. 16/375,878, Preliminary Amendment, filed Apr. 9, 2019, 9 pages.
Co-pending U.S. Appl. No. 16/404,392, Petition for Priority, filed Jun. 4, 2019, 2 pages.
Co-pending U.S. Appl. No. 16/404,392, Preliminary Amendment, filed Jun. 4, 2019, 9 pages.
Co-pending U.S. Appl. No. 16/404,392, Preliminary Amendment, filed Jun. 6, 2019, 5 pages.

* cited by examiner

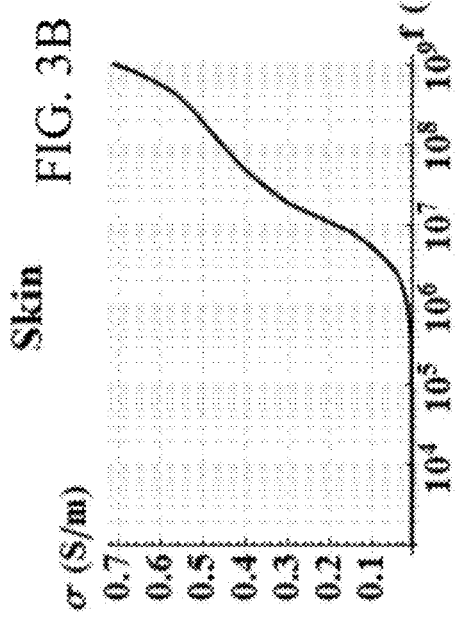
FIG. 3A Skin
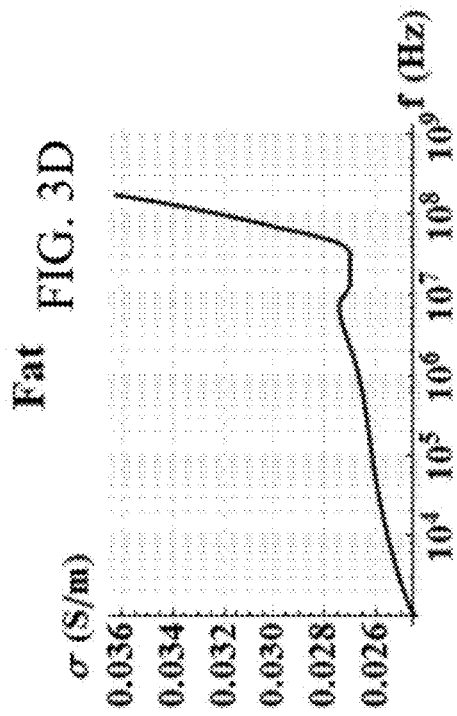
FIG. 3B Skin
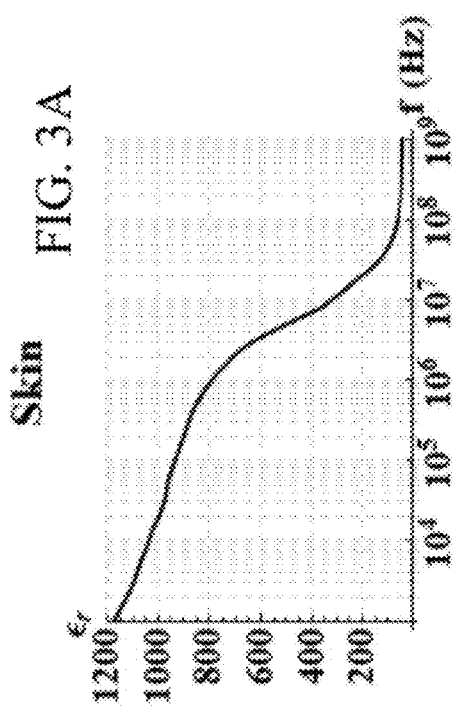
FIG. 3C Fat
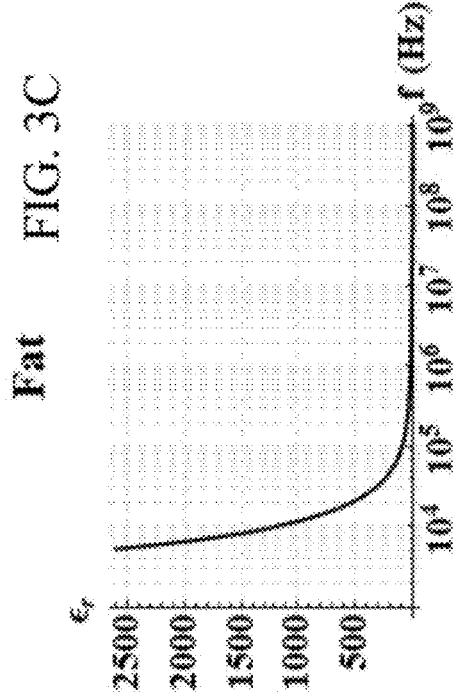
FIG. 3D Fat

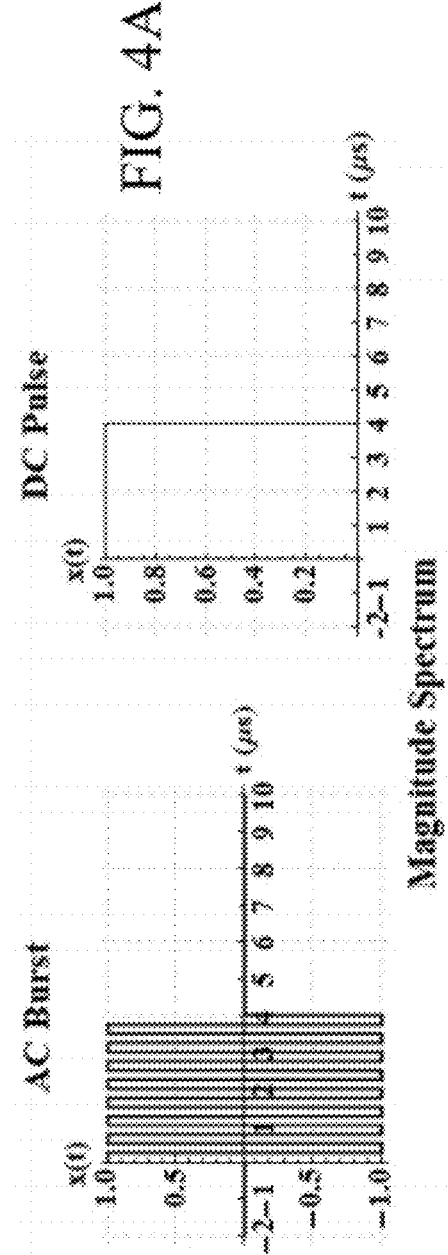
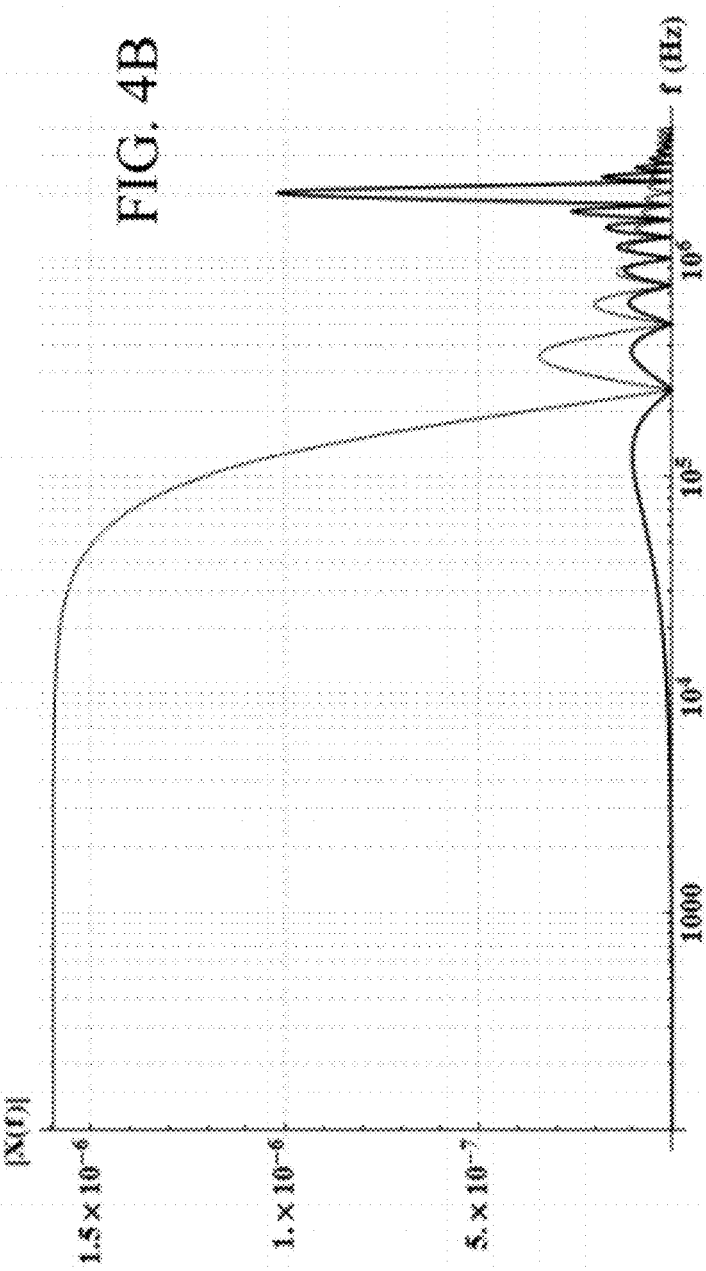
FIG. 4A
FIG. 4B

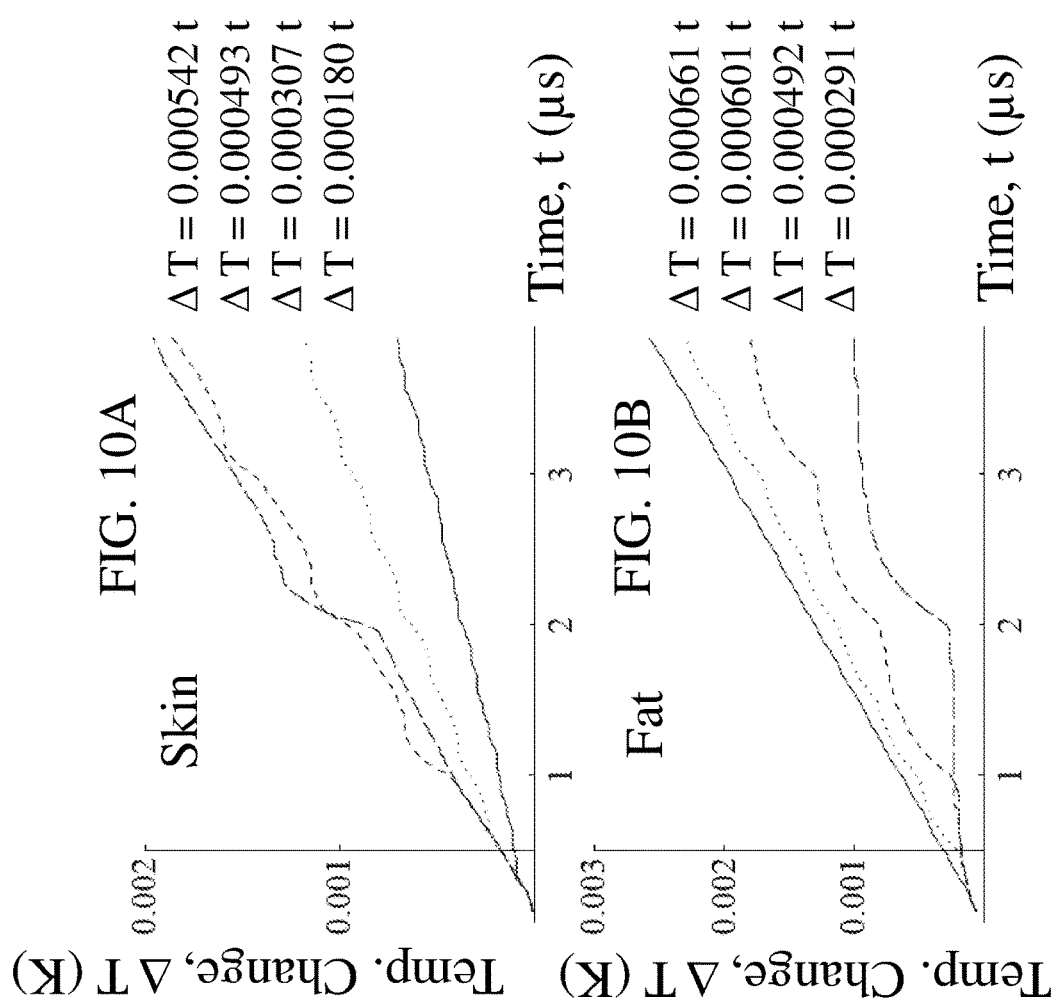

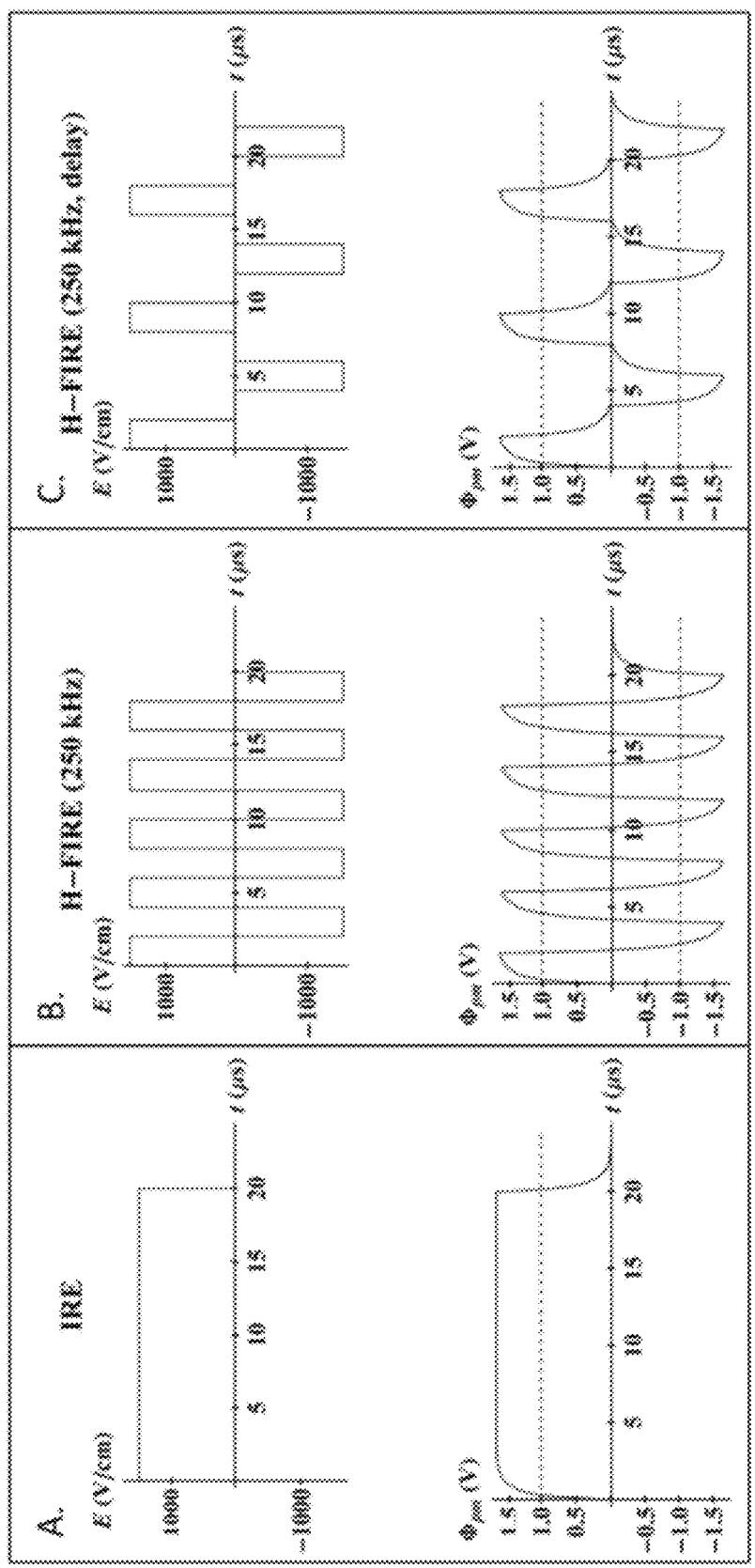
FIGS. 15A-C

FIGS. 17A-C

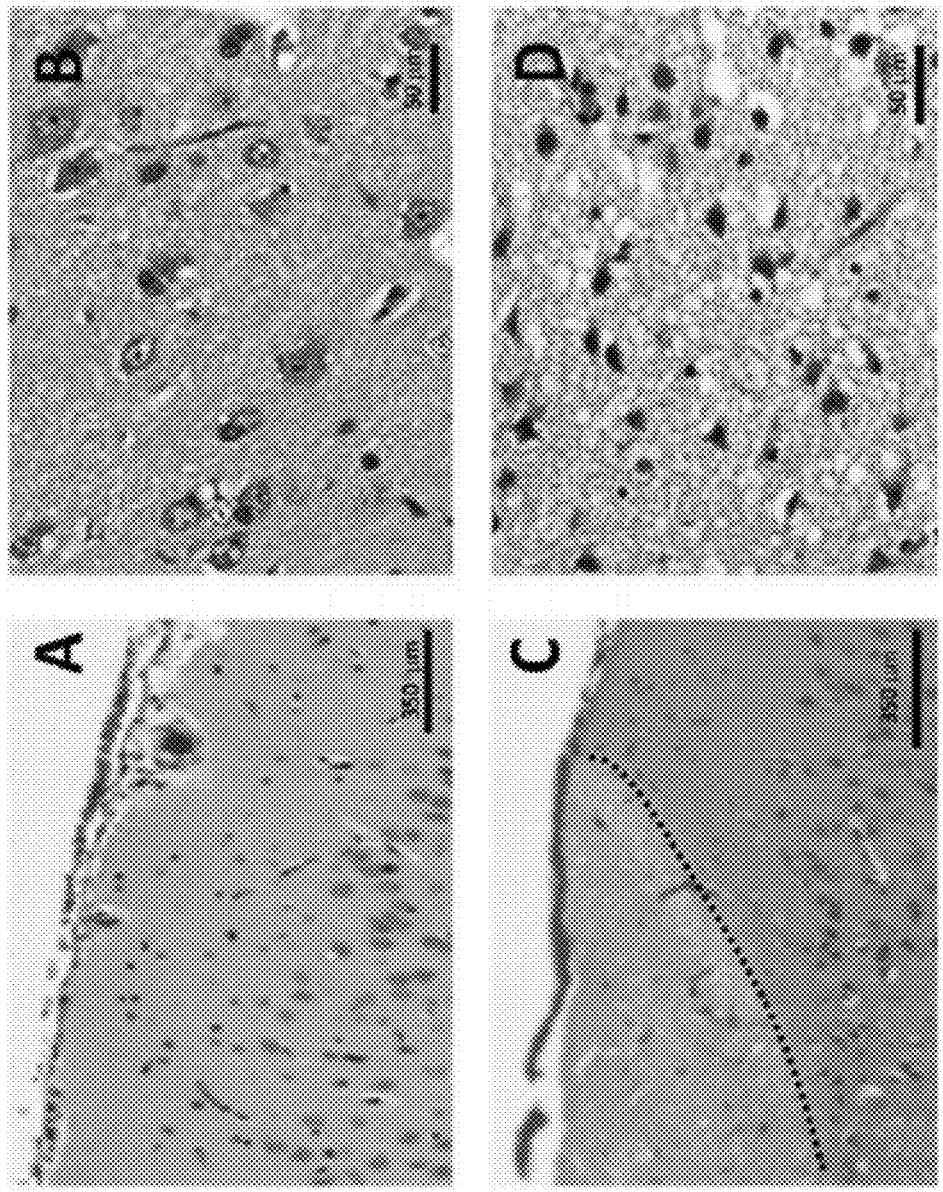
FIGS. 20A-D

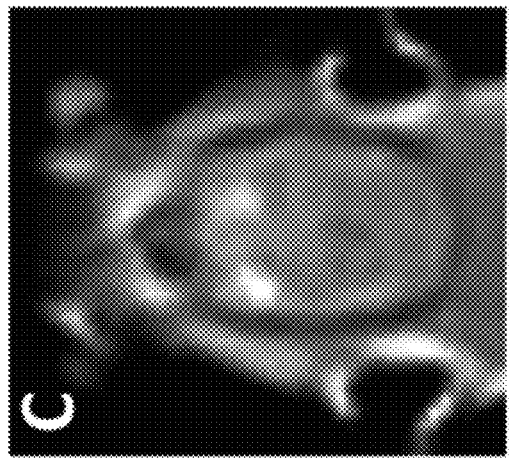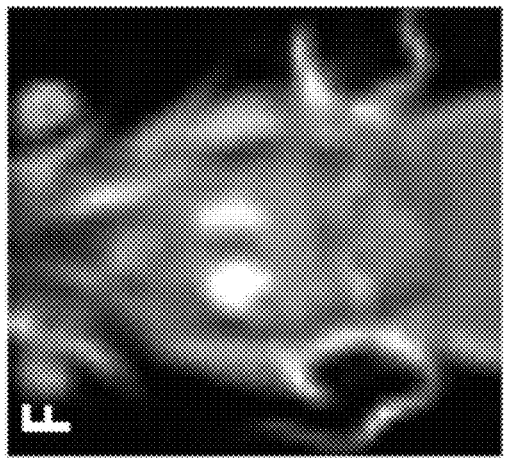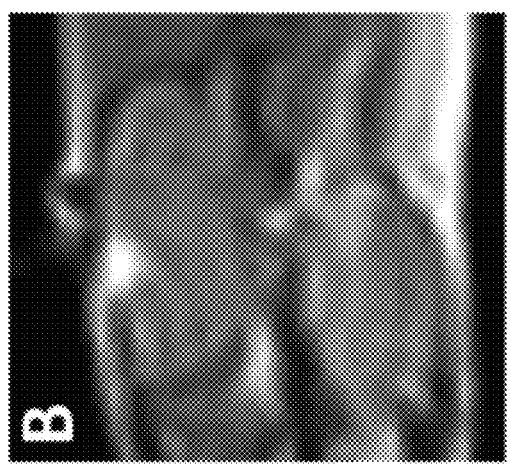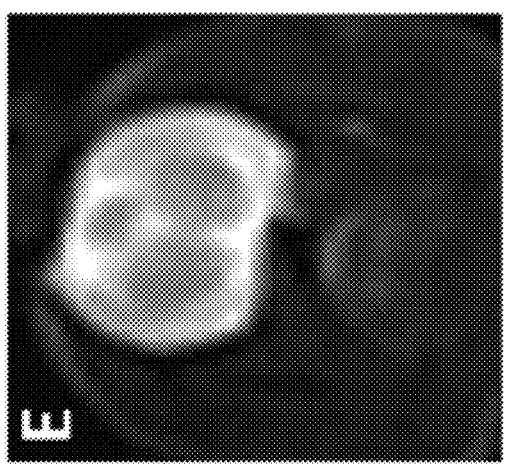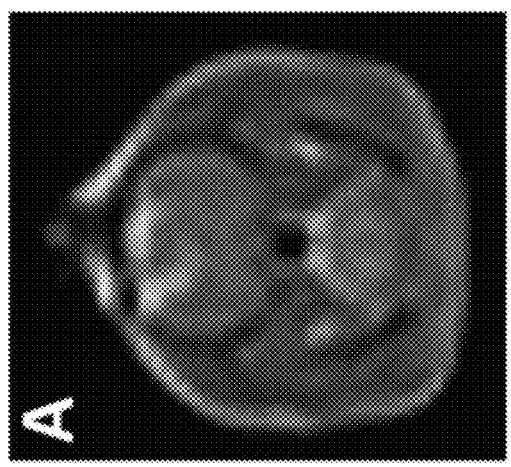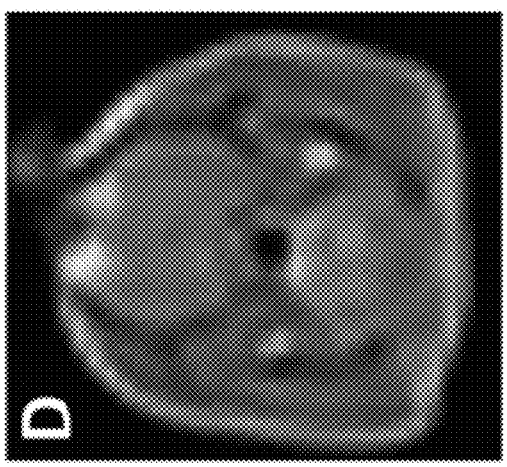
FIGS. 21A-F

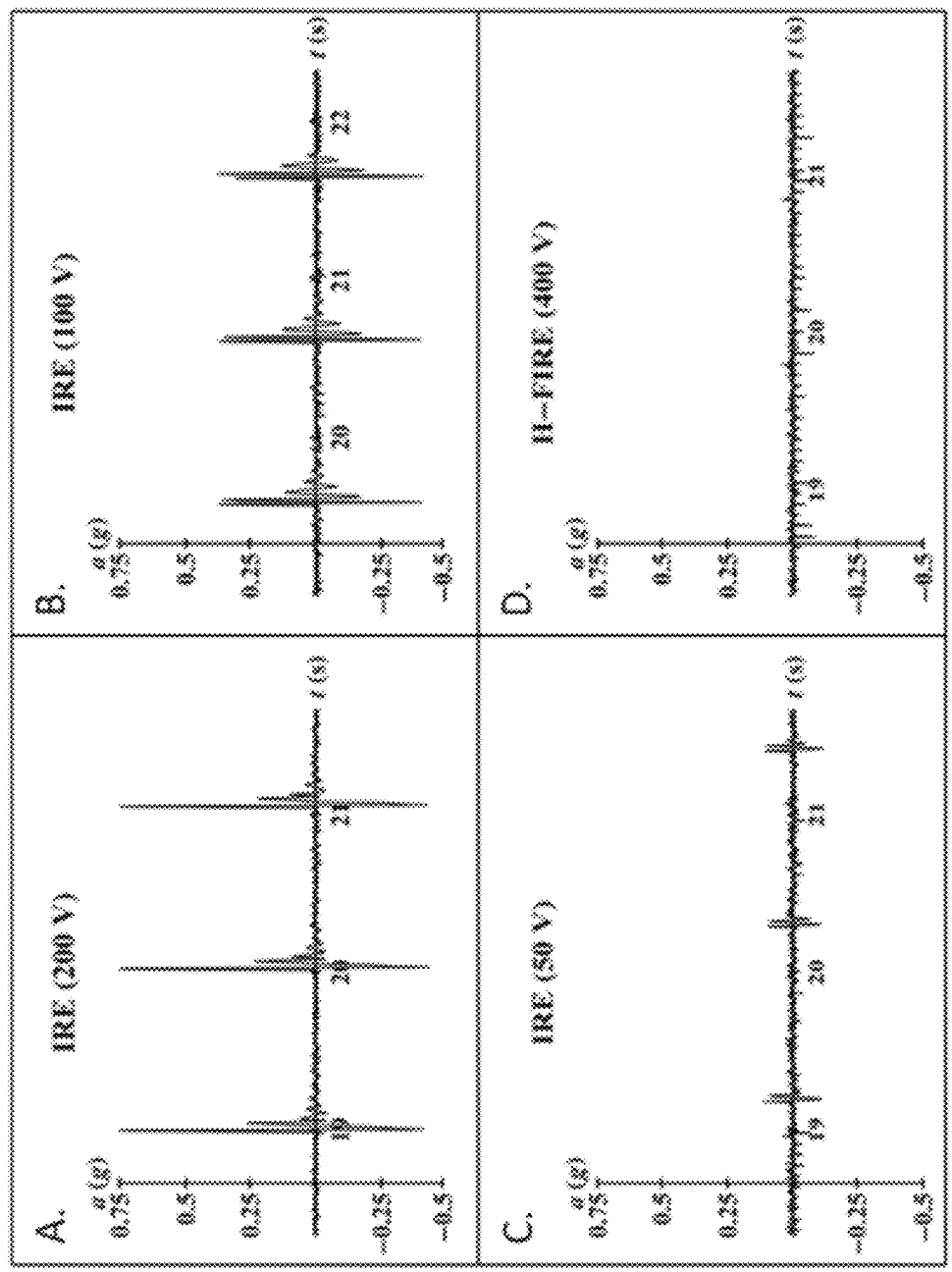
FIGS. 22A-D

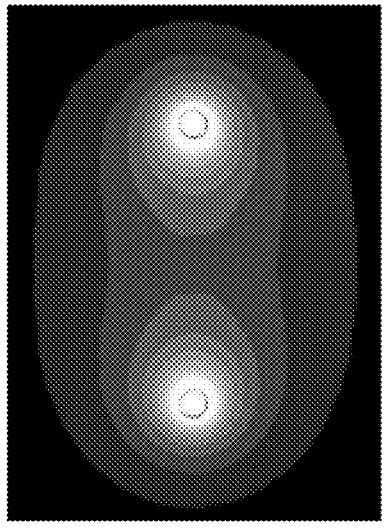
FIG. 24A
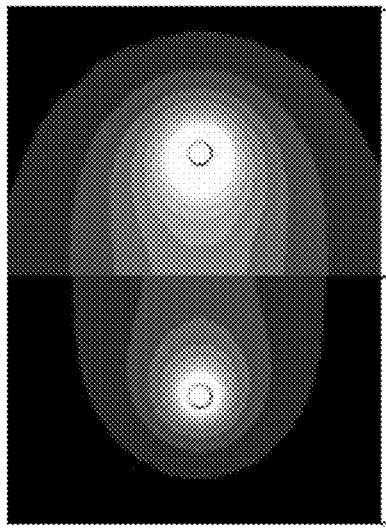
FIG. 24B
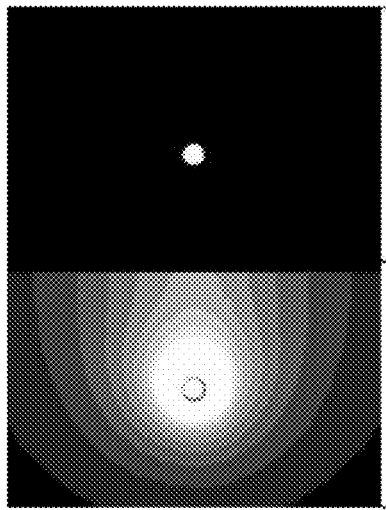
FIG. 24C
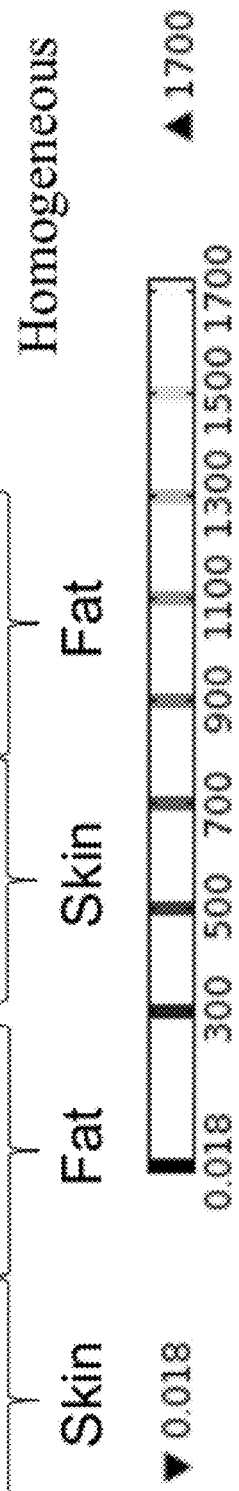

FIG. 25

Table 1. Conductivity of skin and fat as a function of frequency.

| Frequency | Waveform | Property | Tissue | |
|---|---|---|---|---|
| | | | Skin | Fat |
| 250 kHz | | $\sigma$ [S/m] | 0.00216 | 0.0263 |
| | | $\varepsilon_r$ | 888 | 47 |
| 500 kHz | | $\sigma$ [S/m] | 0.00485 | 0.0265 |
| | | $\varepsilon_r$ | 851 | 33 |
| 1 MHz | | $\sigma$ [S/m] | 0.0119 | 0.0267 |
| | | $\varepsilon_r$ | 792 | 25 |
| 2 MHz | | $\sigma$ [S/m] | 0.0290 | 0.0270 |
| | | $\varepsilon_r$ | 700 | 20 |

HIGH-FREQUENCY ELECTROPORATION FOR CANCER THERAPY

CROSS-REFERENCE TO RELATED APPLICATIONS

The present application relies on and claims priority to and the benefit of the filing date of U.S. Provisional Patent Application No. 61/424,872 filed Dec. 20, 2010 and International Patent Application No. PCT/US11/66239, filed Dec. 20, 2011; and the present application is a Continuation-In-Part (CIP) application of U.S. patent application Ser. No. 12/757,901, filed Apr. 9, 2010, which relies on and claims priority to and the benefit of the filing date of U.S. Provisional Patent Application Nos. 61/167,997, filed Apr. 9, 2009 and 61/285,618 filed Dec. 11, 2009. The entire disclosures of all of these patent applications are hereby incorporated herein by reference.

STATEMENT OF GOVERNMENT INTEREST

This invention was made with government support under Contract No. CBET-0933335 awarded by National Science Foundation. The government has certain rights in the invention.

BACKGROUND OF THE INVENTION

Field of the Invention

The present invention relates to the field of biomedical engineering and medical treatment of diseases and disorders. More specifically, embodiments of the invention relate to a device and method for destroying aberrant cells, including tumor tissues, using high-frequency, bipolar electrical pulses having a burst width on the order of microseconds and duration of single polarity on the microsecond to nanosecond scale.

Description of Related Art

Electroporation based therapies typically involve delivering multiple, unipolar pulses with a short duration (~100 μs) through electrodes inserted directly into, or adjacent to, the target tissue. See Nuccitelli, R., X. Chen, A. G. Pakhomov, W. H. Baldwin, S. Sheikh, J. L. Pomicter, W. Ren, C. Osgood, R. J. Swanson, J. F. Kolb, S. J. Beebe, and K. H. Schoenbach, *A new pulsed electric field therapy for melanoma disrupts the tumor's blood supply and causes complete remission without recurrence.* Int J Cancer, 2009. 125(2): p. 438-45; Davalos, R. V., L. M. Mir, and B. Rubinsky, *Tissue ablation with irreversible electroporation.* Ann Biomed Eng, 2005. 33(2): p. 223-31 ("Davalos 2005"); Payselj, N., V. Preat, and D. Miklavcic, *A numerical model of skin electroporation as a method to enhance gene transfection in skin.* 11th Mediterranean Conference on Medical and Biological Engineering and Computing 2007, Vols 1 and 2, 2007. 16(1-2): p. 597-601 ("Payselj 2007"); and Payselj, N., Z. Bregar, D. Cukjati, D. Batiuskaite, L. M. Mir, and D. Miklavcic, *The course of tissue permeabilization studied on a mathematical model of a subcutaneous tumor in small animals.* Ieee Transactions on Biomedical Engineering, 2005. 52(8): p. 1373-1381.

The extent of electroporation is attributed to the induced buildup of charge across the plasma membrane, or transmembrane potential (TMP). See Abidor, I. G., V. B. Arakelyan, L. V. Chernomordik, Y. A. Chizmadzhev, V. F. Pastushenko, and M. R. Tarasevich, *Electric Breakdown of Bilayer Lipid-Membranes .1. Main Experimental Facts and Their Qualitative Discussion.* Bioelectrochemistry and Bioenergetics, 1979. 6(1): p. 37-52; Benz, R., F. Beckers, and U. Zimmermann, *Reversible electrical breakdown of lipid bilayer membranes: a charge-pulse relaxation study.* J Membr Biol, 1979. 48(2): p. 181-204; Neumann, E. and K. Rosenheck, *Permeability changes induced by electric impulses in vesicular membranes.* J Membr Biol, 1972. 10(3): p. 279-90; Teissie, J. and T. Y. Tsong, *Electric-Field Induced Transient Pores in Phospholipid-Bilayer Vesicles.* Biochemistry, 1981. 20(6): p. 1548-1554; Zimmermann, U., G. Pilwat, and F. Riemann, *Dielectric breakdown of cell membranes.* Biophys J, 1974. 14(11): p. 881-99; and Kinosita, K. and T. Y. Tsong, *Formation and Resealing of Pores of Controlled Sizes in Human Erythrocyte-Membrane.* Nature, 1977. 268(5619): p. 438-441.

Once the TMP reaches a critical voltage, it is thought that permeabilizing defects, or pores, form in the plasma membrane in attempt to limit further TMP rise. Pore formation can either be reversible to allow for the introduction of foreign particles into viable cells, or irreversible to promote cell death through a loss of homeostasis. Known devices and methods of performing electroporation clinically involve several drawbacks, including painful muscle contractions, unpredictable treatment outcomes, and a high potential for thermal damage in low passive conductivity tissues.

IRE performed with unipolar pulses causes intense muscle contractions. Therefore, clinical applications of IRE require the administration of general anesthesia and neuroparalytic agents in order to eliminate the discomfort caused by muscle contractions seen during each pulse. See Talele, S. and P. Gaynor, *Non-linear time domain model of electropermeabilization: Response of a single cell to an arbitrary applied electric field.* Journal of Electrostatics, 2007. 65(12): p. 775-784. Receiving paralytic agents is undesirable for patients, and may deter them from seeking an electroporation based therapy. Further, in some cases, even with an adequate neuromuscular blockade, muscle contractions are still visible (see Payselj 2007), and questions remain as to what constitutes an appropriate dosage. Muscle contractions may affect the location of implanted needle electrodes, which can invalidate treatment planning algorithms. Additionally, in treatments near vital structures, displacement of the implanted electrodes may cause unavoidable collateral damage.

The time course of the pulsed electric field and dielectric properties of the tissue control the TMP development and the extent to which the transient defects form and reseal within the membrane. Knowledge of these two components can be used to predict treatment outcomes. However, predictions are complicated in heterogeneous tissues, or organs with multiple types of parenchymal tissue. There is often an intricate and unknown geometrical arrangement between tissues of low and high electrical conductivity, and the conductivity can change in real-time due to the phenomenon of electroporation, the extent of which is highly unpredictable without prior knowledge.

Low conductivity tissues, such as epithelial layers, often contain a dense packing of cells with reduced extracellular current pathways. As such, the resistance of the extracellular space is increased. Additionally, when pulses much longer than the charging time of the plasma membrane (~1 μs) are applied (see T. R., A. T. Esser, Z. Vasilkoski, K. C. Smith, and J. C. Weaver, *Microdosimetry for conventional and supra-electroporation in cells with organelles.* Biochem Biophys Res Commun, 2006. 341(4): p. 1266-76, "Gowrishankar 2006"), the current is confined to the extracellular space prior to the onset of electroporation, as shown in FIGS. 1A-B. As shown, when the pulse duration ($t_d$) is much less than the plasma membrane time constant ($\tau_{pm}$), current flows through both intracellular and extracellular spaces (FIG. 1A). In the case that $t_d$ is much greater than $\tau_{pm}$, current flow is restricted to the narrower extracellular spaces (FIG. 1B). Consequently, there is a large voltage drop across tissues with low conductivity, which increases the potential for deleterious Joule heating effects, such as thermal damage.

SUMMARY OF THE INVENTION

The present invention provides advancements over conventional tissue electroporation by utilizing high-frequency, bipolar pulses. Pulsing protocols according to embodiments of the invention involve bursts of bipolar pulses with a burst width on the order of microseconds and duration of single polarity on the microsecond to nanosecond scale, as shown in FIG. 2. The total burst width of the high-frequency pulses (~100-1000 ns duration of single polarity) is on the order of hundreds of microseconds, the time delay in between bursts is on the order of seconds, and the total number of bursts can be adjusted.

It is possible for the electric field to penetrate tissue heterogeneities when high-frequency electric fields are employed, because capacitive coupling is enhanced allowing current to flow through both extracellular and intracellular spaces. See Gowrishankar, T. R. and J. C. Weaver, *An approach to electrical modeling of single and multiple cells*. Proceedings of the National Academy of Sciences of the United States of America, 2003. 100(6): p. 3203-3208; and Ivorra, A., ed. *Tissue Electroporation as a Bioelectric Phenomenon: Basic Concepts*. Irreversible Electroporation, ed. B. Rubinsky. 2010, Springer Berlin Heidelberg. 23-61. In this case, all cells present in the organ, regardless of their packing and morphology, experience a macroscopically homogeneous electric field distribution. See Esser, A. T., K. C. Smith, T. R. Gowrishankar, and J. C. Weaver, *Towards Solid Tumor Treatment by Nanosecond Pulsed Electric Fields*. Technology in Cancer Research & Treatment, 2009. 8(4): p. 289-306. This results in more predictable and uniform treatment outcomes without the electric energy being preferentially deposited into regions of tissue with a lower passive conductivity. As a result, Joule heating is also more uniformly distributed throughout the tissue, which mitigates the potential for thermal damage in regions with a low passive conductivity.

Enhanced capacitive coupling also limits the change in tissue electrical conductivity due to electroporation. Therefore, prior knowledge of how the conductivity of a tissue is modulated in response to electroporation is not required to accurately predict the electric field distribution. As a result, simplified algorithms can be implemented for treatment planning.

High-frequency, bipolar waveforms are also included in embodiments of the invention for mitigating or completely eliminating muscle contractions during electroporation based therapies. It is well known in the field of functional electrical stimulation that the threshold for nerve stimulation increases as the center frequency of bipolar waveforms increases. Further, muscle twitch forces are reduced as frequency increases. The present invention demonstrates that a range of frequencies exist where non-thermal tissue ablation can be achieved without causing nerve excitation or muscle contraction. In the context of this specification, it is noted that the term ablation is used to indicate destruction of cells, but not necessarily destruction of the supportive stroma.

Clinically, this translates to performing IRE without the requirement of paralytic agents (or a reduction in the amount of paralytic agents administered) in all procedures, and without the further requirement of general anesthesia in minimally invasive procedures. Additionally, other complications caused by IRE with unipolar electric pulses are alleviated, including electrode displacement and pain associated with intense muscle contractions.

Examples of heterogeneous systems include, but are not limited to, tumors surrounded by or containing any type of epithelial layer, such as a skin fold geometry, or systems comprised of multiple tissue types including, brain, bone, breast, pancreatic, kidney, or lung. In this specification, an epithelial layer is defined as a dense packing of cells that restrict the flow of materials (e.g., electrical current) resulting in a low passive electrical conductivity.

The present invention applies to all electroporation based therapies. Recently, electroporation has been utilized in vivo as a means to destroy cancer cells within tissues in both reversible and irreversible modalities. Reversible electroporation is being studied to facilitate the delivery of anticancer drugs and DNA into cancer cells through the plasma membrane in the form of electrochemotherapy (ECT) and electrogenetherapy (EGT), respectively. Irreversible electroporation (IRE) promotes cell death resulting in the development of a tissue lesion. It is an independent means to ablate substantial volumes of targeted tissue without the use of harmful adjuvant chemicals if used prior to the onset of thermal injury. See Davalos 2005. By not relying on thermal processes, IRE has been shown to spare the extracellular matrix and architecture of nerves and blood vessels.

More specifically, the present invention provides new devices and methods for the treatment of diseases and disorders, such as hemic and solid neoplasias, which improves conventional clinical practice associated with electroporating target tissues.

Included in embodiments of the invention is a method of treating a subject suffering from a neoplasia comprising: implanting at least one device for emitting electric pulses into or adjacent a neoplastic site within the body of a subject; and delivering one or more electric pulse to the neoplastic site, such that amplitude and duration of the pulse are in the range of about 1500 V/cm to 2500 V/cm for 10 µs or less which is capable of inducing irreversible electroporation. Methods of the invention also include non-invasive methods of treating a subject comprising non-invasively placing at least one device for emitting electric pulses around a region of the body containing a neoplastic site within; and delivering one or more electric pulse, such that amplitude and duration of the pulse are in the range of about 1500 V/cm to 2500 V/cm for 10 µs or less which is capable of inducing irreversible electroporation.

According to embodiments of the invention, such methods can employ multiple pulses administered in a pulse burst having a duration of less than 10 ms.

Such methods can employ one or more pulses or a plurality of pulses in a pulsing protocol, wherein the amplitude of the pulse is in the range of about 500 V/cm to 1500 V/cm. Amplitude in the context of this specification refers to the voltage-distance ratio of a pulse, such as for 1500 V/cm the voltage is 750V over a distance of 0.5 cm.

Such methods can have a pulse duration in the range of about 2 MHz (250 ns) to about 500 kHz (1 µs). For example, the pulse duration can be about 1 MHz (500 ns). In preferred embodiments, the duration of each pulse is in the range of about 100 to 10,000 ns.

Any number of probes or electrodes can be used invasively, semi-invasively, or non-invasively according to embodiment of the invention. In preferred embodiments, two or more electrically conductive regions are used within a single device for emitting the electrical pulses. Similarly, in any of the methods according to the invention, two or more devices can be used to deliver multiple electric pulses at different positions within, on, or near a body.

Custom treatment area shapes can be created through varying electrode activation patterns in combination with any of the embodiments of the invention.

The methods can also employ delivery of a bipolar burst of pulses. In embodiments, a bipolar burst of pulses can be delivered with multiple pulses in a single phase before a polarity switch. Even further, total burst width of any pulse protocol according to the invention can be between 1 μs and 10,000 μs. In preferred embodiments, the methods can have a duration of single polarity within a bipolar burst of between about 100 ns and 100,000 ns.

The shape of the electric pulses delivered using methods of the invention can be square, ramp, sinusoidal, exponential, or trapezoidal.

In preferred embodiments, two or more electric pulse bursts can be administered with a delay between bursts. In preferred embodiments, a delay between bursts can be on the order of seconds. For example, in bipolar protocols a selected positive voltage (+V) can be applied for a selected period of time (e.g., 50 μs), then a zero voltage applied for a selected period of time (e.g., 75 μs), then a negative voltage (−V) can be applied (e.g., 50 μs). The voltage can be applied in any number of individual pulses, as a pulse or pulse burst.

Also included in embodiments of the invention is a method of delivering electric pulses such that amplitude and duration of single polarity are selected to be capable of administering electroporation to electrically excitable tissue without stimulation of the tissue.

Further included is a method of delivering electric pulses such that amplitude and duration of single polarity are selected to be capable of administering electroporation to electrically excitable tissue with reduced stimulation of the tissue as compared with higher amplitude and longer duration pulse protocols. Preferably tissue stimulation that is avoided or prevented refers to a muscle contraction.

In embodiments, the neoplastic site, region of the body, or electrically excitable tissue can be nerve tissue, muscle, or an organ containing nerves and/or muscle tissue.

Any embodiment of the invention can employ applying electric pulses having an amplitude and duration in the range of about 1500 V/cm to 2500 V/cm for 10 ms or less which is capable of inducing irreversible electroporation.

Method embodiments of the invention can be used to build up the transmembrane potential of a tissue to a critical value (~1V) by delivering trains of less than 1 μs bipolar pulses. For example, multiple monopolar pulses can be delivered at a pulse duration of about 5 MHz prior to a polarity switch, then delivered at a pulse duration of about 5 MHz after polarity switch.

Methods of the invention may or may not employ administering of a drug designed to induce a neural blockade. The methods can include administration of general, local, or no anesthesia for treatment of tissues with electroporation based therapies. In preferred embodiments, no neural blockade is required for treatment of tissues with electroporation based therapies, or lower dosages of a neural blockade can be used in embodiments of the invention to achieve the same results as using higher doses with lower frequency pulsing protocols.

The pulses of any method of the invention can be delivered on a short enough timescale to flow through epithelial cells but are long enough to induce electroporation in underlying cells. In specific embodiments, a frequency of 500 kHz or 1 MHz or 250 kHz is used to treat underlying fat cells in a layer of fat disposed under the epidermis.

Methods according to the invention can be modified to provide for administering non-thermal IRE, IRE, and/or reversible electroporation.

Treatment planning according to embodiments of the invention can result in more predictable outcomes in homogeneous and heterogeneous tissues than compared with lower frequency pulsing protocols.

Any one or more of the methods, devices, or systems, or parts thereof, can be combined with other methods, devices, systems, or parts thereof mentioned in this specification to obtain additional embodiments within the scope of this invention.

Devices and systems for implementing any one or more of the above mentioned methods are also within the scope of the invention.

BRIEF DESCRIPTION OF THE DRAWINGS

The accompanying drawings illustrate certain aspects of some of the embodiments of the present invention, and should not be used to limit the invention. Together with the written description the drawings serve to explain certain principles of the invention.

FIGS. 3A-D are graphs showing dielectric properties ($\sigma$ and $\varepsilon_r$) as a function of frequency for skin and fat.

FIGS. 4A-B are graphs showing respectively 2 MHz AC burst with a width of 4 μs, and a DC pulse with a duration of 4 μs of equal amplitude (FIG. 4A); and magnitude spectrum of the AC burst (thick) and DC pulse (thin) (FIG. 4B).

FIGS. 10A-B are graphs showing temperature changes predicted by the FEM at the center of the skin (FIG. 10A) and fat (FIG. 10B) for various frequencies of 250 kHz (- -), 500 kHz ( - - -), 1 MHz ( . . . ), and 2 MHz (-).

FIG. 15A-C are waveforms of IRE with unipolar pulses and high-frequency IRE with the corresponding TMP development across the plasma membrane ($\Phi_{pm}$) for a 1500 V/cm unipolar pulse (FIG. 15A) and a 1500 V/cm bipolar burst without a delay (FIG. 15B) and with a delay (FIG. 15C).

FIGS. 20A-D are micrographs showing the histopathology of rat brain tissue for untreated rats (FIGS. 20A-B) and treated with high-frequency, bipolar pulses at 200 V/250 kHz (FIG. 20C-D, Rat #2, right hemisphere), with the delineation between treated and untreated tissue shown in FIG. 20C (black, dotted line).

FIGS. 21A-F are MRIs of lesions in rat brain appearing as focal hyper-intense regions (white) compared to adjacent untreated cerebrocortical tissue (gray). FIGS. 21A-C were obtained from Rat #3, in which both the left and right cerebral hemispheres were treated with high-frequency waveforms at 300 V/250 kHz and 400 V/250 kHz, respectively. FIGS. D-F were obtained from Rat #4, which underwent high-frequency, bipolar pulses in the right cerebrum at 400 V/500 kHz, and conventional IRE with unipolar pulses at 50 V in the left cerebrum.

FIGS. 22A-D are data recordings of acceleration (a) versus time during treatments with unipolar IRE pulses and high-frequency IRE pulses.

FIGS. 24A-C are schematic diagrams showing electric field, norm (V/cm) contours predicted by the FEM during a 1000 V amplitude burst with a center frequency of 1 kHz (FIG. 24A) and 1 MHz (FIG. 24B). In FIG. 24C, the homogeneous solution is shown for a constant pulse.

FIG. 25 is a table showing conductivity of skin and fat as a function of frequency.

DETAILED DESCRIPTION OF VARIOUS EMBODIMENTS OF THE INVENTION

Figure 1:
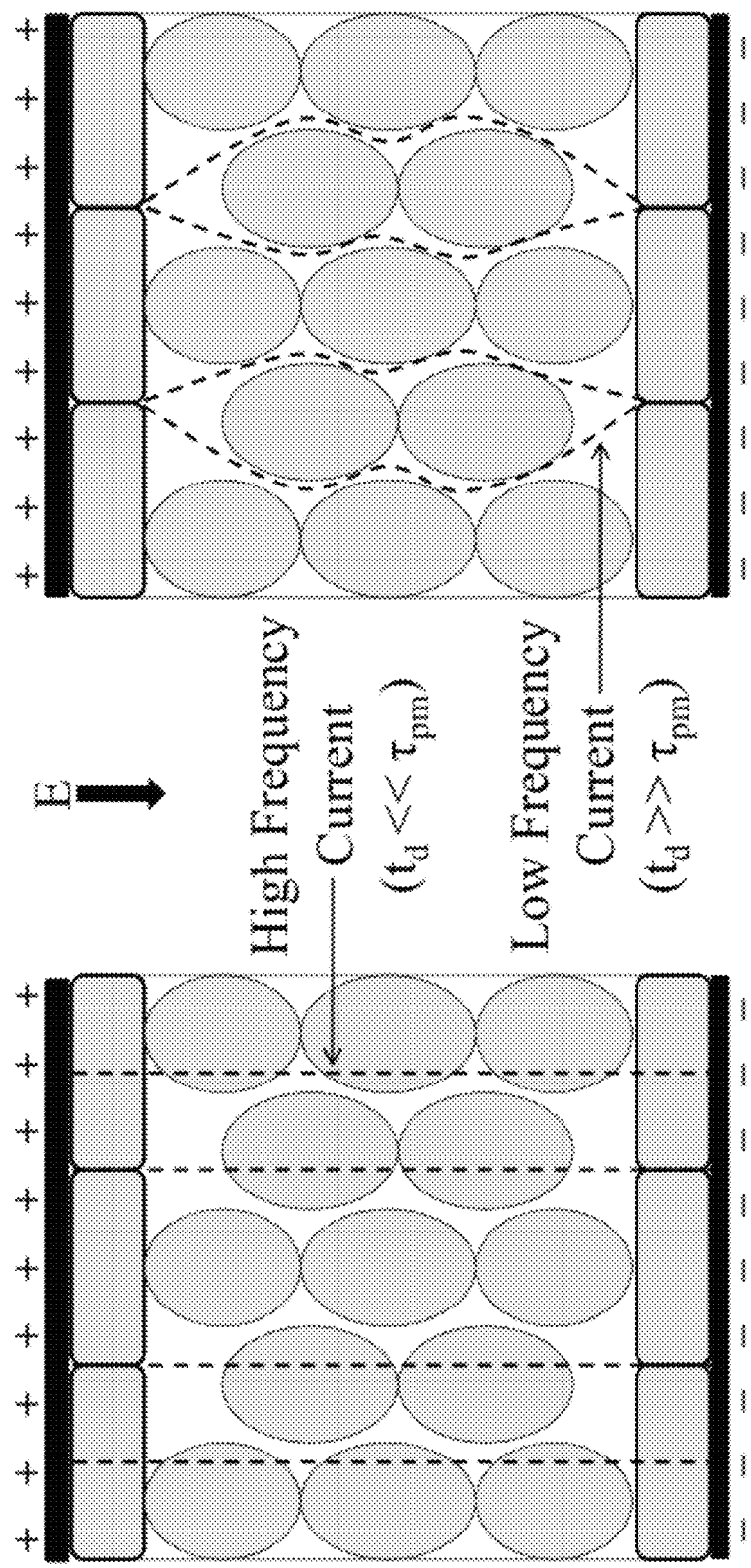
FIGS. 1A-B are schematic illustrations showing electrical current pathways through epithelial layers and bulk tissue prior to the onset of electroporation.
Figure 2:
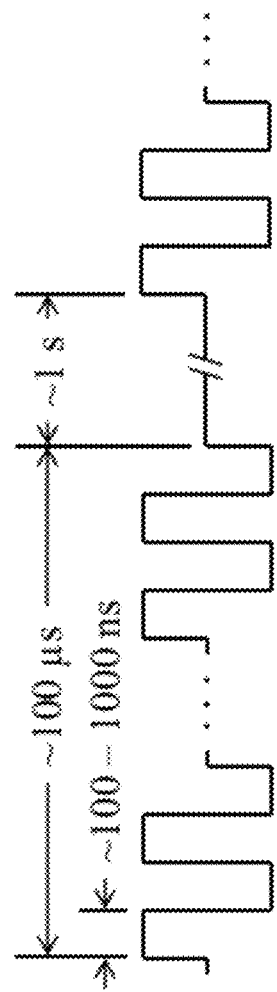
FIG. 2 is a schematic diagram of a representative pulsing protocol for electroporation based therapy according to embodiments of the present invention.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Despite being a well-known technique, there is significant controversy about the mechanisms governing electroporation. Weaver, J. C., *Electroporation of cells and tissues*. IEEE Transactions on Plasma Science, 2000. 28(1): p. 24-33. Even though the biophysical phenomenon at the molecular level is not known, the hypothesis is that in the presence of an externally applied electric field, the lipid bilayer in cellular membranes rearranges to create water-filled structures. These structures (or pores) provide a pathway for ions and molecules through the membranes that normally are impermeable. The dynamics of membrane poration is considered a four-step process: pore induction, expansion, stabilization and resealing. Weaver, J. C. and Y. A. Chizmadzhev, *Theory of electroporation: a review*. Bioelectrochem. Bioenerg., 1996. 41: p. 135-60. Initial thermal fluctuations are responsible for the presence of hydrophobic pores. There exists a critical radius where it is more energetically favorable for a hydrophobic pore to transition to a hydrophilic pore. In addition, increasing the TMP reduces this critical radius and increases the stability of a hydrophilic pore. Kinosita, K., Jr., S. Kawato, and A. Ikegami, *A theory of fluorescence polarization decay in membranes*. Biophys J, 1977. 20(3): p. 289-305. When the pore reaches this metastable state, it becomes permeable to small molecules. The presence of the induced transmembrane potential lowers the energy required for the pore's existence. Freeman, S. A., M. A. Wang, and J. C. Weaver, *Theory of Electroporation of Planar Bilayer-Membranes—Predictions of the Aqueous Area, Change in Capacitance, and Pore-Pore Separation*. Biophysical Journal, 1994. 67(1): p. 42-56. When the electric field has been turned off, the membrane starts to return to its normal membrane potential and resealing of the pores takes place.

The dielectric permittivity and conductivity of a given tissue are typically functions of frequency. A comparison of the dielectric properties between skin and fat is presented in Table 1. This data was obtained by interpolating the results from Gabriel et al. (FIGS. 3A-D). Gabriel, S., R. W. Lau, and C. Gabriel, *The dielectric properties of biological tissues .2. Measurements in the frequency range 10 Hz to 20 GHz*. Physics in Medicine and Biology, 1996. 41(11): p. 2251-2269. At varying frequencies, different mechanisms of charge transfer contribute differently to the permittivity and conductivity. Stoy, R. D., K. R. Foster, and H. P. Schwan, *Dielectric properties of mammalian tissues from 0.1 to 100 MHz: a summary of recent data*. Phys Med Biol, 1982. 27(4): p. 501-13.

In general, as the frequency increases, so does the conductivity of the skin and fat. According to Table 1 (FIG. 25), the difference in conductivity between skin (s) and fat (f) is reduced as the frequency increases from 250 kHz to 2 MHz ($\sigma s/\sigma f \sim 1$).

Therefore, if electroporation is used to treat a tumor within a heterogeneous skin fold geometry, the electric field distribution in the surrounding skin and fat would be more homogenous if high-frequency waveforms are utilized. Oftentimes tissue impedance has patient-to-patient variability and the impedance distribution and any impedance changes may be difficult to determine for a particular patient. This point is emphasized further in EXAMPLE 1. Because rectangular waveforms are comprised of components with various frequencies and amplitudes, tissue properties at frequencies associated with the center frequency, defined as the inverse of twice the duration of single polarity, are chosen when studying AC bursts. This is illustrated in FIGS. 4A-B. By taking the absolute value of the Fourier Transform of an AC burst and a DC pulse, the magnitude spectrum can be obtained. While the DC pulse transmits a majority of its power at low frequencies (0 Hz), the AC burst has a characteristic peak at the center frequency (2 MHz in this case).

The benefits of bipolar pulses have been studied for electroporation applications at the single-cell level. Theoretically, Talele et al. have shown that asymmetrical electroporation due to the resting TMP (~0.1 V) (see Gowrishankar 2006) of cells seen when unipolar pulses are delivered (see Chang, D. C., *Cell Poration and Cell-Fusion Using an Oscillating Electric-Field*. Biophysical Journal, 1989. 56(4): p. 641-652, "Chang 1989"; and Tekle, E., R. D. Astumian, and P. B. Chock, *Electroporation by Using Bipolar Oscillating Electric-Field—an Improved Method for DNA Transfection of Nih 3t3 Cells*. Proceedings of the National Academy of Sciences of the United States of America, 1991. 88(10): p. 4230-4234, "Tekle 1991") can be alleviated by switching to bipolar pulses. Talele, S. and P. Gaynor, *Non-linear time domain model of electropermeabilization: Response of a single cell to an arbitrary applied electric field*. Journal of Electrostatics, 2007. 65(12): p. 775-784. Experimentally, this leads to increased efficiency of macromolecule uptake through the membrane. Chang 1989; and Tekle 1991. Depending on the extracellular conductivity, bipolar pulses with a frequency of 1 MHz (i.e. 500 ns duration of single polarity) can also lessen the dependence of electroporation on cell size, allowing more cells to be electroporated. Talele, S. and P. Gaynor, *Non-linear time domain model of electropermeabilization: Effect of extracellular conductivity and applied electric field parameters*. Journal of Electrostatics, 2008. 66(5-6): p. 328-334; and Talele, S., P. Gaynor, M. J. Cree, and J. van Ekeran, *Modelling single cell electroporation with bipolar pulse parameters and dynamic pore radii*. Journal of Electrostatics, 2010. 68(3): p. 261-274. In general, pore formation increases as long as the TMP is sustained above a critical threshold (~1 V). Gowrishankar 2006. Bipolar pulses require higher field strengths to induce a given TMP as compared to a unipolar pulse of equivalent duration. This is accentuated when the frequency of the bipolar pulses is increased, because the time interval above the critical TMP is reduced. Talele, S., P. Gaynor, M. J. Cree, and J. van Ekeran, *Modelling single cell electroporation with bipolar pulse parameters and dynamic pore radii*. Journal of Electrostatics, 2010. 68(3): p. 261-274. Kotnik et al. have explored the benefits of bipolar pulse trains at significantly lower frequencies, up to 1 kHz (i.e. 500 μs duration of single polarity). At lower frequencies, theoretical results show that the pore formation symmetry can also be normalized with bipolar pulses. Kotnik, T., L. M. Mir, K. Flisar, M. Puc, and D. Miklavcic, *Cell membrane electropermeabilization by symmetrical bipolar rectangular pulses. Part I. Increased efficiency of permeabilization*. Bioelectrochemistry, 2001. 54(1): p. 83-90, "Kotnik I 2001." Experimentally, bipolar pulses reduce electrolytic contamination (see Kotnik, T., D. Miklavcic, and L. M. Mir, *Cell membrane electropermeabilization by symmetrical bipolar rectangular pulses. Part II. Reduced electrolytic contamination*. Bioelectrochemistry, 2001. 54(1): p. 91-5) and the required field strength for reversible electroporation, while the field strength required for IRE remains unchanged. Kotnik I 2001. The authors attribute this to the fact that when the duration of single polarity is much longer than the plasma membrane charging time, permeabilized area differences on the membrane between unipolar and bipolar pulses decreases as pulse amplitude increases.

Bipolar pulse delivery has been studied in vivo for reversible applications of electroporation using center frequencies that are two orders of magnitude lower than that used in embodiments of the present invention. Daskalov et al. have demonstrtated that pulses delivered at 1 kHz are associated with less patient pain in during electrochemotherapy. Daskalov, I., N. Mudrov, and E. Peycheva, *Exploring new instrumentation parameters for electrochemotherapy—Attacking tumors with bursts of biphasic pulses instead of single pulses*. IEEE Eng Med Biol Mag, 1999. 18(1): p. 62-66. Similarly, Nikolova et al. has recently demonstrated the same findings during electrochemotherapy with a *Bacillus* Calmette-Guerin vaccine. Nikolova, B., I. Tsoneva, and E. Peycheva, *Treatment of Melanoma by Electroporation of Bacillus Calmette-Guerin*. Biotechnology & Biotechnological Equipment, 2011. 25(3): p. 2522-2524. Both authors attribute the reduction in patient pain due to the associated reduction in muscle contractions seen with bipolar pulses.

There is a balance between employing pulses that are delivered at a high enough frequency to reduce the conductivity mismatch between different tissues but have a duration of single polarity long enough to induce electroporation of cells comprising the tissues. As mentioned, electrical current associated with pulses longer than ~1 μs is confined to extracellular spaces prior to the onset of electroporation. Ivorra, A., ed. *Tissue Electroporation as a Bioelectric Phenomenon: Basic Concepts*. Irreversible Electroporation, ed. B. Rubinsky. 2010, Springer Berlin Heidelberg. 23-61; and Esser, A. T., K. C. Smith, T. R. Gowrishankar, and J. C. Weaver, *Towards solid tumor treatment by irreversible electroporation: intrinsic redistribution of fields and currents in tissue*. Technol Cancer Res Treat, 2007. 6(4): p. 261-74. This can be attributed to the migration of charges towards biological membranes following the application of an external electric field. The time required for a membrane to become charged to 63% of its steady state value is defined as the charging time constant of the membrane. Displacement currents across the plasma membrane allow organelles to be exposed to fields during the time that it takes the plasma membrane to reach steady state. Esser, A. T., K. C. Smith, T. R. Gowrishankar, and J. C. Weaver, *Towards Solid Tumor Treatment by Nanosecond Pulsed Electric Fields*. Technology in Cancer Research & Treatment, 2009. 8(4): p. 289-306. Once steady state is achieved, the counter-field developed along the plasma membrane due to the accumulation of charges is significant enough to shield the field from entering the cell, and current is directed through extracellular spaces. Only after permeabilization of the membrane does ionic conduction allow the field to re-enter the cell. Kolb, J. F., S. Kono, and K. H. Schoenbach, *Nanosecond pulsed electric field generators for the study of subcellular effects*. Bioelectromagnetics, 2006. 27(3): p. 172-187. If extracellular current pathways between cells are reduced, as in layers of epithelial cells connected by tight or gap junctions (see Jones, D. M., R. H. Smallwood, D. R. Hose, B. H. Brown, and D. C. Walker, *Modelling of epithelial tissue impedance measured using three different designs of probe*. Physiological Measurement, 2003. 24(2): p. 605-623), the field is highly concentrated across the layer, and the extent of electroporation in underlying cells is reduced. This problem is alleviated when the duration of single polarity approaches the membrane time constant.

By treating cells as a series of spherical, dielectric shells containing and surrounded by a conductive medium, the analytical solution for induced TMP across the plasma membrane (ΔΦ) can be obtained according to the law of total current (see Yao, C. G., D. B. Mo, C. X. Li, C. X. Sun, and Y. Mi, *Study of transmembrane potentials of inner and outer membranes induced by pulsed-electric-field model and simulation*. IEEE Trans Plasma Sci, 2007. 35(5): p. 1541-1549, "Yao 2007"):

$$\nabla \cdot \left(\varepsilon_0 \varepsilon_r \frac{\partial E}{\partial t} + \sigma E\right) = \Lambda_k \nabla \cdot E = 0 \quad (1)$$

$$\Lambda_k = \sigma + \varepsilon_0 \varepsilon_r \frac{\partial}{\partial t} \quad (2)$$

where $\Lambda$ is the admittivity operator and the subscript k denotes cellular regions including the nucleoplasm (n), nuclear envelop (ne), cytoplasm (c), plasma membrane (pm), and extracellular space (e). Transforming (2), (5), and (6) into the frequency domain (see Yao 2007):

$$E = -\nabla \Phi(s) \quad (3)$$

$$\Lambda_k \nabla \cdot E(s) = 0 \quad (4)$$

$$\Lambda_k(s) = \sigma + \varepsilon_0 \varepsilon_r s \quad (5)$$

where $s = j\omega = j2\pi f$, and applying the appropriate boundary conditions of potential continuity and normal vector continuity of current density at the interface between the different regions yields the solution for TMP (see Yao 2007):

$$\Delta \Phi(s) = F(\Lambda_n, \Lambda_{ne}, \Lambda_c, \Lambda_{pm}, \Lambda_e) E(s) \cos \theta \quad (6)$$

where θ represents the polar angle at the cell center between the electric field and the point of interest along the membrane. TMP is defined as the potential directly outside the membrane minus the inside. The natural, resting component of the plasma membrane TMP was ignored in all simulations, because it is typically an order of magnitude less than the induced TMP. See Gowrishankar 2006. Further, the TMP across the nuclear envelope never reached a permeabilizing threshold with the chosen pulsing protocols, and reference to TMP from this point forward refers only to the plasma membrane. As shown in Table 2, the term $F(\Lambda_k)$ represents a transfer function of the TMP that reflects the geometric and dielectric properties of the cellular regions as a function of the admittivity. See Hu, Q., S. Viswanadham, R. P. Joshi, K. H. Schoenbach, S. J. Beebe, and P. F. Blackmore, *Simulations of transient membrane behavior in cells subjected to a high-intensity ultrashort electric pulse*. Physical Review E, 2005. 71(3). Dielectric properties at the cellular level are assumed to be frequency independent, which is valid for predicting TMP up to around 100 MHz. Kotnik, T. and D. Miklavcic, *Theoretical evaluation of the distributed power dissipation in biological cells exposed to electric fields*. Bioelectromagnetics, 2000. 21(5): p. 385-394.

TABLE 2

Dielectric properties of various cellular regions.

| Geometry | σ [S/m] | $\varepsilon_r$ | Dimensions [m] |
|---|---|---|---|
| Extracellular Space | 0.6 | 80.0 | — |
| Plasma Membrane | $5.3 \times 10^{-6}$ | 7.0 | $7.0 \times 10^{-9}$ (thickness) |
| Cytoplasm | 0.13 | 60.0 | $5.0 \times 10^{-6}$ (radius) |
| Nuclear Envelope | $4.3 \times 10^{-3}$ | 22.8 | $40.0 \times 10^{-9}$ (thickness) |
| Nucleoplasm | 0.18 | 120.0 | $2.5 \times 10^{-6}$ (radius) |

The exact formulation for $F(\Lambda_k)$ is lengthy and can be found in (see Kotnik, T. and D. Miklavcic, *Theoretical evaluation of voltage inducement on internal membranes of biological cells exposed to electric fields*. Biophysical Journal, 2006. 90(2): p. 480-491), but is not included here for brevity. The term E(s) represents the Laplace transform of the pulsed electric field as a function of time.

Figure 5:
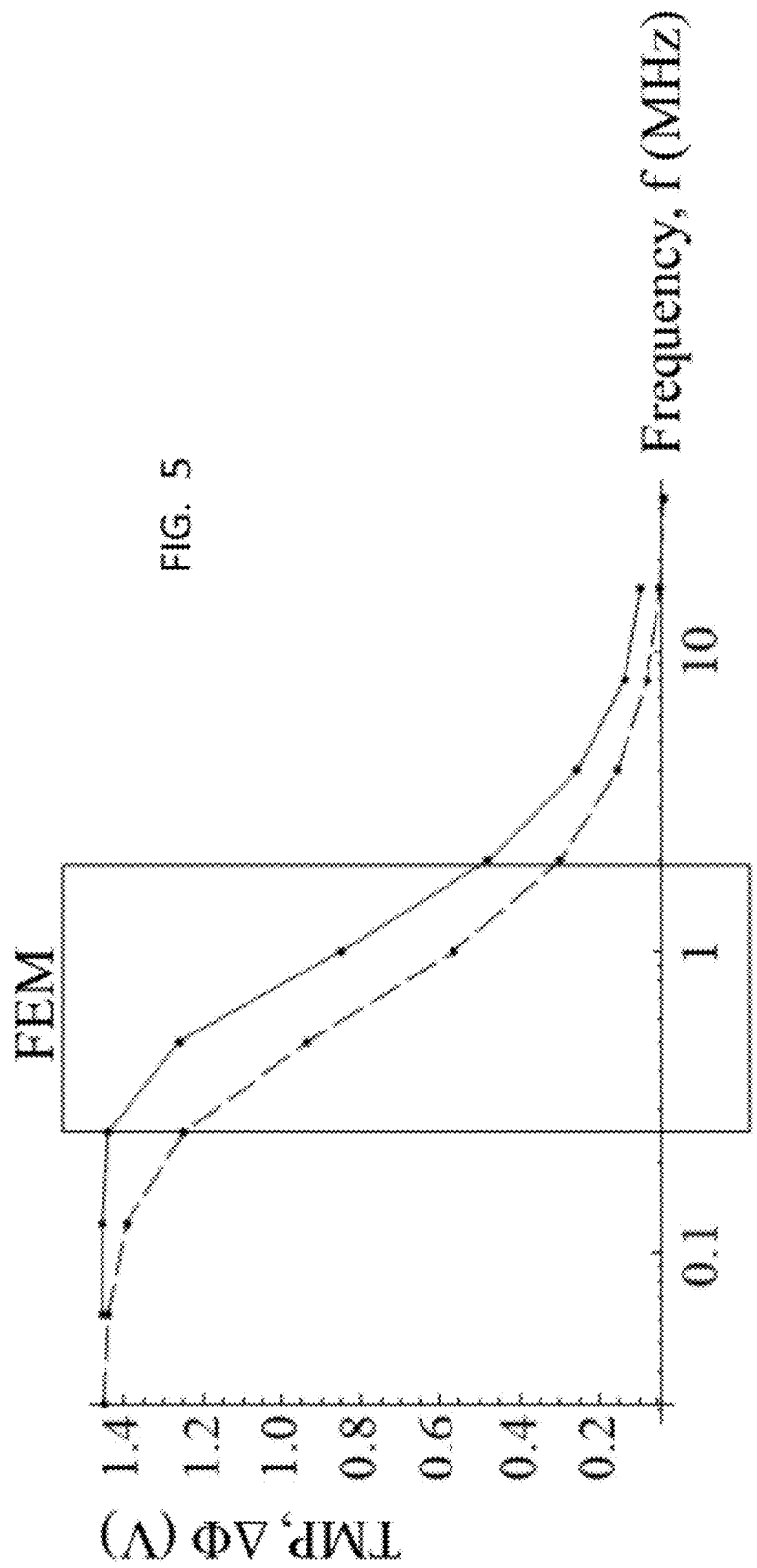
FIG. 5 is a graph showing frequency (f) response of the TMP at the cell pole ($\theta=0$) for rectangular bipolar pulses (-) and sinusoidal waveforms (- -). The box illustrates the frequency window implemented in the FEM.

Using the analytical model, the frequency dependence of the induced TMP can be investigated for both rectangular and sinusoidal electric fields with identical maximum amplitude. By substituting the transient electric fields into (6) the results of a parametric study on TMP for frequencies spanning from 62.5 kHz to 16 MHz are shown in FIG. 5. The maximum amplitude of the sinusoidal and bipolar rectangular electric fields was 2000 V/cm (peak). For this applied field and the given geometric and dielectric properties of the modeled cell, the TMP never exceeds 1.46 V. Additionally, the time constant of the plasma membrane is 345 ns. All measurement were taken at the cell pole (θ=0) to depict the maximum achieved TMP after the system reached a steady oscillatory state. From the curve, as the frequency increases, the magnitude of the TMP is reduced. For the sinusoidal waveform, the reduction is evident at lower frequencies compared to the rectangular waveform. This has to do with the fact that the rectangular waveform maintains its maximum amplitude for a longer period of time than the sinusoidal waveform. It is not until the frequency of the rectangular waveform surpasses 250 kHz that a dramatic decrease in TMP occurs. For this reason, only rectangular pulses in a frequency window of 250 kHz to 2 MHz are best suited for electroporation with high-frequency, bipolar pulses.

Based on the analytical model for TMP presented above, the time constant of the plasma membrane for a constant field (2000 V/cm) is 345 ns. The time constant of 345 ns falls between the 2 MHz (250 ns pulse duration) and 1 MHz (500 ns pulse duration) bursts. Further, the 500 kHz burst (1 μs pulse duration) is close to the time it takes the TMP to reach steady state. As frequency is increased, the dielectric properties different tissues become more macroscopically homogeneous, but above 2 MHz, the pulse duration is not adequate for the cell to charge and induce electroporation. According to in vitro experiments that utilize bipolar rectangular pulses, the typical burst width required to induce either reversible electroporation or IRE increases with the frequency of the applied field. For EGT, a 60 kHz bipolar square with a burst width of 400 μs and an amplitude of 1600 V/cm has a six times greater transfection efficiency than a 1 MHz bipolar square wave with equal amplitude and width. Tekle, E., R. D. Astumian, and P. B. Chock, *Electroporation by Using Bipolar Oscillating Electric-Field—an Improved Method for DNA Transfection of Nih 3t3 Cells*. Proceedings of the National Academy of Sciences of the United States of America, 1991. 88(10): p. 4230-4234 (Telke 1991). In terms of IRE, a 60 kHz bipolar square with a burst width of 400 μs and an amplitude of 4000 V/cm results in 19% cell viability. Telke 1991. These results were obtained when a single burst was delivered to the sample. The inventors, however, appear to be the first in providing data on high-frequency electroporation with rectangular pulses that implemented multiple bursts. Similar to how multiple unipolar pulses are typically delivered in ECT, EGT, or IRE protocols to enhance the desired outcome (see Belehradek, J., S. Orlowski, L. H. Ramirez, G. Pron, B. Poddevin, and L. M. Mir, *Electropermeabilization of Cells in Tissues Assessed by the Qualitative and Quantitative Electroloading of Bleomycin*. Biochimica Et Biophysica Acta-Biomembranes, 1994. 1190(1): p. 155-163; and Garcia, P. A., J. H. Rossmeisl, R. E. Neal, T. L. Ellis, J. D. Olson, N. Henao-Guerrero, J. Robertson, and R. V. Davalos, *Intracranial Nonthermal Irreversible Electroporation: In Vivo Analysis*. Journal of Membrane Biology, 2010. 236(1): p. 127-136) multiple bipolar bursts would likely produce similar trends. Data is also available for burst sinusoidal waveforms in the frequency range of 2 kHz to 50 MHz (see Jordan, D. W., R. M. Gilgenbach, M. D. Uhler, L. H. Gates, and Y. Y. Lau, *Effect of pulsed, high-power radiofrequency radiation on electroporation of mammalian cells*. Ieee Transactions on Plasma Science, 2004. 32(4): p. 1573-1578; and Katsuki, S., N. Nomura, H. Koga, H. Akiyama, I. Uchida, and S. I. Abe, *Biological effects of narrow band pulsed electric fields*. Ieee Transactions on Dielectrics and Electrical Insulation, 2007. 14(3): p. 663-668), but the results are inconclusive, and sinusoidal waveforms are less efficient than rectangular bipolar pulses for inducing electroporation. Kotnik, T., G. Pucihar, M. Rebersek, D. Miklavcic, and L. M. Mir, *Role of pulse shape in cell membrane electropermeabilization*. Biochimica Et Biophysica Acta-Biomembranes, 2003. 1614(2): p. 193-200.

There is a narrow window of pulse parameters where ECT and EGT have proven to be effective without reducing cell viability by IRE. For ECT, the field for inducing optimal reversible electroporation conditions is between 300 and 500 V/cm in tumors, when eight square-wave pulses 100 μs in duration are delivered at a frequency of 1 Hz. Mir, L. M., *Therapeutic perspectives of in vivo cell electropermeabilization*. Bioelectrochemistry, 2001. 53: p. 1-10 (Mir 2001). For EGT, permeabilization conditions are optimal when eight square-wave pulses 20 ms in duration are delivered at a frequency of 1 Hz, which constitutes a field of around 90 V/cm. Mir 2001. To maintain its non-thermal benefits, the pulse parameters for IRE procedures are restricted to those that minimize any associated Joule heating. Davalos, R. V. and B. Rubinsky, *Temperature considerations during irreversible electroporation*. International Journal of Heat and Mass Transfer, 2008. 51(23-24): p. 5617-5622. However, a similar field strength and duration to those required for ECT can induce IRE when the number of pulses is raised above the traditional 8 pulses to 90 pulses, and the temperature of the tissue remains below 50° C. Rubinsky, J., G. Onik, P. Mikus, and B. Rubinsky, *Optimal Parameters for the Destruction of Prostate Cancer Using Irreversible Electroporation*. Journal of Urology, 2008. 180(6): p. 2668-2674.

In addition to being bipolar, the pulses used according to methods of the invention can have a duration of single polarity (~1 μs) that is two orders of magnitude less than the duration of a conventional electroporation pulse (~100 μs) and an amplitude that is one order of magnitude less than supraporation protocols with nanosecond pulsed electric field (nsPEF). Supraporation involves pulses with a duration ranging from 1-100 ns and an amplitude ranging from 10-100 kV/cm. These electric fields are capable of causing electroporation within the membranes of intracellular organelles. Vernier, P. T., Y. H. Sun, and M. A. Gundersen, *Nanoelectropulse-driven membrane perturbation and small molecule permeabilization*. Bmc Cell Biology, 2006. 7. When the pulse length is shorter than the charging time of the plasma membrane, the field can penetrate the plasma membrane to reach the cell interior. Beebe, S. J., P. M. Fox, L. J. Rec, L. K. Willis, and K. H. Schoenbach, *Nanosecond, high-intensity pulsed electric fields induce apoptosis in human cells*. FASEB J, 2003. 17(9): p. 1493-5. Because organelles are smaller in diameter than cells, the amplitude required to raise the TMP on organelles up to ~1 V is greater than that in ECT and IRE procedures. However, due to the ultra-short nature of the pulses, the accompanying Joule heating is still negligible. Schoenbach, K. H., S. J. Beebe, and E. S. Buescher, *Intracellular effect of ultrashort electrical pulses*. Bioelectromagnetics, 2001. 22(6): p. 440-8. While immediate necrosis is suspected as the primary mechanism of cell death following IRE, apoptosis triggered by DNA fragmentation and the release of calcium from intracellular stores occurs in cells exposed to sufficiently high nsPEFs. Beebe, S. J., J. White, P. F. Blackmore, Y. P. Deng, K. Somers, and K. H. Schoenbach, *Diverse effects of nanosecond pulsed electric fields on cells and tissues*. DNA and Cell Biology, 2003. 22(12): p. 785-796.

Figure 6:
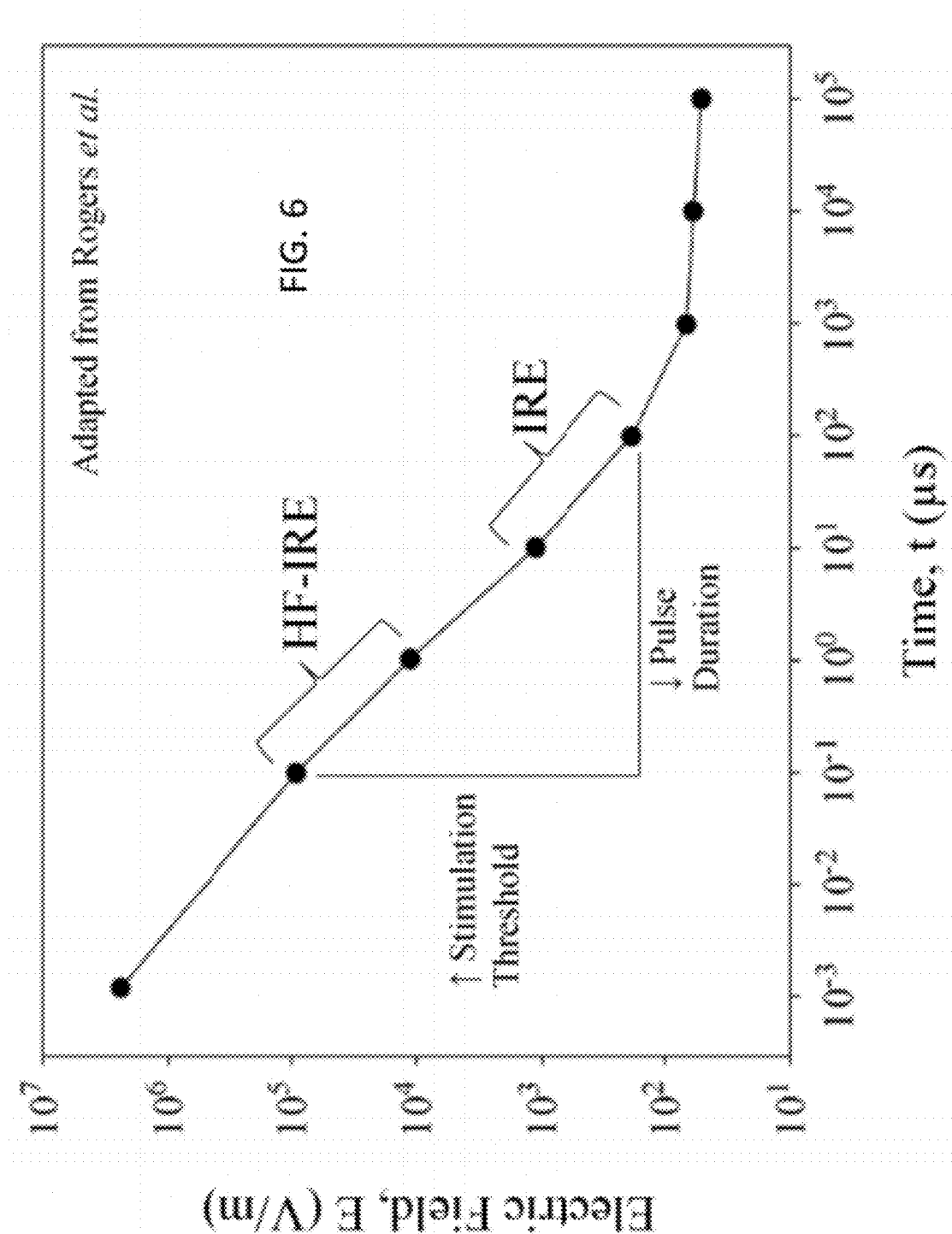
FIG. 6 is a graph of the strength-duration curve for unipolar electric pulses expressed as electric field strength in tissue. Adapted from Rogers, W. R., J. H. Merritt, J. A. Comeaux, C. T. Kuhnel, D. F. Moreland, D. G. Teltschik, J. H. Lucas, and M. R. Murphy, *Strength-duration curve for an electrically excitable tissue extended down to near 1 nanosecond*. Ieee Transactions on Plasma Science, 2004. 32(4): p. 1587-1599 ("Reilly 2004").

In vivo experiments on supraporation have shown that the ultra-short, unipolar pulses do not cause stimulation of excitable tissue, such as muscle and nerves. Long, G., P. K. Shires, D. Plescia, S. J. Beebe, J. F. Kolb, and K. H. Schoenbach, *Targeted Tissue Ablation With Nanosecond Pulses*. Ieee Transactions on Biomedical Engineering, 2011. 58(8). This is a consequence of the pulses being below the strength-duration threshold determined by Rogers et al. Rogers, W. R., J. H. Merritt, J. A. Comeaux, C. T. Kuhnel, D. F. Moreland, D. G. Teltschik, J. H. Lucas, and M. R. Murphy, *Strength-duration curve for an electrically excitable tissue extended down to near 1 nanosecond*. Ieee Transactions on Plasma Science, 2004. 32(4): p. 1587-1599. As seen in FIG. 6, for IRE pulses, the electric field threshold for stimulation is between 1-10 V/cm. The present invention describes pulses where the duration of single polarity is as low as 100 ns. At this duration, the electric field threshold for stimulation increases to 1000 V/cm, which is above the amplitude required for reversible electroporation and on the order of the amplitude for IRE.

Figure 7:
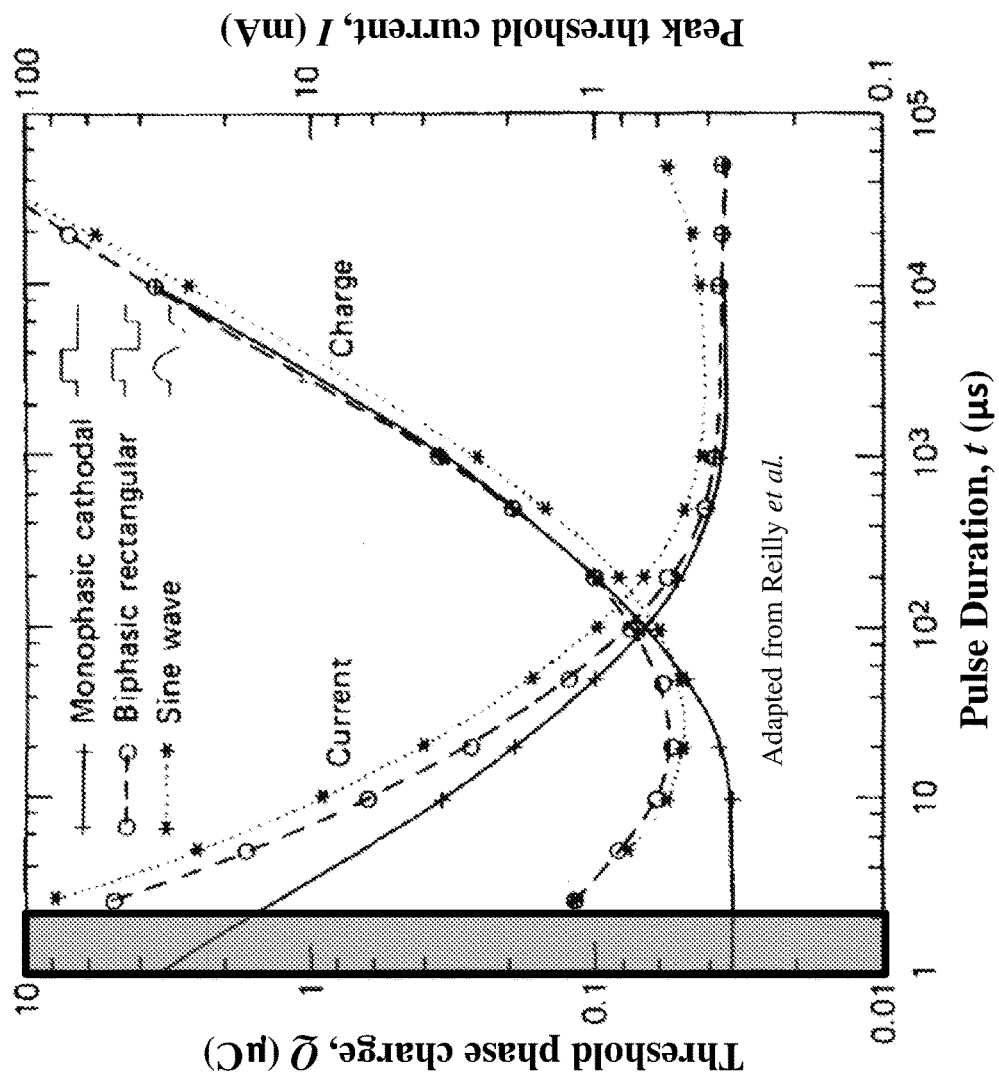
FIG. 7 is a strength-duration graph comparing unipolar to bipolar rectangular and sine waveforms expressed as phase charge and current. Adapted from Reilly 2004.

In addition to the duration of single polarity being reduced, the fact that the inventive waveforms are inherently bipolar offers an additional benefit in terms of the stimulation of excitable tissue. As shown in FIG. 7, biphasic waveforms have a higher threshold current for inducing nerve stimulation. Reilly, J. P., V. T. Freeman, and W. D. Larkin, *Sensory Effects of Transient Electrical-Stimulation—Evaluation with a Neuroelectric Model*. IEEE Trans Biomed Eng, 1985. 32(12): p. 1001-1011. Further, the threshold increases exponentially as the duration of single polarity is decreased. While the mechanism of this phenomenon is unknown, it is thought that the reversal in polarity prevents an action potential from being generated by limiting the flow of sodium ions down their concentration gradient. This has been shown to translate to a reduced muscle twitch force during bipolar functional electrical stimulation as opposed to monopolar. Vandenhonert, C. and J. T. Mortimer, *Response of the Myelinated Nerve-Fiber to Short Duration Biphasic Stimulating Currents*. Annals of Biomedical Engineering, 1979. 7(2): p. 117-125.

The inventors have shown that bipolar waveforms can induce IRE at center frequencies high enough to eliminate muscle contraction completely. This procedure is termed high-frequency IRE (H-FIRE). Overall, the results indicate that H-FIRE can produce more predictable treatment outcomes, reduce the potential for thermal damage, and obviate the need for (or reduce the necessity of) neuroparalytic agents delivered prior to or during treatment.

The following examples show that bursts of bipolar, nanosecond pulses can maintain a critical TMP beneath epithelial layers, while minimizing Joule heating. This has to do with the ability of high-frequency waveforms to achieve a macroscopically homogeneous field distribution in a heterogeneous system. At high-frequencies, tissues with a low passive DC conductivity become more conductive. Additionally, it is proven that high-frequency IRE (H-FIRE) can be applied to non-thermally ablate tissue while eliminating muscle contractions seen in conventional IRE protocols with longer duration unipolar pulses. These results have implications not only for skin, brain, and liver as presented here, but for other tissues, such as bone, breast, pancreas, kidney, and lung. These examples should not be considered as limiting the invention in any way.

As a general background to the examples, it is noted that the inventors and their colleagues have successfully demonstrated that finite element models (FEMs) can accurately predict treatment outcomes of pulsed electric field therapies for cancer treatment. See Edd, J. F. and R. V. Davalos, *Mathematical modeling of irreversible electroporation for treatment planning*. Technol Cancer Res Treat, 2007. 6: p. 275-286; and Edd, J. F., L. Horowitz, R. V. Davalos, L. M. Mir, and B. Rubinsky, *In vivo results of a new focal tissue ablation technique: irreversible electroporation*. IEEE Trans Biomed Eng, 2006. 53(7): p. 1409-15.

Example 1

High-frequency electroporation results in more uniform and predictable treatment outcomes in heterogeneous tissues.

A 2D axisymmetric FEM representative of a cylindrical section of non-infiltrated fat encapsulated by dry skin was simulated using COMSOL 3.5a (Burlington, Mass.). The electric potential distribution within the tissue was obtained by transiently solving:

$$-\nabla \cdot (\sigma \nabla \Phi) - \varepsilon_0 \varepsilon_r \nabla \cdot \left(\frac{\partial \nabla \Phi}{\partial t}\right) = 0 \qquad (7)$$

where $\Phi$ is the electric potential and $\sigma$ and $\varepsilon_r$ are the conductivity and relative permittivity of each tissue layer, respectively, which depends on frequency (Table 1). Equation (7) is obtained from Maxwell's equations assuming no external current density (J=$\sigma$E), no remnant displacement (D=$\varepsilon_0\varepsilon_r$E), and the quasi-static approximation. This approximation implies a negligible coupling between the electric and magnetic fields ($\nabla \times$E=0), which allows for the expression of electric field only in terms of electric potential:

$$E = -\nabla \Phi \qquad (8)$$

Figures 8A, 8B:
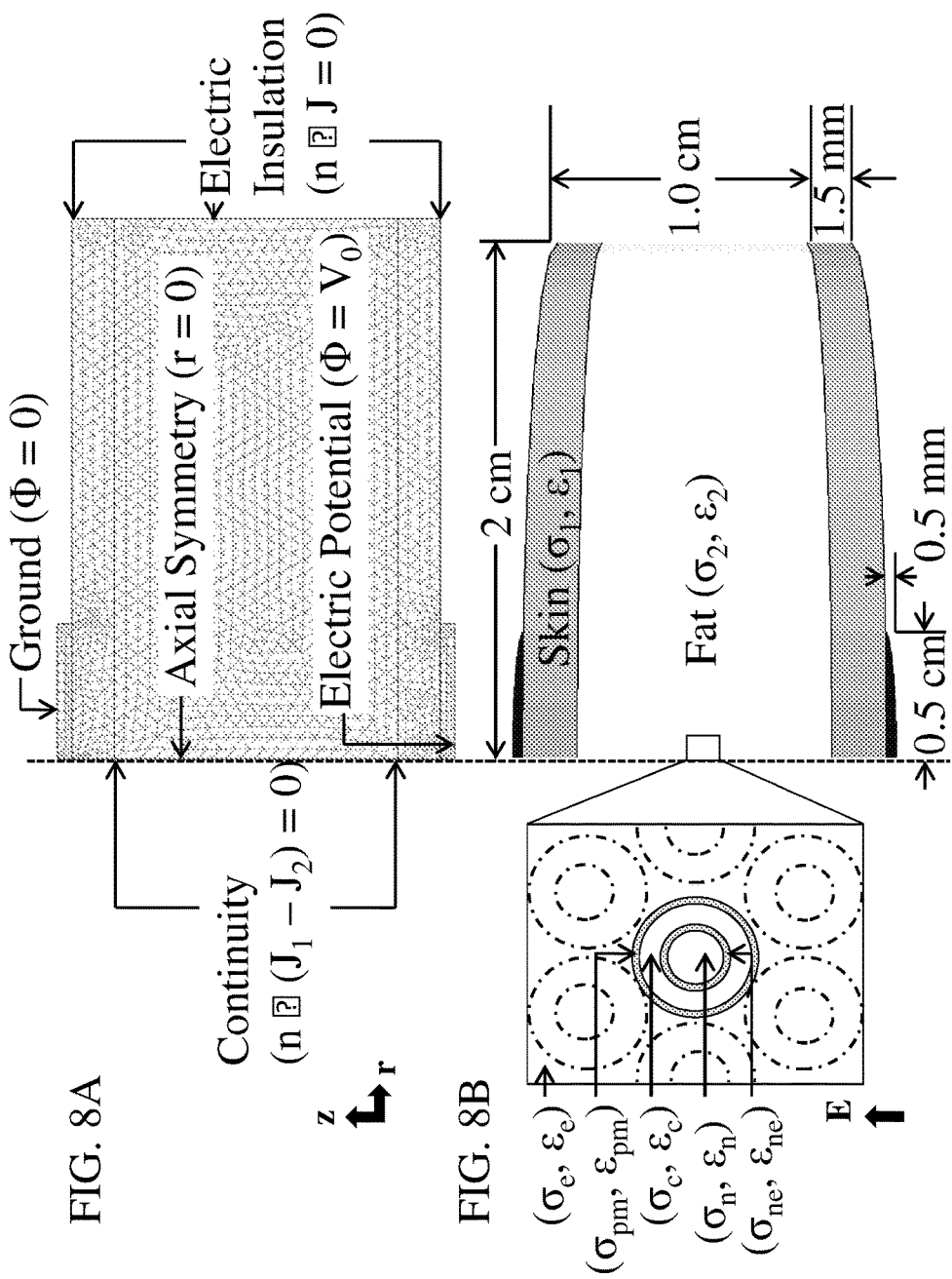
FIGS. 8A-B are schematic diagrams showing meshed geometry of the FEM with boundary settings (FIG. 8A) and the geometry with dimensions (FIG. 8B).
Figures 9B, 9D:
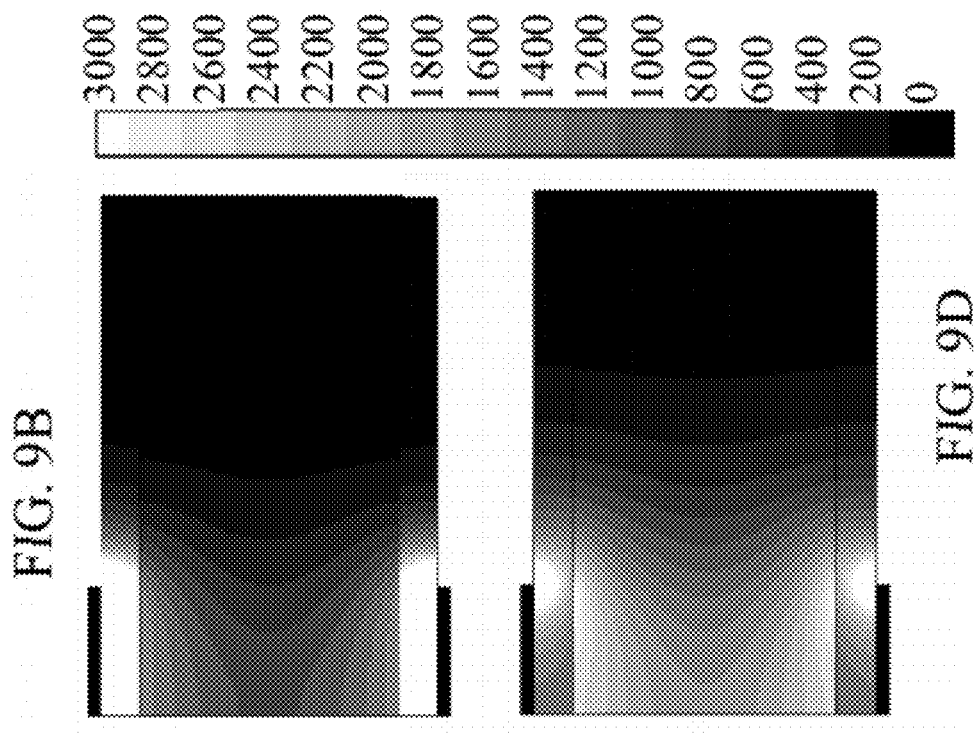
FIGS. 9A-D are schematic diagrams showing the electric field, norm (V/cm) contours predicted by the FEM at the end of a 2 µs burst with an amplitude of 2600 V and a frequency of 250 kHz (FIG. 9A), 500 kHz (FIG. 9B), 1 MHz (FIG. 9C), and 2 MHz (FIG. 9D).
Figures 9A, 9C:
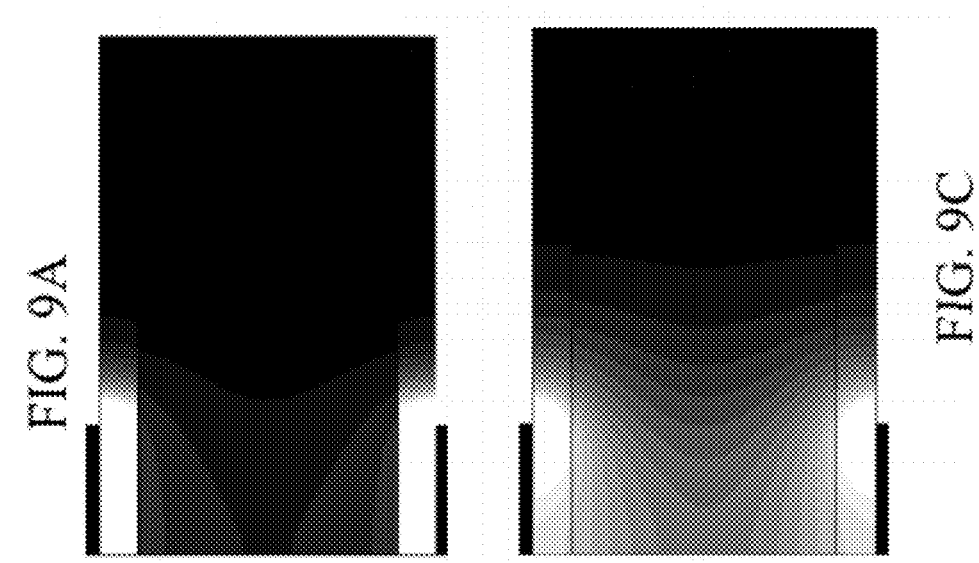

Dielectric properties of the bulk tissue were chosen from data generated by Gabriel et al. (see Gabriel, S., R. W. Lau, and C. Gabriel, *The dielectric properties of biological tissues .2. Measurements in the frequency range 10 Hz to 20 GHz*. Physics in Medicine and Biology, 1996. 41(11): p. 2251-2269) available at (http://niremf.ifac.cnr.it/docs/dielectric/home.html). The data was interpolated in Mathematica 7 (Wolfram Research, Inc.) in order to estimate the dielectric properties at the desired frequencies. Dielectric properties of the electrode were chosen to be stainless steel, as incorporated in the Comsol material library. All electrical boundary conditions are shown in FIGS. 8A-B, which provides in FIG. 8A, a meshed geometry of the FEM with boundary settings. The mesh consists of 3028 elements and was refined until there was <0.1% change in the magnitude of the electric field at the center of the tissue. FIG. 8B provides a schematic diagram of the geometry with dimensions. The box represents an expanded view of the tissue that describes the link between the macroscopic electric field (E) and the microscopic analysis of TMP. Adjacent cells are drawn with dashed lines, indicating their role was ignored in calculating TMP.

Because rectangular waveforms are comprised of components with various frequencies and amplitudes, tissue properties at frequencies associated with the center frequency, defined as the inverse of twice the duration of single polarity, are chosen. Intuitively, the duration of single polarity defines the frequency at which the current changes direction in the tissue. The pulses were constructed by multiplying the applied voltage by a function consisting of two smoothed Heaviside functions with a continuous second derivative and a tolerance of 5 ns (rise and fall times). The quasi-static assumption is confirmed based on the fact that the primary frequency of the pulses is lower than 200 MHz (rise and fall times), which corresponds to a wavelength that is greater than the longest dimension in the geometry. Chen, M. T., C. Jiang, P. T. Vernier, Y. H. Wu, and M. A. Gundersen, *Two-dimensional nanosecond electric field mapping based on cell electropermeabilization*. PMC Biophys, 2009. 2(1): p. 9. The inclusion of a permittivity term in (1) differs from previous, simplified models (see Edd, J. F. and R. V. Davalos, *Mathematical Modeling of irreversible Electroporation for treatment planning*. Technology in Cancer Research & Treatment, 2007. 6(4): p. 275-286; and Neal, R. E. and R. V. Davalos, *The Feasibility of Irreversible Electroporation for the Treatment of Breast Cancer and Other Heterogeneous Systems*. Annals of Biomedical Engineering, 2009. 37(12): p. 2615-2625), and accounts for reactive component of tissue to time dependent pulsing, which is required for obtaining accurate potential distributions in heterogeneous models. Yousif, N., R. Bayford, and X. Liu, *The Influence of Reactivity of the Electrode-Brain Interface on the Crossing Electric Current in Therapeutic Deep Brain Stimulation*. Neuroscience, 2008. 156(3): p. 597-606.

FIGS. 9A-D show the electric field distribution at the end of a 2 μs burst with various frequencies given in Table 1. In each case, the maximum applied voltage was set to 2600 V (peak) in order to set up a voltage to distance ratio of 2000 V/cm between the electrodes (1.3 cm spacing). From the surface contour map, as frequency is increased, the electric field in the fat rises while the field in the skin drops. This trend extends to the point that at 2 MHz the field in the skin is lower than the fat, which is a direct result of the tissue dielectric properties at that frequency (greater conductivity and permittivity of skin as compared to fat). Therefore, high-frequency fields, or pulses with shorter duration, are better suited to penetrate epithelial layers, such as the skin, and reach underlying tissue.

Example 2

High-frequency electroporation results in homogeneous energy deposition and reduces the potential for thermal damage in low passive conductivity tissue.

The temperature distribution in the model described in EXAMPLE 1 was obtained by transiently solving a modified version of the Pennes bioheat equation (see Pennes, H. H., *Analysis of tissue and arterial blood temperatures in the resting human forearm.* J Appl Physiol, 1948. 1(2): p. 93-122) with the inclusion of a Joule heating term:

$$\rho C \frac{\partial T}{\partial t} = \nabla \cdot (k \nabla T) + \rho_b \omega_b C_b (T_b - T) + Q_m + |J \cdot E| \quad (9)$$

where T is the tissue temperature, $T_b$ is the blood temperature, k is the thermal conductivity of the tissue, C and $C_b$ are the tissue and blood specific heat, respectively, $\rho$ and $\rho_b$ are the tissue and blood density, respectively, $Q_m$ is the metabolic heat source term, $\omega_b$ is the blood perfusion coefficient, and $|J \cdot E|$ is the Joule heating term. All thermal tissue properties are given in Table 3. Fiala, D., K. J. Lomas, and M. Stohrer, *A computer model of human thermoregulation for a wide range of environmental conditions: the passive system.* Journal of Applied Physiology, 1999. 87(5): p. 1957-1972.

TABLE 3

Thermal tissue properties of various tissues.

| | Tissue | | |
|---|---|---|---|
| Property | Blood | Skin | Fat |
| $\rho$ [kg/m³] | 1069 | 1085 | 850 |
| C [J/(Kg·K)] | 3650 | 3680 | 2300 |
| k [W/(m·K)] | — | 0.47 | 0.16 |
| $\omega$ [1/s] | — | 1.1 | 0.0036 |
| $Q_m$ [kg/m³] | — | 368 | 58 |

Due to the presence of different tissue layers and the high frequencies under consideration (250 kHz-2 MHz), displacement currents are considered along with conduction currents in the formulation of Joule heating:

$$J = J_D + J_C = \varepsilon_0 \varepsilon_r \frac{\partial E}{\partial t} + \sigma E \quad (10)$$

where J is the total current density, $J_D$ is the displacement current density, and $J_C$ is the conduction current density. In order to ensure that negative current components due to polarity changes add to the total current in the tissue, the absolute value of the resistive heating term was taken prior to temperature calculations. It was assumed that all subdomains were initially at physiologic temperature ($T_0$=310.15 K). The boundaries between the electrode-skin interface and the skin-fat interface were treated as continuous (n·($k_1 \nabla T_1 - k_2 \nabla T_2$)=0), the centerline was defined as axial symmetry (r=0), and the remaining boundaries were thermally insulated (n·(k∇T)=0) for conservative temperature estimates. Temperature profiles were investigated along the centerline (r=0 mm) in the middle of the fat (z=0 mm) and skin (z=5.75 mm) layers. Data was imported into Mathematica, and a moving average with a period of 100 ns was taken to smooth the plots. Additionally, the data was fit with a linear trendline in order to extrapolate to longer burst widths and predict the onset of thermal damage.

Temperature changes predicted by the FEM at the center of the skin and fat are shown in FIGS. 10A-B, which provides temperature changes predicted by the FEM at the center of the skin (FIG. 10A) and fat (FIG. 10B) for frequencies of 250 kHz (- -), 500 kHz (- - -), 1 MHz ( . . . ), and 2 MHz (-). Equations represent a linear fit to the data. In this case, a burst width of 4 µs was simulated in order to capture the trends in temperature development. Polarity of the 2 µs pulse (250 kHz) was switched between pulses to maintain consistency with the other waveforms that are inherently bipolar. With respect to the skin, as the frequency of the applied field increases, the temperature rises at a slower rate. This is a consequence of the fact that the electric field within the skin also decreases with increasing frequency. In the case of the fat, the temperature rises at a faster rate when the frequency of the applied field is increased. At first glance, this seems to be detrimental, however, it is merely an indication that energy is preferentially being deposited more uniformly into the fat at higher frequencies. Again, this can be correlated to the electric field profile. In both tissues, the sharp rises in temperature are due to the spikes in displacement current that occur at the onset and offset of each pulse (data not shown). The total temperature increase in all cases is less than 0.003 K for a burst width of 4 µs. As explained in the discussion, even for bursts of longer widths, the temperature increase is not enough to promote thermal damage.

The onset of protein denaturation and loss of cell structure occurs above 318.15 K (see Bilchik, A. J., T. F. Wood, and D. P. Allegra, *Radiofrequency ablation of unresectable hepatic malignancies: Lessons learned.* Oncologist, 2001. 6(1): p. 24-33), which correlates to an increase in temperature of 8 K above physiological temperature. Using this information, the maximum energy delivery period (number of pulses multiplied by pulse duration) can be calculated for an amplitude of 2000 V/cm at each of the frequencies investigated using the trendlines generated by the FEM data (FIGS. 9A-D). In the skin layer, heating is reduced by increasing the frequency of the applied field. This shows that the potential for thermal damage in the skin is reduced when the frequency of the applied field is increased. At higher frequencies, the energy is preferentially deposited in the fat layer. For 2 MHz, the total energy delivery period required to cause an 8 K increase in temperature is 12 ms. An example treatment plan can include 12, 1 ms pulses separated by a delay of 1 s. If the frequency is reduced to 500 kHz, which shows the greatest electroporation efficiency (Table 4, see EXAMPLE 3), the allowable energy delivery period increases to 16 ms, which would permit the delivery of an additional 4, 1 ms pulses before the onset of thermal damage.

TABLE 4

Various exemplary treatment protocols.

| Frequency (pulse duration) | Time (µs), \|TMP\| > 0.5 V | % of Pulse, \|TMP\| > 0.5 V |
|---|---|---|
| 250 kHz (2 µs) | 1.2 | 60 |
| 500 kHz (1 µs (×2)) | 1.9 | 95 |
| 1 MHz (500 ns (×4)) | 1.3 | 65 |
| 2 MHz (250 ns (×8)) | 0.1 | 5 |

The restrictions could be increased if less conservative estimates are obtained that account for heat dissipation between pulses and heat convection at the tissue surface. Lackovic, I., R. Magjarevic, and D. Miklavcic, *Three-dimensional Finite-element Analysis of Joule Heating in Electrochemotherapy and in vivo Gene Electrotransfer.* Ieee Transactions on Dielectrics and Electrical Insulation, 2009. 16(5): p. 1338-1347. These projected protocols represent a maximum, and it is likely that the desired effects will be induced at a significantly lower energy. See Belehradek, J., S. Orlowski, L. H. Ramirez, G. Pron, B. Poddevin, and L. M. Mir, *Electropermeabilization of Cells in Tissues Assessed by the Qualitative and Quantitative Electroloading of Bleomycin*. Biochimica Et Biophysica Acta-Biomembranes, 1994. 1190(1): p. 155-163; and Garcia, P. A., J. H. Rossmeisl, R. E. Neal, T. L. Ellis, J. D. Olson, N. Henao-Guerrero, J. Robertson, and R. V. Davalos, *Intracranial Nonthermal Irreversible Electroporation: In Vivo Analysis*. Journal of Membrane Biology, 2010. 236(1): p. 127-136.

Example 3

High-frequency electroporation can overcome shielding effects of low passive conductivity tissues and induce electroporation in underlying layers.

The analytical model for TMP described in this specification was utilized to investigate electroporation in a hypothetical cell located along the centerline (r=0 mm) in the middle of the fat (z=0) and skin (z=5.75 mm) layers of the FEM described in EXAMPLE 1. The equations for TMP are derived under the assumption that there is no influence on the microscopic electric field from neighboring cells. Therefore, the macroscopic electric field in the bulk tissue predicted by the FEM dictates the microscopic electric field experienced by the cell. The vertical z-component of the electric field was imported from the specific locations within FEM into Mathematica to account for polarity changes. The radial r-component was neglected due to the fact that it never surpassed 3 V/cm as current traveled primarily in the z-direction. Non-uniform electric field data was fit with a series of step functions (50 ns duration), such that the Laplace transform of the field could be performed and the solution for TMP could be obtained in the frequency domain as the summation of individual steps. The inverse Laplace transform of the data was taken to obtain the complete time courses. Measurements were taken at the pole (θ=0) to depict the maximum induced TMP around the cell.

Figure 11A:
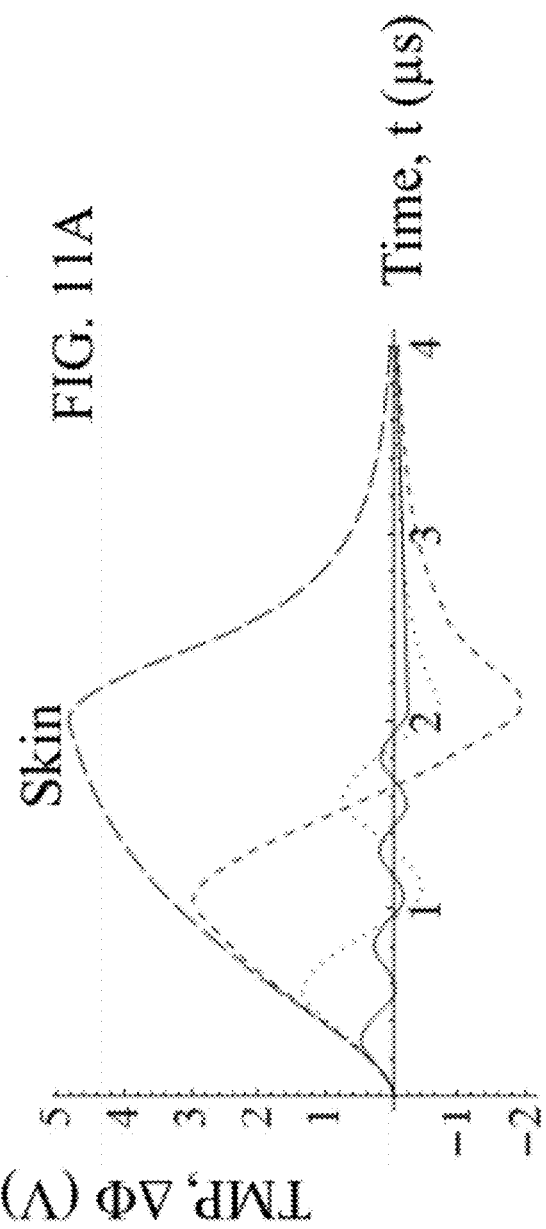
FIGS. 11A-B are graphs of TMP predicted by the FEM at the center of the skin (FIG. 11A) and fat (FIG. 11B) for frequencies of 250 kHz (- - ), 500 kHz ( - - -), 1 MHz ( . . . ), and 2 MHz (-).
Figure 11B:
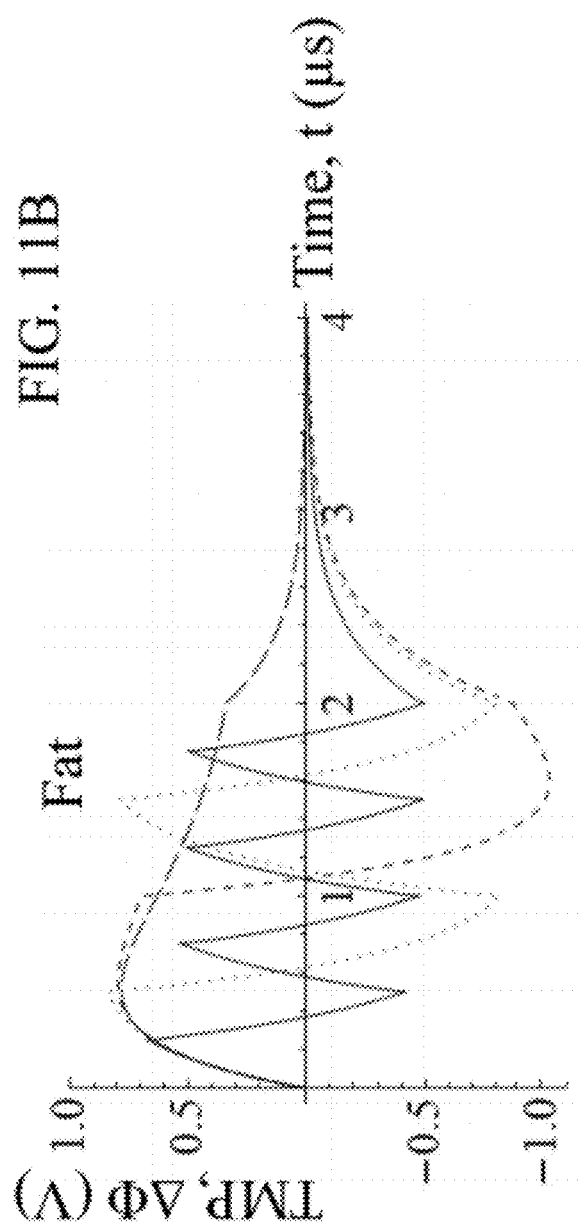

With respect to the skin, as the frequency of the applied field increases, the maximum oscillation amplitude of the TMP decreases, as shown in FIGS. 11A-B. This occurs for two reasons. First, as seen in FIGS. 8A-B, the electric field in the skin decreases with increasing frequency. Second, as seen in FIG. 5, even with constant field amplitude, the TMP decreases with increasing frequency, because the time during which the membrane has to charge before the polarity switches is less at higher frequencies. In the case of the fat, the behavior is slightly more complex. At lower frequencies, a majority of the voltage drop occurs across the skin as demonstrated in FIGS. 9A-D, resulting in a reduced electric field in the fat. This shielding effect is best shown in FIGS. 10A-B along the 250 kHz trace. According to FIG. 5, at 250 kHz, the maximum TMP should be reached. However, due to the shielding effect from the skin, a reduction in the TMP prior to the polarity change is seen. This reduction in TMP can be alleviated by increasing the frequency of the applied field. However, the tradeoff between increased frequency and reduced TMP is still evident at a frequency of 2 MHz (FIGS. 11A-B).

As mentioned, there is a balance between employing pulses that are delivered on a short enough timescale to flow through epithelial cells but are long enough to induce electroporation in underlying cells. The time constant of 345 ns, predicted by the analytical model for TMP, falls between the 2 MHz (250 ns pulse duration) and 1 MHz (500 ns pulse duration) bursts. Further, the 500 kHz burst (1 μs pulse duration) is close to the time it takes the TMP to reach steady state. Table 4 summarizes the results based on the time that the TMP on a hypothetical cell at the center of the fat layer is above 0.5 V. This amplitude was chosen such that even the highest frequency burst was above the set voltage level for a certain amount of time. The results would hold if the applied field was doubled and the voltage level was set to the 1 V threshold for pore formation, due to the linear dependence of TMP on the electric field. Based on this criterion, a frequency of 500 kHz is best suited to treat cells in the fat layer, followed by 1 MHz and 250 kHz. As frequency is increased, the dielectric properties and electric field distribution in the skin and fat become more macroscopically homogeneous, but above 1 MHz, the pulse duration is not adequate for the cell to charge.

Example 4

System for implementing high-frequency, bipolar pulses for tissue electroporation.

Figure 12:
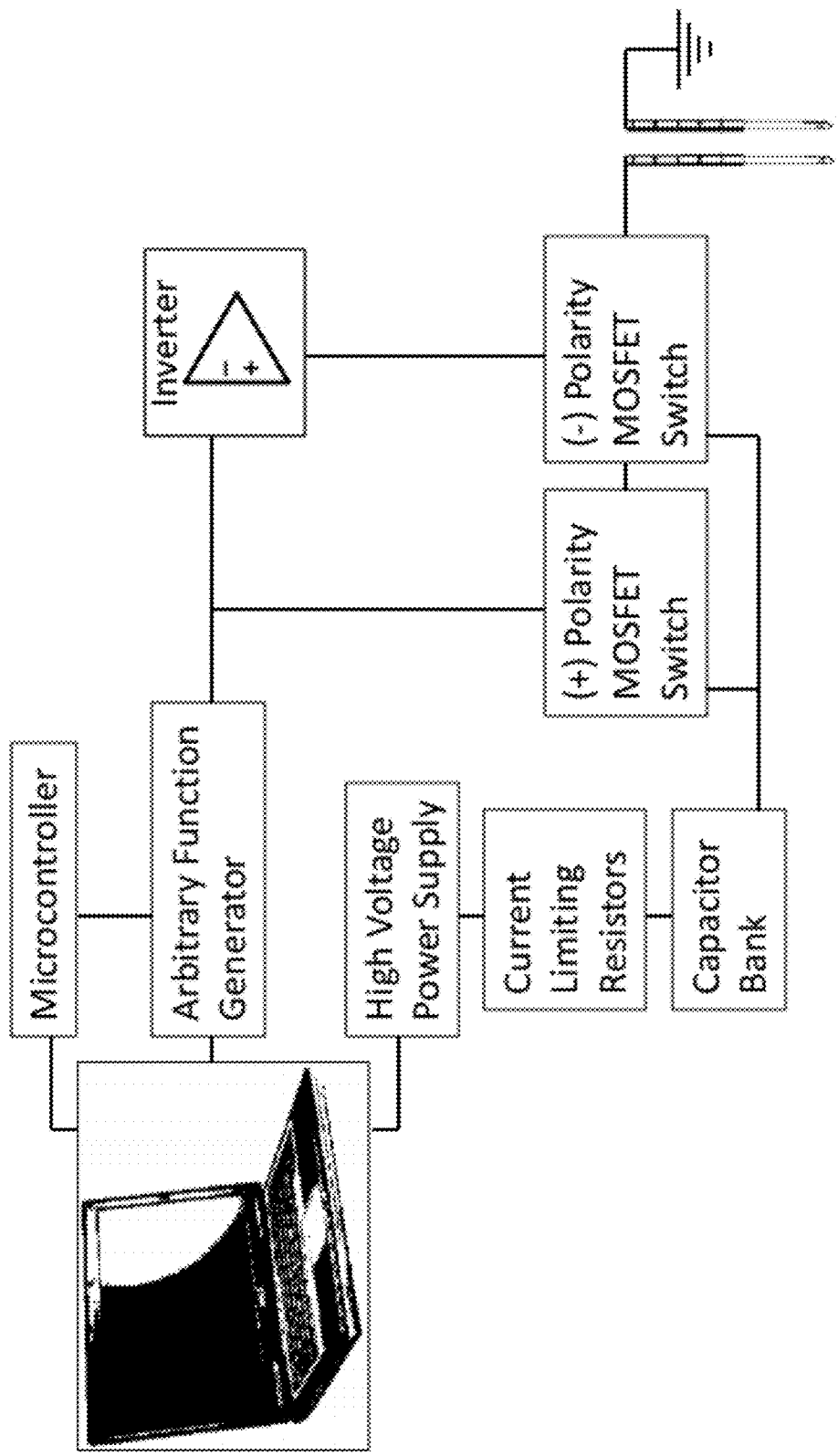
FIG. 12 is a diagram of a system for implementing high-frequency, bipolar pulses for tissue electroporation.

The electronic drive system for delivering bipolar electroporation signals is schematically depicted in FIG. 12. The system relies upon both commercially available components and circuits built by the inventors. An arbitrary function generator (Tektronix AFG 3011) is programmed to output a tri-state square waveform. The AFG 3011 is capable of generating 20 V peak-to-peak into a 50 ohm load and has an effective analog bandwidth of 8 MHz. The burst width, interval between bursts, and total number of bursts is externally controlled by a microcontroller (Arduino Duemilanove) through the general purpose input/output (GPIO) pins. The output signal for a 1 MHz waveform with a burst width of 10 μs and amplitude of 6 V peak is given in FIG. 12. This signal is simultaneously fed through both positive polarity and negative polarity high voltage MOSFET switches (IXYS Colorado HV 1000). The signal into the negative polarity HV 1000 is inverted using an LM 7171 op amp with a slew rate of 4100 V/μs in order to properly sequence the amplification of the positive and negative polarity pulses without delay. The maximum output of each HV 1000 is 17 A and +/−850 V into a 50 ohm load. Additionally the pulse rise time is 10 ns or less. This results in an amplification of the AFG 3011 trigger signal up to 1700 V peak-to-peak, which is capable of inducing electroporation when the electrodes are spaced approximately 3 cm apart or less. The input power to each HV 1000 is maintained by a high voltage sequencer (LabSmith HVS 448), which can regulate voltage up to +/−3000 V and current up to 100 mA. In order to increase current storage up to 17 A, an external capacitor bank was included between the HVS 448 and HV 1000. The total capacitance of the bank can be adjusted depending on the desired voltage and current output or electrode spacing. This system allows for a flexible treatment program that may be tailored to meet a patient's individual needs.

Other systems are available in the literature for generating bipolar pulses, and the invention should not be limited to the system described above. For example, De Vuyst et al. built a generator around an NE555 timer configured as an astable multivibrator capable of producing up to 50 kHz bipolar pulses. De Vuyst, E., M. De Bock, E. Decrock, M. Van Moorhem, C. Naus, C. Mabilde, and L. Leybaert, *In situ bipolar Electroporation for localized cell loading with reporter dyes and investigating gap junctional coupling*. Biophysical Journal, 2008. 94(2): p. 469-479. However, the frequency of the pulses administered according to embodiments of the invention are an order of magnitude greater, which is easily met by the bandwidth of the AFG 3011.

Additionally, the MOSFET switches provide an excellent means to produce high-frequency pulses for high voltage switching. However, MOSFETs are not the only semiconductor devices that can be utilized to produce a pulse. Bipolar Junction Transistors (BJTs), Insulated Gate Bipolar Transistors (IGBTs), and Junction Field Effect Transistors (JFETs) are examples of some of the semiconductor devices that may be used to produce an output pulse.

Example 5

Experimental results of high-frequency, bipolar pulses for electroporation of cells.

A chemical reaction technique was performed to fabricate parallel silver electrodes on glass microscope slides with 100 µm spacing. Briefly, a commercially available mirroring kit was used to deposit pure silver onto the microscope slides (Angel Gilding Stained Glass Ltd, Oak Park, Ill.). A negative thin film photoresist (#146DFR-4, MG Chemicals, Surrey, British Colombia, Canada) was laid on top of the slide and passed through an office laminator (#4, HeatSeal H212, General Binding Corporation, Lincolnshire, Ill.). A photomask printed at 20 k DPI on a transparent film (Output City, Cad/Art Services Inc, Bandon, Oreg.) was placed ink side down onto the photoresist, and slides were exposed to UV light for 45 seconds. After exposure, the slides were placed in a 200 mL bath containing a 10:1 DI water to negative photo developer (#4170-500ML, MG Chemicals, Surrey, British Colombia, Canada). The slides were placed in a beaker containing DI water to stop the development process and gently dried using pressurized air. Electrode structures on the microscope slides were fabricated by removing all silver not covered by the patterned photoresist. A two part silver remover was included in the mirroring kit used to deposit the silver. The photoresist was then removed by placing the slide in a bath of acetone.

Microfluidic channels were fabricated using the patterned photoresist on a microscope slide that had not undergone the silvering process. Liquid phase polydimethylsiloxane (PDMS) in a 10:1 ratio of monomers to curing agent (Sylgrad 184, Dow Corning, USA) was degassed under vacuum prior to being poured onto the photoresist master and cured for 1 hour at 100° C. After removing the cured PDMS from the mold, fluidic connections to the channels were punched in the devices using 1.5 mm core borers (Harris Uni-Core, Ted Pella Inc., Redding, Calif.). The PDMS mold was then bonded over the glass slides containing the patterned electrodes by treating with air plasma for 2 minutes in a PDC-001 plasma cleaner (Harrick Plasma, Ithaca, N.Y.).

Figures 13A, 13B:
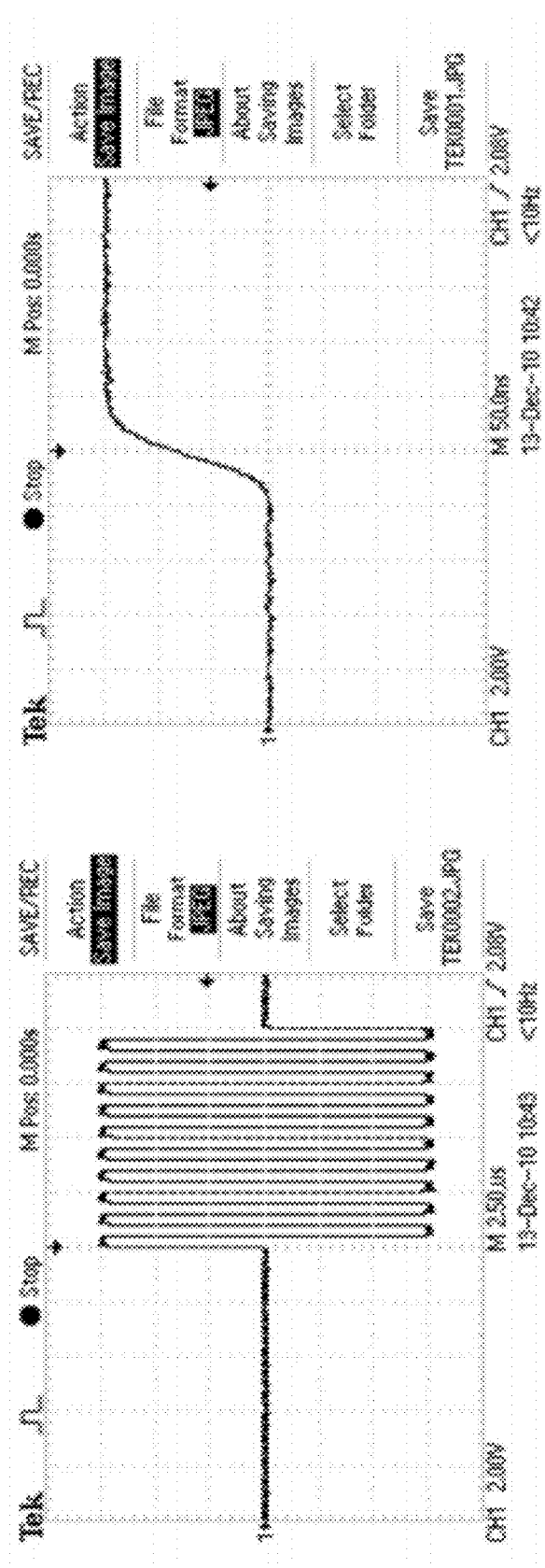
FIGS. 13A-B are graphs showing output of the arbitrary function generator prior to signal amplification by the high voltage MOSFET positive and negative polarity switches.

High voltage electrical wires were taped to the glass slide with exposed wire placed in direct contact with the electrical pads. A drop of high purity silver paint (Structure Probe Inc., West Chester, Pa.) was placed on the pad and allowed to dry for one hour creating a solid electrical connection. A drop of 5 minute epoxy (Devcon, Danvers, Mass.), used to secure the electrical connections, was placed on top of each electrode pad and allowed to cure for 24 hours. Pulses were delivered across the electrodes as described in EXAMPLE 4 prior to the amplification stage. No amplification was needed as the gap between the electrodes was only 100 µm. Therefore, the output signal of a function generator (GFG-3015, GW Instek, Taipei, Taiwan) +/−10 V can be used to generate an electric field capable of inducing electroporation, as shown in FIGS. 13A-B.

Figure 14B:
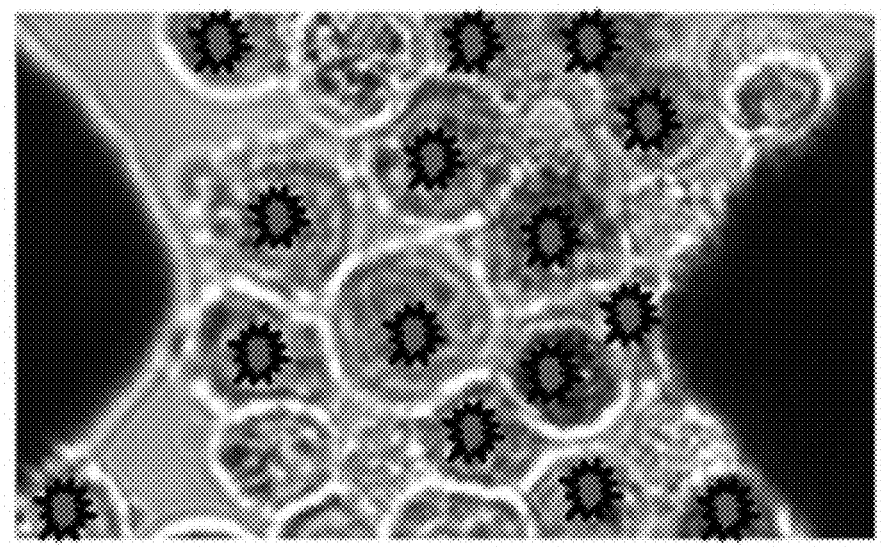
FIGS. 14A-B are micrographs showing in vitro experimental results on electroporation with high-frequency bipolar, pulses using a trypan blue dye exclusion assay.
Figure 14A:
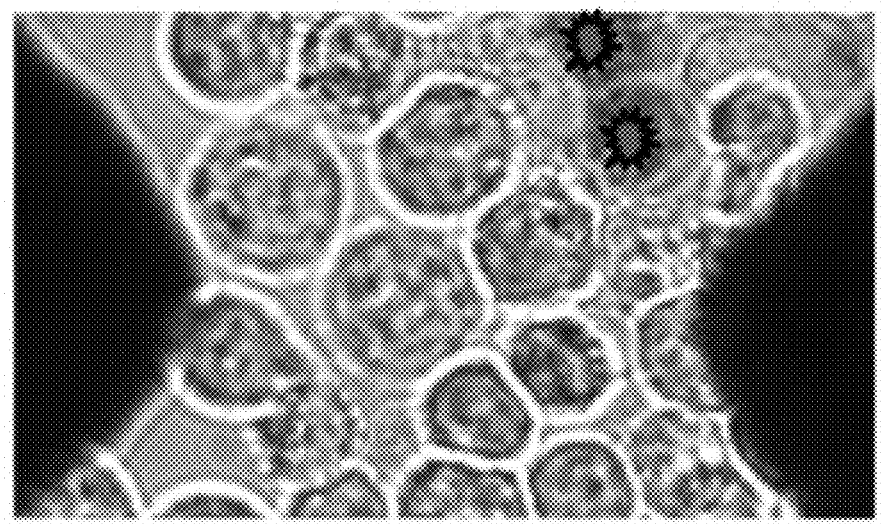

Following culture in DMEM-F12 (supplemented with 10% FBS and 1% penicillin streptomycin) MDA-MB-231 cells were resuspended in a PBS solution 1:1 with Trypan Blue (0.4%). Trypan Blue is a determinant of cell membrane integrity, and stains electroporated cells blue, whereas non-electroporated cells remain transparent. Cells at a concentration of $10^6$/ml were injected into the microfluidic channel using a syringe. The function generator was triggered by the microcontroller to deliver 80, 50 kHz bursts with a width of 1 ms and an amplitude of 500 V/cm. Results shown in FIGS. 14A-B, which shows that 60% transfection efficiency was obtained when starting with cells that are 92% viable. This efficiency of reversible electroporation could be improved by either increasing the number of pulses or the burst width. Additionally, IRE could be performed by increasing the applied voltage.

Example 6

Alternate waveforms for performing high-frequency electroporation.

Figure 16:
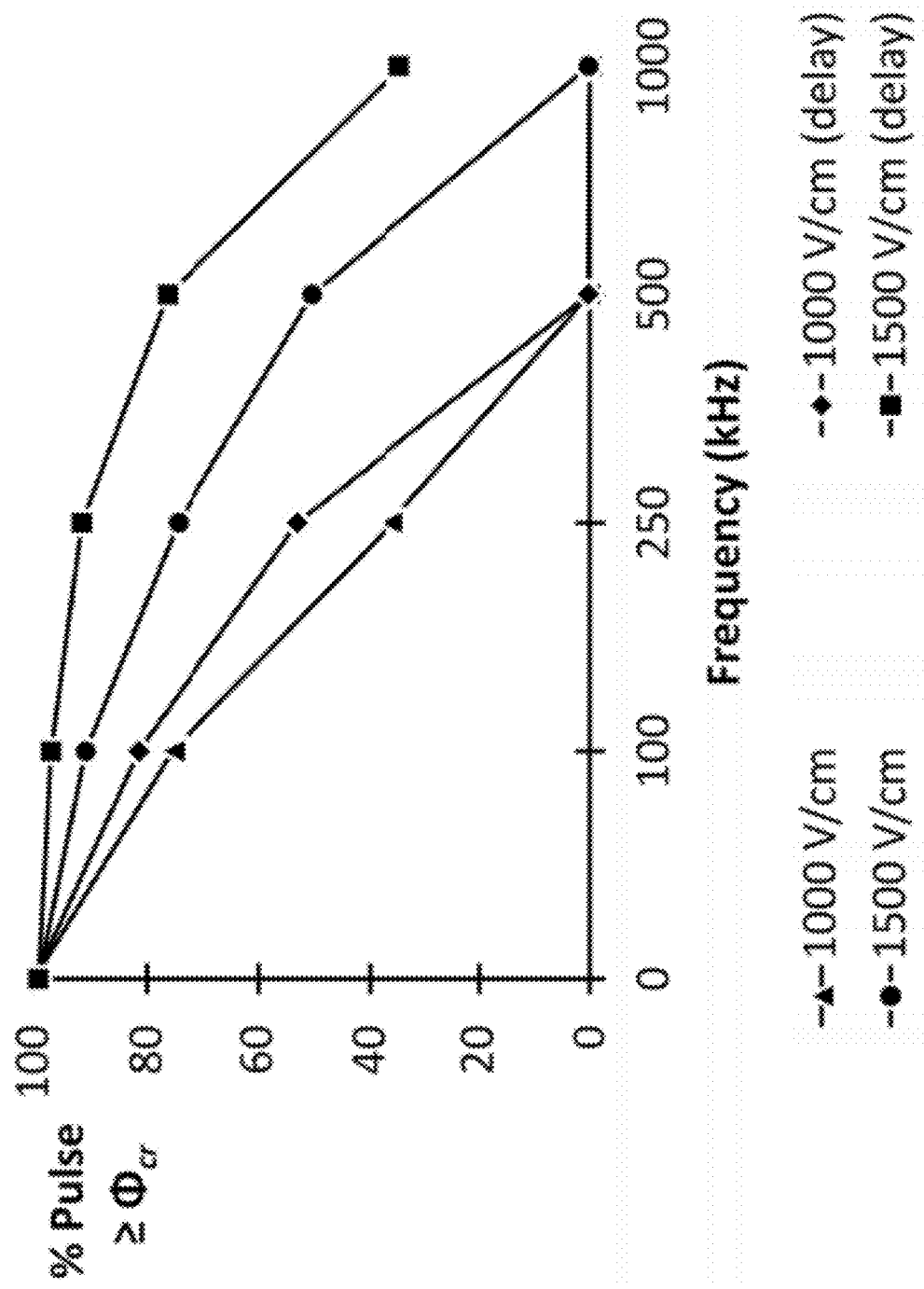
FIG. 16 is a graph comparing time above the critical threshold ($\Phi_{cr}$) for IRE at various center frequencies.

The analytical model for TMP described in the detailed description of the invention was utilized to investigate electroporation of a spherical cell subject to alternative waveforms. As mentioned, the critical TMP ($\Phi_{cr}$) across the plasma membrane required to induce IRE is approximately 1 V. Belehradek, J., S. Orlowski, L. H. Ramirez, G. Pron, B. Poddevin, and L. M. Mir, *Electropermeabilization of Cells in Tissues Assessed by the Qualitative and Quantitative Electroloading of Bleomycin.* Biochimica Et Biophysica Acta-Biomembranes, 1994. 1190(1): p. 155-163. This threshold is illustrated in FIGS. 15A-C by the dashed, horizontal line on the TMP profiles. Characteristic waveforms of IRE with unipolar pulses and high-frequency IRE with the corresponding TMP development across the plasma membrane ($\Phi_{pm}$). All results are presented at the cell pole (θ×0) to show the maximum TMP around the cell. Further, results are only shown for TMP across the plasma membrane, as the TMP across the nuclear envelope never approached the permeabilizing threshold. For an electric field of 1500 V/cm, results indicate that a unipolar pulse (FIG. 15A), a 250 kHz bipolar burst (FIG. 15B), and 250 kHz bipolar burst that includes delays between the pulses (FIG. 15C) are all capable of inducing IRE. However, the time above the threshold TMP varies between the different cases. The 1500 V/cm unipolar pulse causes the TMP to rise above the critical threshold for IRE (1 V, dashed line). The 1500 V/cm bipolar burst without a delay and with a delay causes the TMP to oscillate around the same critical threshold. This is investigated further in FIG. 16 for center frequencies of 0, 100, 250, 500, and 1000 kHz, with the 0 kHz case representing the unipolar pulse, and electric fields of 1000 V/cm and 1500 V/cm. FIG. 16 provides a comparison of time above the critical threshold ($\Phi_{cr}$) for IRE at various center frequencies. The burst width of the bipolar waveform that included delays was twice as long (40 µs) as the corresponding burst with no delays in order to generate an equivalent pulse on-time (20 µs). The amount of time that the TMP was above the critical value was normalized by the on-time and converted to a percentage. FIG. 16 illustrates that, for a given frequency, as the electric field is increased from 1000 V/cm to 1500 V/cm, the percentage of the burst above the critical TMP also increases. At 250 kHz, IRE is possible during all waveforms, but at 500 kHz, only the waveforms with amplitudes of 1500 V/cm are capable of inducing IRE. As the center frequency of the burst increases, the percentage of the burst above the critical TMP decreases. However, with the inclusion of delays between the pulses, this characteristic dispersion is shifted towards higher frequencies. At 1 MHz, only the 1500 V/cm waveform with delays can theoretically cause IRE.

The theoretical model of TMP suggests that IRE should be possible up to 1 MHz for an electric field of 1500 V/cm. Including a delay between the positive and negative pulses comprising the bipolar burst offers a therapeutic advantage in addition to protecting the MOSFETs in the pulse generation system (see EXAMPLE 4) from ringing. By not forcing a discharge of the TMP with an immediate reversal of polarity, the cell is allowed to return to the resting TMP according to its characteristic time constant. As a result, the TMP is maintained above the critical voltage required for IRE for a longer amount of time. This metric has been recognized as a potential indicator of treatment outcomes in electroporation based therapies with bipolar waveforms. Garcia, P. A., J. H. Rossmeisl, R. E. Neal, T. L. Ellis, J. D. Olson, N. Henao-Guerrero, J. Robertson, and R. V. Davalos, *Intracranial Nonthermal Irreversible Electroporation: In Vivo Analysis*. Journal of Membrane Biology, 2010. 236(1): p. 127-136.

Figure 17:
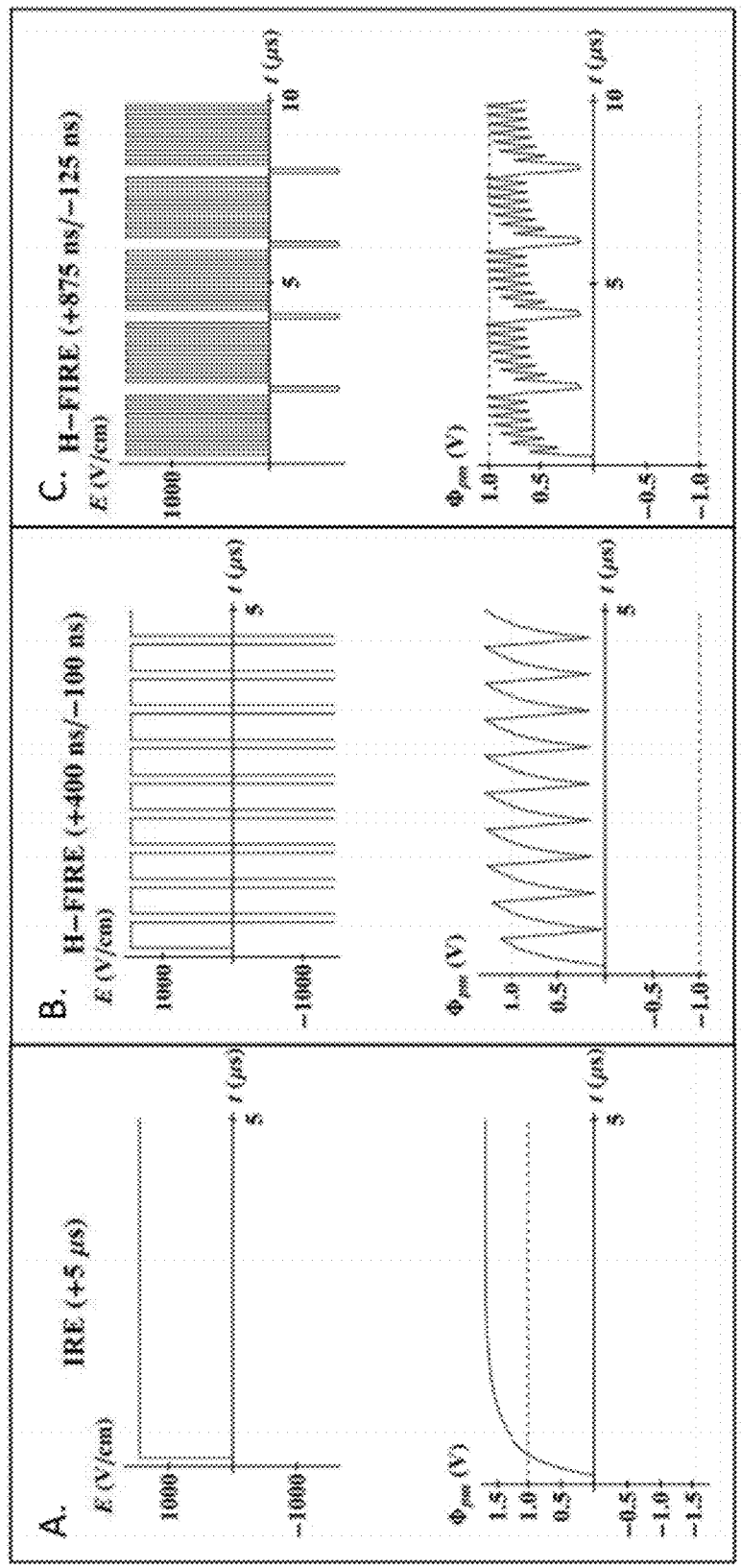
FIGS. 17A-C are waveforms of IRE with unipolar pulses and high-frequency IRE with the corresponding TMP development across the plasma membrane ($\Phi_{pm}$) for a 1500 V/cm unipolar pulse (FIG. 17A), a 1500 V/cm bipolar burst without a delay and with a shortened negative phase (FIG. 17B), and a 1500 V/cm bipolar burst with a delay and with a shortened, lower amplitude negative phase (FIG. 17C).
Figure 18:
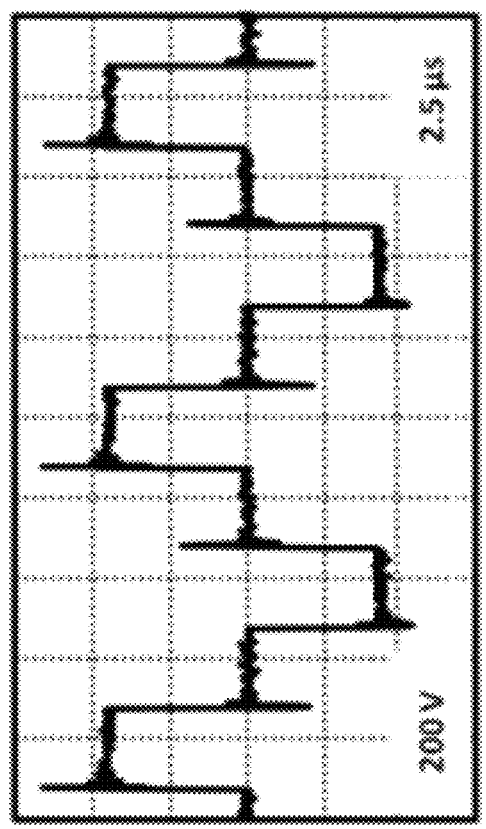
FIG. 18 is a chart showing an exemplary output from an in vivo treatment of the brain with high-frequency, bipolar pulses, where the snapshot is taken within a single burst.

Other potential waveforms for performing high-frequency electroporation are shown in FIGS. 17A-C, which provide characteristic waveforms of IRE with unipolar pulses and high-frequency IRE with the corresponding TMP development across the plasma membrane ($\Phi_{pm}$). A unipolar pulse with an amplitude of 1500 V/cm is shown for comparison (FIG. 17A). A waveform without delays between polarity reversals (FIG. 17B) can maintain a positive TMP throughout the entire treatment if the duration of positive polarity is tuned to be slightly longer than the duration of negative polarity. Similarly, for a waveform that includes delays (FIG. 17C), a train of positive ultra-short pulses could be used to gradually increase the TMP up to the critical permeabilizing threshold, and a single ultra-short pulse of negative polarity could follow the train without causing the TMP to go negative. In both examples, the ultra-short negative going pulse is designed to maintain the predicted benefits of high-frequency electroporation. Namely, it is predicted that the negative going pulse will prevent action potential generation and still permit a degree of capacitive coupling across epithelial layers. FIG. 18 is a chart showing an exemplary output from an in vivo treatment of the brain with high-frequency, bipolar pulses, where the snapshot is taken within a single burst.

Example 7

Experimental results of high-frequency IRE (H-FIRE) of brain tissue.

H-FIRE was performed using a custom pulse generator as described in EXAMPLE 4 with minor modifications. An unregulated DC power supply was constructed to replace the both the high voltage sequencer and external capacitor in order to maintain a sufficient level of charge to deliver 20 A over a 100 µs burst. A center tapped 400 VA transformer (AS-4T320, Antek, Inc., North Arlington, N.J., USA) was rectified and smoothed by a capacitor bank to provide positive and negative power rails to the HV1000P and HV1000N, respectively. The voltage rails were controlled by adjusting the input voltage using a variable transformer, and the maximum output rating of the system was +/−450 V. A delay equal to the duration of single polarity was included between the pulses in order to protect the MOSFETs from ringing. A unity gain inverting amplifier (AD844, Analog Devices, Norwood, Mass., USA) was used to invert this signal and appropriately trigger the negative pulse generator. The outputs of the two monopolar pulse generators were terminated into a 50Ω load in parallel with the electrodes. This load was used to maintain appropriate pulse characteristics and as a safety to ensure the system was never triggered without an attached load. For comparison, the IRE treatments were performed using the BTX ECM 830 electroporation system (Harvard Apparatus, Holliston, Mass., USA).

All study procedures were conducted following Institutional Animal Care and Use Committee approval and performed in a GLP compliant facility. Four, Fischer 344 male rats weighing 200-240 g were anesthetized by intraperitoneal injection of 10 mg/kg xylazine and 60 mg/kg ketamine hydrochloride, and a surgical plane of anesthesia was assessed by loss of the tail pinch reflex. To monitor muscle contractions, a 3-axis accelerometer breakout board (ADXL335, Adafruit Industries, New York, N.Y., USA) with a sensing range of ±3 g's was sutured to the dorsum of each rat in the interscapular region at the cervicothoracic junction using 5-0 monocryl suture. Low-pass filter capacitors (0.1 µF) were included at the x, y, and z outputs of the accelerometer for noise reduction. The hair of the skull was clipped and aseptically prepared using povidone-iodine and alcohol solutions. Anesthetized rats were placed in a small animal stereotactic head frame (Model 1350M, David Kopf Instruments, Tungisten, Calif., USA). A routine lateral rostrotentorial surgical approach to the skull was made, and 6 mm by 3 mm rectangular parieto-occipital craniectomy defects were created in the right and left aspects of the skull of each rat using a high-speed electric drill. Custom electrodes were inserted into the center of the forelimb area of the sensorimotor cortex of each rat (coordinates relative to Bregma: 1 mm anterior, 2.5 mm lateral, 2 mm dorsoventral) and advanced to a depth of 2 mm beneath the surface of the exposed dura. The electrodes were fashioned by blunting stainless steel acupuncture needles (0.45 mm.diameter, Kingli Medical Appliance Co., Wuxi, China) with high grade sandpaper. Exposure length was set to 1 mm by insulating the electrodes with miniature polyimide tubing (25 AWG, Small Parts, Seattle, Wash., USA), and the edge-to-edge electrode spacing was set to 1 mm by molding the electrodes in liquid phase polydimethylsiloxane (PDMS) cured in a 10:1 ratio with Sylgard 184 (Dow Corning Corp., Midland, Mich., USA) at 150° C. for 30 min.

Pulse parameters were chosen based on the results from the analytical and numerical models to ensure the greatest potential for non-thermal tissue ablation. Following electrode insertion, pulses were applied to the right and left cerebral hemispheres, resulting in two treatments per rat (Table 5).

TABLE 5

Pulse parameters of various treatment protocols.

| Rat Number | Treatment | Hemisphere | Frequency (kHz) | Voltage (V) |
|---|---|---|---|---|
| 1 | IRE | Left | — | 100 |
|   | H-FIRE | Right | 250 | 100 |
| 2 | IRE | Left | — | 200 |
|   | H-FIRE | Right | 250 | 200 |
| 3 | H-FIRE | Left | 250 | 300 |
|   | H-FIRE | Right | 250 | 400 |
| 4 | IRE | Left | — | 50 |
|   | H-FIRE | Right | 500 | 400 |

H-FIRE experiments were performed using 180 bursts with a pulse on-time of 200 µs within each burst, and bursts were delivered at a rate of one per second. In Rat #1 and Rat

2, H-FIRE was applied at voltages of 100 V and 200 V, respectively, to the right hemisphere with a center frequency of 250 kHz (duration of single polarity equal to two microseconds). The left hemisphere of Rat #1 and Rat #2 were treated with 180 IRE pulses (200 μs duration) of equivalent energy. In Rat #3, H-FIRE was applied to the left and right hemispheres at voltages of 300 V and 400 V, respectively, with a frequency of 250 kHz. In Rat #4, H-FIRE was applied at a voltage of 400 V to the right hemisphere with a frequency of 500 kHz (duration of single polarity equal to one microsecond). The left hemisphere of Rat #4 was treated with 90 IRE pulses (200 μs) and an applied voltage of 50V. This lower energy scenario was designed to compare H-FIRE treatment outcomes to traditional IRE protocols in the brain. Kotnik, T. and D. Miklavcic, *Theoretical evaluation of voltage inducement on internal membranes of biological cells exposed to electric fields*. Biophysical Journal, 2006. 90(2): p. 480-491.

Immediately following treatment, Rats #3 and #4 were subjected to MRI examinations of the brain while under general anesthesia. The MRI was performed with a 0.2 T MRI scanner using a dual phased array hand/wrist coil for RF signal transmission and reception. Sequence acquisition parameters were as follows: T1-weighted images were acquired using spin echo pulse sequence (TR=200 ms, TE=16 ms, FOV=6 cm, matrix=256×196, slice thickness=2 mm), and T2-weighted images were acquired using a gradient echo pulse sequence (TR=3000 ms, TE=90 ms, FOV=6 cm, matrix=256×196, slice thickness=3 mm). T1-weigthed images were obtained following intraperitoneal injection of 0.1 mmol/kg of gadopentetate dimeglumine (Magnevist, Berlex Laboratories, N.J., USA). In all rats, humane euthanasia was performed by cervical dislocation approximately 1 hr post-treatment, and the brain was removed and fixed intact in 10% neutral buffered formalin. Following fixation for 48 hours, an adult rat brain matrix slicer (Zivic Instruments, Pittsburg, Pa.) was used to obtain contiguous 2 mm coronal brain sections from each animal. Brain and sections were embedded routinely in paraffin, sectioned at 5 μm, and stained with hematoxylin and eosin (H&E).

Treatments evaluated in this study produced ablative lesions in brain tissue, as evaluated with MRI examinations (FIGS. 21A-F) and pathologic preparations (FIGS. 20A-D). In Rats #3 and #4, the MRI characteristics of both H-FIRE and IRE lesions were similar. The MRI appearance of lesions in rat brain appeared as focal, ovoid to elliptical, T1 iso- to hypo-intense, uniformly and markedly contrast enhanced (FIGS. 21A, B, C, D, F) and T2 hyper-intense (FIG. 21E). In all panels, lesions appear as focal hyperintense regions (white) compared to adjacent untreated cerebrocortical tissue (gray). Top Panels (A-C) obtained from Rat #3, in which both the left and right cerebral hemispheres were treated with high-frequency waveforms at 300 V/250 kHz and 400 V/250 kHz, respectively. Bottom Panels (D-F), Rat #4, which underwent high-frequency, bipolar pulses in the right cerebrum at 400 V/500 kHz, and conventional IRE with unipolar pulses at 50 V in the left cerebrum. Panels A and D, post-gadolinium T1-weighted MRI sequences in the axial plane. Panel B, post-gadolinium T1-weighted MRI sequences in the right parasagittal plane. Panels C and F, post-gadolinium T1-weighted MRI sequences in the dorsal plane. Panel D, T2-weighted MRI sequence in the transverse plane. In all panels, the right side of the brain is on the left side of the panel.

All lesions were well demarcated from adjacent, normal brain tissue and appeared similar in size. Compared to untreated brain (FIGS. 20A and B), histopathologic examination of brain sections from all treatments demonstrated clear areas of ablation indicated by pallor of the treated tissue that was sharply delineated from adjacent normal brain (FIG. 20C). H-FIRE and IRE lesions were predominantly characterized by areas of complete obliteration of cerebrocortical architecture by an eosinophilic, vacuolated amorphous debris (FIGS. 20C and D). In Rat #1, the H-FIRE ablation zone was confined to regions of elevated electric field surrounding the electrodes, whereas all other pulsing protocols resulted in ablation zones spanning the entire region between the electrodes. Cavitary cerebrocortical defects were induced with H-FIRE in Rat #1 and IRE in Rat #4. Variably sized regions of intraparenchymal hemorrhage were most pronounced immediately adjacent to and within electrode insertion tracks. The morphology of remnant neuronal and glial elements within H-FIRE ablated regions demonstrated features of both apoptosis and necrosis, including shrunken and hypereosinophilic cytoplasm, nuclear chromatin condensation, and nuclear pyknosis and karyolysis (FIG. 20D). Free glial and neuronal nuclei in various states of degeneration were scattered throughout ablation zones. Inflammation was not a significant feature of IRE or H-FIRE lesions at the time point brains were examined.

Example 8

Elimination of muscle contractions during high-frequency IRE (H-FIRE) of brain tissue.

Figure 23:
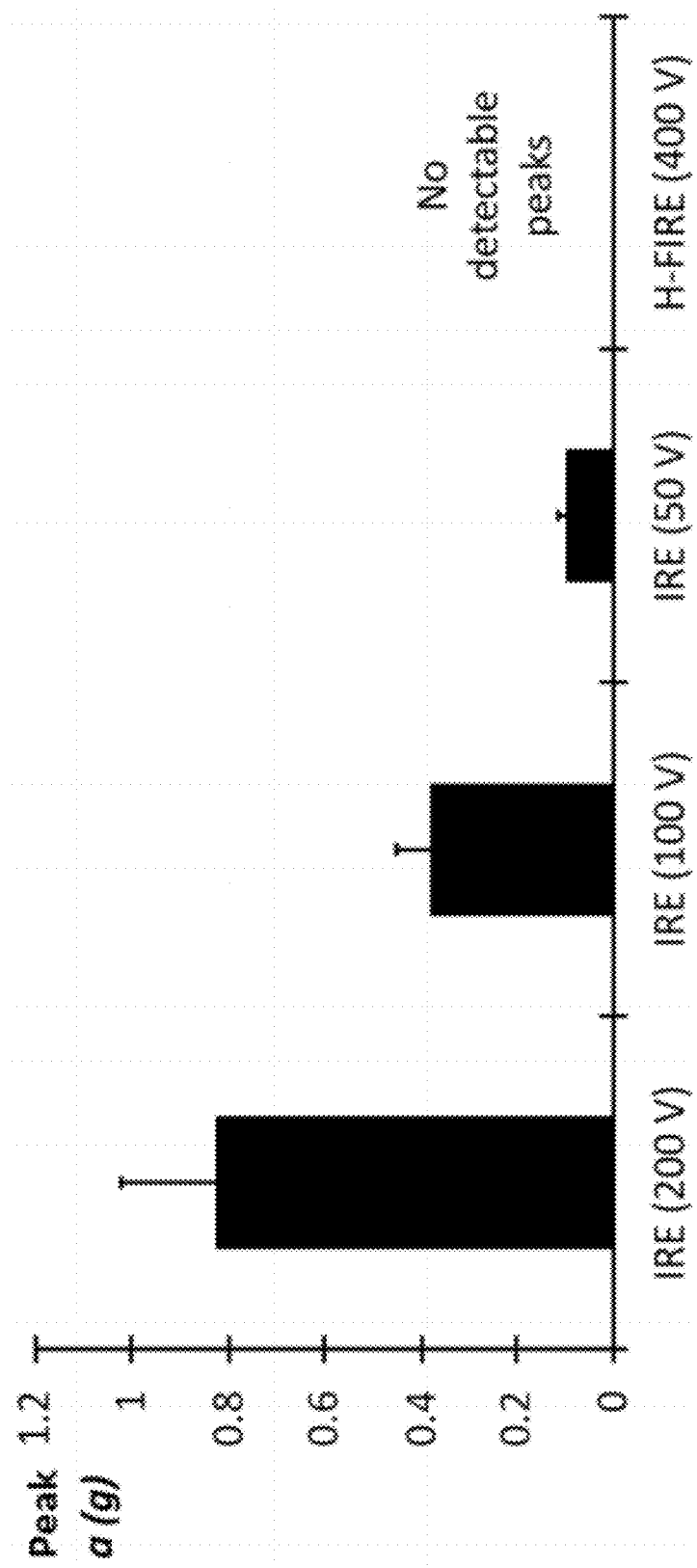
FIG. 23 is a chart showing peak acceleration (a) during pulsing protocols averaged over the first 90 pulses.

Muscle contractions were monitored throughout the procedure described in EXAMPLE 7 with the accelerometer located in the interscapular region at the cervicothoracic junction. All IRE pulsing protocols were associated with macroscopic muscular contractions of the cervicothoracic junction, which were also palpable to the neurosurgeon, while no visual or tactile evidence of muscular contraction was seen during any of the H-FIRE bursts. These results were quantitatively confirmed by the data recordings from the accelerometer (FIGS. 22A-D). Peak acceleration was determined during the first 90 bursts of the highest energy H-FIRE protocol (400 V/250 kHz) and the first 90 pulses of each IRE protocol (50 V, 100 V, 200 V). A one-way ANOVA was used to investigate the effects of each protocol on the ranks of peak acceleration at the cervicothoracic junction. In the event of a significant main effect, pairwise comparisons were completed using Tukey's Honestly Significant Difference (HSD). All statistical analyses were conducted using JMP 7 (Cary, N.C., USA) with a significance level of $p \leq 0.05$. Results indicate that, even in the highest energy H-FIRE protocol, there are no detectable peaks in acceleration above the inherent noise of the system. However, in all IRE protocols, peaks in acceleration associated with each pulse are detectable above the baseline noise. Further, pairwise comparisons between the various IRE protocols indicated that the mean peak acceleration during each treatment was energy dependent. Specifically, the mean peak acceleration decreased as the applied voltage decreased (FIG. 23).

Example 9

Experimental results of high-frequency IRE (H-FIRE) of liver tissue.

All study procedures were conducted following Institutional Animal Care and Use Committee approval and performed in a GLP compliant facility. Two, Fischer 344 male rats weighing 200-240 g were anesthetized by intraperitoneal injection of 10 mg/kg xylazine and 60 mg/kg ketamine hydrochloride, and a surgical plane of anesthesia was assessed by loss of the tail pinch reflex. A routine laparotomy surgical approach to the abdomen was made in order to expose the liver. Custom electrodes were inserted into the liver parenchyma and advanced to a depth of 2 mm beneath the surface. The electrodes were fashioned from steel pins (Dritz, 0.5 mm diameter), and the edge-to-edge electrode spacing was set to 1 mm by inserting the electrodes in a custom polycarbonate spacer.

In Rat #1, H-FIRE was applied at 1000 V/cm with 80 unipolar bursts at a center frequency of 2 MHz and, 50% duty cycle, and 50 µs burst width. In Rat #2 IRE was applied at an equivalent energy using 80 unipolar pulses with a duration of 50 µs and amplitude of 1000 V/cm. In all rats, humane euthanasia was performed by cervical dislocation approximately 1 hr post-treatment, and the liver was removed and fixed intact in 10% neutral buffered formalin. Following fixation for 48 hours, 5 mm sections from each animal were obtained and embedded routinely in paraffin, sectioned at 5 µm, and stained with hematoxylin and eosin (H&E).

Figure 19B:
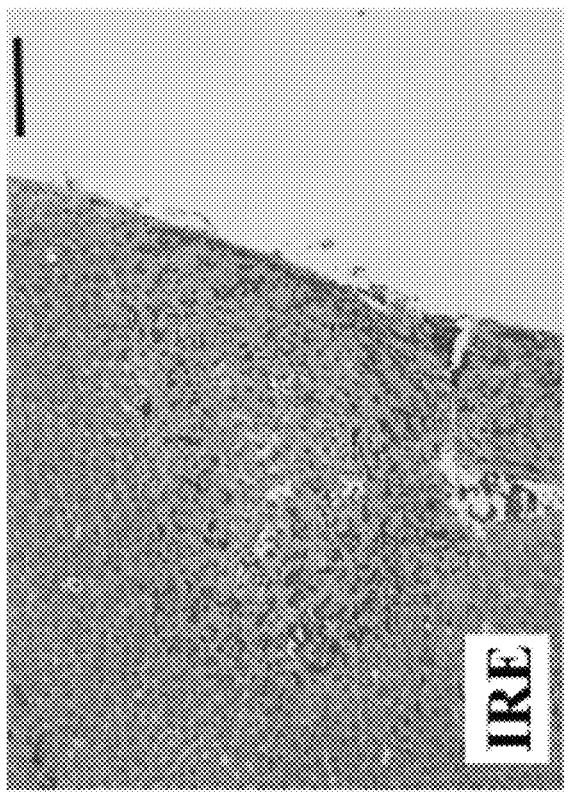
FIGS. 19A-B are photographs showing histological sections of liver tissue treated with high-frequency IRE (FIG. 19A) and conventional IRE with unipolar (FIG. 19B), with cross sections of tissue taken between the electrodes (scale bar=250 µm).
Figure 19A:

Histologically, in both treatments, there is evidence of necrosis and sinusoidal congestion (FIGS. 19A-B). Additionally, the lesions are well demarcated with cell scale resolution between treated and untreated tissue. Both of these features are common to IRE ablation of liver. No evidence of muscle contraction was observed visually. These results supplement those presented in EXAMPLE 7 and confirm that H-FIRE ablation can be achieved in multiple tissue types.

Example 10

The electric field distribution during high-frequency electroporation can be approximated by the Laplace equation.

A 2D axisymmetric FEM representative of a slab of non-infiltrated fat adjacent to dry skin was simulated using COMSOL 4.2a (Burlington, Mass.). An energized and grounded electrode were modeled as infinite fins (0.5 mm diameter) separated 0.5 cm from the skin-fat interface, for a total spacing of 1 cm. The electric potential distribution within the tissue was obtained by transiently solving Equation 7 (see Example 1). Additionally, the homogeneous solution was solved according to the Laplace equation:

$$-\nabla \cdot (\nabla \Phi) = 0 \quad (11)$$

For the heterogeneous case, the dielectric properties of various tissues were chosen from data generated by Gabriel et al. available at (http://niremf.ifac.cnr.it/docs/dielectric/home.html). Gabriel, S., R. W. Lau, and C. Gabriel, *The dielectric properties of biological tissues .2. Measurements in the frequency range 10 Hz to 20 GHz*. Physics in Medicine and Biology, 1996. 41(11): p. 2251-2269. The data was interpolated in Mathematica 7 (Wolfram Research, Inc.) in order to estimate the dielectric properties at 1 kHz and 1 MHz. For the homogeneous case, the electric field distribution is independent of the dielectric properties. The energized and grounded electrodes were subtracted from the skin and fat subdomains, and treated purely as boundary conditions at 1000 V and 0V, respectively.

FIGS. 24A and B show the electric field distribution during a bipolar burst with the frequencies given in TABLE 6.

TABLE 6

Dielectric properties of skin and fat tissue at various frequencies.

| Frequency | Property | Tissue | |
|---|---|---|---|
| | | Skin | Fat |
| 1 kHz | σ [S/m] | 0.000180 | 0.0246 |
| | $\epsilon_r$ | 1170 | 20800 |
| 1 MHz | σ [S/m] | 0.0119 | 0.0267 |
| | $\epsilon_r$ | 792 | 25 |

From the surface contour map, at 1 kHz, which is representative of a 500 µs traditional electroporation pulse, the electric field is highly non-uniform. A majority of the voltage drop occurs within the skin layer, and the fat layer remains untreated. However, at 1 MHz, which is representative of a 500 ns high-frequency electroporation pulse, the voltage drop is distributed more uniformly throughout the entire domain. As a result, both the skin and fat layers can be treated. Additionally, the electric field distribution at 1 MHz closely resembles that of the homogenous solution. Therefore, knowledge of dielectric properties and intricate geometrical arrangements of heterogeneous tissues can be neglected during treatment planning for high-frequency electroporation. This greatly reduces treatment planning protocols and produces more predictable outcomes.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. As used in this specification, the singular forms "a," "an," and "the" include plural referents unless the context clearly dictates otherwise. It is intended that the specification and examples be considered as exemplary in nature and that variations that do not depart from the essence of the invention are intended to be within the scope of the invention. Further, the references cited in this disclosure are incorporated by reference herein in their entireties.

The invention claimed is:

1. A medical device for killing tissue cells by non-thermal irreversible electroporation comprising:
   one or more electrodes adapted to be positioned near a target area containing target tissue cells to be killed;
   a power supply adapted to generate and deliver electrical pulses to the electrodes; and
   a controller in operable connection with and comprising programming of predetermined pulse parameters configured to control the power supply to output one or more bursts of the electrical pulses, each burst containing multiple electrical pulses at a frequency rate of 50 kHz or higher and capable of killing the target tissue cells by non-thermal irreversible electroporation, and each electrical pulse having a pulse width of 10 microseconds or less so as to kill the target tissue cells by non-thermal irreversible electroporation;

wherein the controller comprises programming for independent selection of width and amplitude of positive and negative pulses within one or more of the bursts and to allow for a delay between each burst of pulses; and wherein the controller comprises programming to control the power supply to output the negative pulses with an amplitude of between 500-4,000 V/cm.

2. The medical device of claim 1, wherein the controller comprises programming to control the power supply to output the electrical pulses within the burst, wherein the frequency rate is between 50 kHz and 2 MHz, inclusive.

3. The medical device of claim 1, wherein the controller comprises programming to control the power supply to output the electrical pulses within the burst, wherein the frequency rate is between 250 kHz and 2 MHz, inclusive.

4. The medical device of claim 3, wherein the controller comprises programming to control the power supply to output one or more of the bursts with multiple bipolar pulses.

5. The medical device of claim 1, wherein the controller comprises programming to control the power supply to output each electrical pulse having a pulse width of 100 nanoseconds or greater.

6. The medical device of claim 1, wherein the controller comprises programming to control the power supply to output each electrical pulse having a pulse width of between 250 nanoseconds and 2 microseconds, inclusive.

7. The medical device of claim 6, wherein the controller comprises programming to control the power supply to output one or more of the bursts with multiple bipolar pulses.

8. The medical device of claim 1, wherein the controller comprises programming to control the power supply to generate at least one burst of bipolar electrical pulses with a delay of zero between a positive pulse and an adjacent negative pulse in the burst of bipolar electrical pulses.

9. The medical device of claim 1, wherein the controller comprises programming to control the power supply to generate at least two bursts of bipolar electrical pulses with a delay of at least 75 microseconds between the bursts.

10. The method of claim 1, wherein the controller comprises programming to control the power supply to generate at least one burst of bipolar electrical pulses with multiple pulses in a single phase before a polarity switch.

11. The medical device of claim 1, wherein the controller comprises programming to control the power supply to output a burst of electrical pulses which is sufficient to cause a transmembrane potential (TMP) of the target tissue cells to rise above a critical threshold (CT) for inducing electroporation while a single electrical pulse in the burst of electrical pulses is insufficient to cause the TMP of the target tissue cells to rise above the CT.

12. The medical device of claim 1, wherein the controller comprises programming to control the power supply to output electrical pulses wherein each electrical pulse is sufficient to cause a transmembrane potential (TMP) of the target tissue cells to rise above a critical threshold (CT) for inducing electroporation.

13. The medical device of claim 12, wherein the critical threshold (CT) is in the range of 0.5-1.46 V, inclusive.

14. The medical device of claim 1, wherein the controller comprises programming to control the power supply to output a burst of electrical pulses which is sufficient to cause a transmembrane potential (TMP) of the target tissue cells to rise above a critical threshold for inducing irreversible electroporation (CTIRE) while a single electrical pulse in the burst of electrical pulses is insufficient to cause the TMP of the target tissue cells to rise above the CTIRE.

15. The medical device of claim 14, wherein the CTIRE is about 1 Volt.

16. The medical device of claim 1, wherein the controller comprises programming to control the power supply to output electrical pulses wherein each electrical pulse is sufficient to cause a transmembrane potential (TMP) of the target tissue cells to rise above a critical threshold (CT) for inducing irreversible electroporation.

17. The medical device of claim 1, wherein the controller comprises programming to control the power supply to generate the electrical pulses at 2500 V/cm or lower.

18. The medical device of claim 1, wherein the controller comprises programming to control voltage and pulse width of the electrical pulses to reduce tissue stimulation sufficiently to perform the target tissue cell killing without using general anesthesia.

19. A medical device for killing tissue cells of a living mammal by high frequency non-thermal irreversible electroporation without using general anesthesia comprising:
one or more electrodes adapted to be positioned near a target area containing target tissue cells to be killed;
a power supply adapted to generate and deliver electrical pulses to the electrodes; and
a controller in operable connection with and comprising programming of predetermined pulse parameters configured to control the power supply to output one or more bursts of the electrical pulses, each burst containing multiple electrical pulses at a high frequency rate of at least 50 kHz and capable of killing the target tissue cells by non-thermal irreversible electroporation, and each electrical pulse having a pulse duration of 10 microseconds or less to minimize tissue stimulation, wherein the controller comprises programming to allow for independent selection of width and amplitude of positive and negative pulses within one or more of the bursts and to allow for a delay between each of the positive and negative pulses within one or more of the bursts.

20. The medical device of claim 19, wherein the controller comprises programming to control the power supply to output bipolar electrical pulses within the burst, wherein the frequency rate is between 250 kHz and 2 MHz, inclusive.

21. The medical device of claim 19, wherein the controller comprises programming to control the power supply to output the electrical pulses within the burst, wherein the frequency rate is between 250 kHz and 2 MHz, inclusive, and each electrical pulse has a pulse width of between 250 nanoseconds and 2 microseconds, inclusive.

22. The medical device of claim 4, wherein one of the bursts comprises a positive pulse with one amplitude and width and a negative pulse with a different amplitude or width.

23. The medical device of claim 7, wherein one of the bursts comprises a positive pulse with one amplitude and width and a negative pulse with a different amplitude or width.

24. The medical device of claim 19, wherein the width and amplitude are capable of administering electroporation to electrically excitable tissue with reduced stimulation of the tissue as compared with pulses having higher amplitude and greater width.

25. The medical device of claim 1, further comprising a capacitor bank.

26. The medical device of claim 25, further comprising a polarity switch, wherein an input of the polarity switch is in direct operable connection with an output of the capacitor bank.

27. The medical device of claim 26, further comprising current limiting resistors, wherein an output of the current limiting resistors is in direct operable connection with an input of the capacitor bank.

28. The medical device of claim 27, wherein an input of the current limiting resistors is in direct operable connection with an output of the power supply.

29. The medical device of claim 28, further comprising an arbitrary function generator, wherein an output of the arbitrary function generator is in direct operable connection with an input of the polarity switch.

30. The device of claim 1, wherein the controller comprises programming to allow for a delay between the bursts on the order of seconds.

31. The device of claim 1, wherein the controller comprises programming to allow for a delay between the pulses on the order of microseconds.

32. A medical device for killing tissue cells by non-thermal irreversible electroporation comprising:
two or more electrodes adapted to be positioned near a target area containing target tissue cells to be killed;
a power supply adapted to generate and deliver electrical pulses to the electrodes;
a controller in operable connection with and comprising programming of predetermined pulse parameters configured to control the power supply to output one or more bursts of the electrical pulses which include a frequency rate of 50 kHz or higher and are capable of killing the target tissue cells by non-thermal irreversible electroporation;
a positive and a negative polarity switch in communication with the power supply; and
a capacitor bank disposed between the power supply and the positive and negative polarity switches.

33. The medical device of claim 32, wherein the electrodes are spaced at least 1 mm apart.

34. The medical device of claim 33, wherein the electrodes are spaced up to 3 cm apart or less.

35. A medical device for killing target tissue by non-thermal irreversible electroporation comprising:
two or more electrodes adapted to be positioned near a target area containing target tissue to be killed;
a power supply adapted to generate and deliver electrical pulses to the electrodes;
a controller in operable connection with and comprising programming of predetermined pulse parameters configured to control the power supply to output one or more bursts of the electrical pulses which include a frequency rate of 50 kHz or higher and are capable of killing the target tissue by non-thermal irreversible electroporation, each burst containing multiple electrical pulses at a high frequency rate, and each electrical pulse having a pulse duration of 10 microseconds or less to minimize tissue stimulation;
wherein the controller comprises programming to control a delay between the pulse bursts; and
wherein the pulse parameters are sufficient to subject the target tissue to non-thermal irreversible electroporation without causing muscle cells located in or surrounding the target tissue to contract.

36. The medical device of claim 35, wherein the target tissue is comprised of liver tissue.

37. The medical device of claim 35, wherein the target tissue is comprised of brain tissue.

38. The medical device of claim 35, wherein the controller comprises programming to allow for selection of width and amplitude of positive and negative pulses within one or more of the bursts.

39. The medical device of claim 38, wherein the controller comprises programming to control a delay between each of the positive and negative pulses within one or more of the bursts.

40. The medical device of claim 38, wherein the negative pulses prevent action potential generation of cells of the target tissue.

41. The medical device of claim of claim 35, wherein each electrical pulse has a pulse duration of a single polarity of no more than 100 nanoseconds and an electrical field threshold of up to 1,000 V/cm.

42. The medical device of claim 35, wherein the controller comprises programming to deliver at least 90 total pulses to the target tissue.

43. The medical device of claim 42, wherein the controller comprises programming to deliver at least 90 total pulses to the target tissue without raising the temperature of the target tissue above 50 degrees Celsius.

* * * * *